US005744343A

United States Patent [19]
Draetta et al.

[11] Patent Number: 5,744,343
[45] Date of Patent: Apr. 28, 1998

[54] UBIQUITIN CONJUGATING ENZYMES

[75] Inventors: Giulio Draetta, Winchester; Mark Rolfe, Newton Upper Falls; Jens W. Eckstein, Cambridge; Guillaume Cottarel, Chestnut Hill, all of Mass.

[73] Assignee: Mitotix, Inc., Cambridge, Mass.

[21] Appl. No.: 305,520

[22] Filed: Sep. 13, 1994

Related U.S. Application Data

[63] Continuation-in-part of Ser. No. 247,904, May 23, 1994, which is a continuation-in-part of Ser. No. 176,937, Jan. 4, 1994, abandoned.

[51] Int. Cl.$^6$ .............. C12N 9/10; C12N 1/20; C12N 15/00; C07H 21/04
[52] U.S. Cl. ............ 435/193; 435/252.3; 435/254.11; 435/320.1; 435/325; 536/23.2; 536/23.4
[58] Field of Search ............ 435/69.1, 193, 435/252.3, 320.1, 254.11, 325; 536/23.2, 24.3

[56] References Cited

FOREIGN PATENT DOCUMENTS

| | | |
|---|---|---|
| WO 89/09829 | 10/1989 | WIPO. |
| WO 89/12678 | 12/1989 | WIPO. |
| WO 91/17245 | 11/1991 | WIPO. |
| WO 92/20804 | 11/1992 | WIPO. |
| WO 93/09235 | 5/1993 | WIPO. |

OTHER PUBLICATIONS

Adams et al. (1993) "Rapid cDNA sequencing (expressed sequence tags) from a directionally cloned human infant brain cDNA library" *Nature Genetics* 4:373–380.

Band et al. (1991) "Loss of p53 Protein in Human Papillomavirus Type 16 E6–Immortalized Human Mammary Epithelial Cells" *Journal of Virology*, 65(12):6671–6676.

Berleth et al. (1992) "Inhibition of Ubiquitin–Protein Ligase (E3) by Mono–and Bifunctional Phenylarsenoxides" *The Journal of Biological Chemistry* 267(23):16403–16411.

Bissonnette et al. (1992) "Apoptotic cell death induced by c–myc is inhibited by bcl–2" *Nature* 359:552–556.

Chen et al (1993) "Multiple Ubiquitin–Conjugating Enzymes Participate in the In Vivo Degradation of the Yeast MATα2 Repressor" *Cell* 74:357–369.

Cook et al. (1992) "Structure of a Diubiquitin Conjugate and a Model for Interaction with Ubiquitin Conjugating Enzyme(E2)" *The Journal of Biological Chemistry* 267(23):16467–16471.

Cook et al. (1993) "Tertiary Structures of Class I Ubiquitin–Conjugating Enzymes Are Highly Conserved: Crystal Structure of Yeast Ubc4" *Biochemistry* 32(50):13809–13817.

Crook et al. (1991) "Degradation of p53 Can Be Targeted by HPV E6 Sequences Distinct from Those Required for p53 Binding and Trans–Activation" *Cell* 67:547–556.

Dohmen et al. (1991) "The N–end rule is mediated by the UBC2(RAD6) ubiquitin–conjugating enzyme" *Proceedings of the National Academy of Sciences* 88:7351–7355.

Ellison et al. (1991) "Epitope–tagged Ubiquitin" *J Biol Chem* 266(31):21150–21157.

Evan et al. (1992) "Induction of Apoptosis in Fibroblasts by c–myc Protein" *Cell* 69:119–128.

Girod et al. (1993) "Homologs of the essential ubiquitin–conjugating enzymes UBC1, 4, and 5 in yeast are encoded by a multigene family in *Arabidopsis thaliana*" *The Plant Journal* 3(4):545–552.

Glotzer et al. (1991) "Cyclin is degraded by the ubiquitin pathway" *Nature* 349:132–138.

Hartwell et al. (1992) "Defects in a Cell Cycle Checkpoint May Be Responsible for the Genomic Instability of Cancer Cells" *Cell* 71:543–546.

Hershko et al. (1983) "Components of Ubiquitin–Protein Ligase System" *J Biol Chem* 258(13):8206–8214.

Hochstrasser et al. (1990) "In Vivo Degradation of a Transcriptional Regulator: The Yeast α2 Repressor" *Cell* 61:697–708.

Hoefer et al. (1991) "Purification and partial characterization of ubiquitin–activating enzyme from *Saccharomyces cerevisiae*" *FEBS Letters* 289(1):54–58.

Holloway et al. (1993) "Anaphase Is Initiated by Proteolysis Rather Than by the Inactivation of Maturation–Promoting Factor" *Cell* 73:1393–1402.

Huibregtse et al. (1993) "Localization of the E6–AP Regions That Direct Human Papillomavirus E6 Binding, Association with p53, and Ubiquitination of Associated Proteins" *Mol Cell Biol* 13(8):pp. 4918–4927.

Huibregtse et al. (1993) "Cloning and Expression of the cDNA for E6–AP, a Protein That Mediates the Interaction of the Human Papillomavirus E6 Oncoprotein with p53" *Mol Cell Biol* 13(2):775–784.

Huibregtse et al. (1991) "A cellular protein mediates association of p53 with the E6 oncoprotein of human papillomavirus types 16 or 18" *EMBO J* 10(3):4129–4135.

Hupp et al. (1992) "Regulation of the Specific DNA Binding Function of p53" *Cell* 71:875–886.

Jacobs et al. (1993) "Rapid Assessment of Drug Susceptibilities of *Mycobacterium tuberculosis* by Means of Luciferase Reporter Phages" *Science* 260:819–822.

Jentsch et al. (1992) "The Ubiquitin–conjugation System" *Ann Rev Genet* 26:179–207.

Klemperer et al. (1989) "A Novel, Arsenite–Sensitive E2 of the Ubiquitin Pathway: Purification and Properties" *Biochemistry* 28:6035–6041.

Koken et al. (1991) "Structural and Functional conservation of two human homologs of the yeast DNA repair gene *RAD6*" *PNAS* 88:8865–8869.

Milner et al. (1990) "p53 Is Associated with p34$^{cdc2}$ Transformed Cells" *EMBO J* 9(9):2885–2889.

(List continued on next page.)

*Primary Examiner*—Robert A. Wax
*Assistant Examiner*—Lisa J. Hobbs
*Attorney, Agent, or Firm*—Matthew P. Vincent, Esq.; Beth E. Arnold, Esq.; Foley, Hoag & Eliot LLP

[57] ABSTRACT

The present invention concerns three ubiquitin-conjugating enzymes.

27 Claims, 41 Drawing Sheets

OTHER PUBLICATIONS

Münger et al. (1989) "The E6 and E7 Genes of the Human Papillomavirus Type 16 Together Are Necessary and Sufficient for Transformation of Primary Human Keratinocytes" *J Virol* 63(10):4417–4421.

Nepveu et al.(1987) "Alternative Modes of c–myc regulation in growth factor–stimulated and differentiating cells" *Oncogene* 1:243–250.

Rechsteiner et al. (1991) "Natural Substrates of the Ubiquitin Proteolytic Pathway" *Cell* 66:615–618.

Schärer et al. (1992) "Mammalian p53 can function as a transcription factor in yeast" *Nucleic Acids Research* 20(7):1539–1545.

Scheffner et al. (1992) "Interaction of the Human Papillomavirus Type 16 E6 Oncoprotein with Wild–Type and Mutant Human p53 Proteins" *J Virol* 66(8):5100–5105.

Scheffner et al. (1990) "The E6 Oncoprotein Encoded by Human Papi;;omavirus Types 16 and 18 Promotes the Degradation of p53" *Cell* 63:1129–1136.

Scheffner et al. (1992) "Targeted degradation of the retinoblastoma protein by human papillomavirus E7–E6 fusion proteins" *EMBO J* 11(7):2425–2431.

Scheffner et al. (1993) "The HPV–16 E6 and E6–AP Complex Functions as a Ubiquitin–Protein Ligase in the Ubiquitination of p53" *Cell* 75:495–505.

Seufert and Jentsch (1990) "Ubiquitin–conjugating enzymes UBC4 and UBC5 mediate selective degradation of short–lived and abnormal proteins" *EMBO J* 9(2):543–550.

Treier et al. (1992) "*Drosophila UbcD1* encodes a highly conserved ubiquitin–conjugating enzyme involved in selective protein degradation" *EMBO J* 11(1):367–372.

Tyers et al. (1992) "The Cin3–Cdc28 kinase complex of *S. cerevisiae* is regulated by proteolysis and phosphorylation" *EMBO J* 11(5):1773–1784.

Watanabe et al. (1989) "Human Papillomavirus Type 16 Transformation of Primary Human embryonic Fibroblasts Requires Expression of Open Reading Frames E6 and E7" *J Virol* 63(2):965–969.

Zhen et al. (1993) "The ubc–2 Gene of *Caenorhabditis elegans* Encodes a Ubiquitin–Conjugating Enzyme Involved in Selective Protein Degradation" *Mol Cell Biol* 13(3):1371–1377.

| ATOM | 1 | N | ARG | 1 | 5 | 10.652 | 30.749 | 37.986 | 1.00 | 0.00 |
| --- | --- | --- | --- | --- | --- | --- | --- | --- | --- | --- |
| ATOM | 2 | CA | ARG | 1 | 5 | 10.654 | 30.876 | 39.370 | 1.00 | 0.00 |
| ATOM | 3 | C | ARG | 1 | 5 | 9.386 | 31.560 | 39.753 | 1.00 | 0.00 |
| ATOM | 4 | O | ARG | 1 | 5 | 9.153 | 32.661 | 39.298 | 1.00 | 0.00 |
| ATOM | 5 | CB | ARG | 1 | 5 | 11.872 | 31.683 | 39.871 | 1.00 | 0.00 |
| ATOM | 6 | CG | ARG | 1 | 5 | 12.638 | 31.033 | 41.051 | 1.00 | 0.00 |
| ATOM | 7 | CD | ARG | 1 | 5 | 11.956 | 31.005 | 42.439 | 1.00 | 0.00 |
| ATOM | 8 | NE | ARG | 1 | 5 | 11.007 | 29.919 | 42.560 | 1.00 | 0.00 |
| ATOM | 9 | CZ | ARG | 1 | 5 | 10.281 | 29.677 | 43.686 | 1.00 | 0.00 |
| ATOM | 10 | NH1 | ARG | 1 | 5 | 10.417 | 30.413 | 44.773 | 1.00 | 0.00 |
| ATOM | 11 | NH2 | ARG | 1 | 5 | 9.411 | 28.694 | 43.623 | 1.00 | 0.00 |
| ATOM | 12 | 1H | ARG | 1 | 5 | 10.497 | 29.737 | 37.803 | 1.00 | 0.00 |
| ATOM | 13 | 2H | ARG | 1 | 5 | 9.927 | 31.348 | 37.541 | 1.00 | 0.00 |
| ATOM | 14 | 3H | ARG | 1 | T | 11.573 | 31.167 | 37.744 | 1.00 | 0.00 |
| ATOM | 15 | HE | ARG | 1 | 5 | 10.888 | 29.459 | 41.680 | 1.00 | 0.00 |
| ATOM | 16 | 1HH1 | ARG | 1 | 5 | 9.832 | 30.497 | 45.580 | 1.00 | 0.00 |
| ATOM | 17 | 2HH1 | ARG | 1 | 5 | 11.297 | 30.876 | 44.878 | 1.00 | 0.00 |
| ATOM | 18 | 1HH2 | ARG | 1 | 5 | 8.878 | 28.410 | 44.420 | 1.00 | 0.00 |
| ATOM | 19 | 2HH2 | ARG | 1 | 5 | 9.283 | 28.223 | 42.749 | 1.00 | 0.00 |
| ATOM | 20 | N | ILE | 1 | 6 | 8.510 | 30.841 | 40.468 | 1.00 | 0.00 |
| ATOM | 21 | CA | ILE | 1 | 6 | 7.082 | 31.170 | 40.678 | 1.00 | 0.00 |
| ATOM | 22 | C | ILE | 1 | 6 | 6.442 | 31.065 | 39.284 | 1.00 | 0.00 |
| ATOM | 23 | O | ILE | 1 | 6 | 5.956 | 29.988 | 38.915 | 1.00 | 0.00 |
| ATOM | 24 | CB | ILE | 1 | 6 | 6.853 | 32.470 | 41.413 | 1.00 | 0.00 |
| ATOM | 25 | CG1 | ILE | 1 | 6 | 7.651 | 32.561 | 42.727 | 1.00 | 0.00 |
| ATOM | 26 | CG2 | ILE | 1 | 6 | 5.366 | 32.803 | 41.630 | 1.00 | 0.00 |
| ATOM | 27 | CD1 | ILE | 1 | 6 | 6.834 | 32.009 | 43.915 | 1.00 | 0.00 |
| ATOM | 28 | H | ILE | 1 | 6 | 8.808 | 29.963 | 40.841 | 1.00 | 0.00 |
| ATOM | 29 | N | HIS | 1 | 7 | 6.540 | 32.257 | 38.639 | 1.00 | 0.00 |
| ATOM | 30 | CA | HIS | 1 | 7 | 6.197 | 32.320 | 37.173 | 1.00 | 0.00 |
| ATOM | 31 | C | HIS | 1 | 7 | 7.002 | 31.274 | 36.346 | 1.00 | 0.00 |
| ATOM | 32 | O | HIS | 1 | 7 | 8.174 | 30.919 | 36.611 | 1.00 | 0.00 |
| ATOM | 33 | CB | HIS | 1 | 7 | 6.233 | 33.740 | 36.613 | 1.00 | 0.00 |
| ATOM | 34 | CG | HIS | 1 | 7 | 7.507 | 34.441 | 37.147 | 1.00 | 0.00 |
| ATOM | 35 | ND1 | HIS | 1 | 7 | 8.661 | 34.555 | 36.453 | 1.00 | 0.00 |
| ATOM | 36 | CD2 | HIS | 1 | 7 | 7.660 | 35.160 | 38.373 | 1.00 | 0.00 |
| ATOM | 37 | CE1 | HIS | 1 | 7 | 9.552 | 35.219 | 37.259 | 1.00 | 0.00 |
| ATOM | 38 | NE2 | HIS | 1 | 7 | 8.924 | 35.642 | 38.428 | 1.00 | 0.00 |
| ATOM | 39 | H | HIS | 1 | 7 | 7.119 | 32.928 | 39.101 | 1.00 | 0.00 |
| ATOM | 40 | 1HD | HIS | 1 | 7 | 8.806 | 34.258 | 35.530 | 1.00 | 0.00 |
| ATOM | 41 | N | LYS | 1 | 8 | 6.366 | 30.860 | 35.208 | 1.00 | 0.00 |
| ATOM | 42 | CA | LYS | 1 | 8 | 6.776 | 29.679 | 34.371 | 1.00 | 0.00 |
| ATOM | 43 | C | LYS | 1 | 8 | 6.529 | 28.399 | 35.097 | 1.00 | 0.00 |
| ATOM | 44 | O | LYS | 1 | 8 | 5.719 | 27.551 | 34.809 | 1.00 | 0.00 |
| ATOM | 45 | CB | LYS | 1 | 8 | 8.237 | 29.782 | 33.828 | 1.00 | 0.00 |

FIG. 1A

| ATOM | 46 | CG | LYS | 1 | 8 | 8.500 | 29.320 | 32.392 | 1.00 | 0.00 |
| ATOM | 47 | CD | LYS | 1 | 8 | 9.916 | 29.656 | 31.893 | 1.00 | 0.00 |
| ATOM | 48 | CE | LYS | 1 | 8 | 9.996 | 29.567 | 30.420 | 1.00 | 0.00 |
| ATOM | 49 | NZ | LYS | 1 | 8 | 11.060 | 30.278 | 29.662 | 1.00 | 0.00 |
| ATOM | 50 | H | LYS | 1 | 8 | 5.445 | 31.225 | 35.069 | 1.00 | 0.00 |
| ATOM | 51 | 1HZ | LYS | 1 | 8 | 10.982 | 31.309 | 29.543 | 1.00 | 0.00 |
| ATOM | 52 | 1HZ | LYS | 1 | 8 | 12.021 | 29.906 | 29.803 | 1.00 | 0.00 |
| ATOM | 53 | 3HZ | LYS | 1 | 8 | 11.084 | 30.047 | 28.648 | 1.00 | 0.00 |
| ATOM | 54 | N | GLU | 1 | 9 | 7.274 | 28.215 | 36.215 | 1.00 | 0.00 |
| ATOM | 55 | CA | GLU | 1 | 9 | 6.995 | 27.070 | 37.159 | 1.00 | 0.00 |
| ATOM | 56 | C | GLU | 1 | 9 | 5.445 | 26.859 | 37.570 | 1.00 | 0.00 |
| ATOM | 57 | O | GLU | 1 | 9 | 4.977 | 25.769 | 37.789 | 1.00 | 0.00 |
| ATOM | 58 | CB | GLU | 1 | 9 | 7.951 | 27.203 | 38.425 | 1.00 | 0.00 |
| ATOM | 59 | CG | GLU | 1 | 9 | 9.433 | 26.780 | 38.356 | 1.00 | 0.00 |
| ATOM | 60 | CD | GLU | 1 | 9 | 10.169 | 27.525 | 39.767 | 1.00 | 0.00 |
| ATOM | 61 | OE1 | GLU | 1 | 9 | 9.570 | 27.669 | 40.887 | 1.00 | 0.00 |
| ATOM | 62 | OE2 | GLU | 1 | 9 | 11.354 | 27.904 | 39.613 | 1.00 | 0.00 |
| ATOM | 63 | H | GLU | 1 | 9 | 7.918 | 28.973 | 36.320 | 1.00 | 0.00 |
| ATOM | 64 | N | LEU | 1 | 10 | 4.816 | 27.970 | 37.728 | 1.00 | 0.00 |
| ATOM | 65 | CA | LEU | 1 | 10 | 3.434 | 28.097 | 38.068 | 1.00 | 0.00 |
| ATOM | 66 | C | LEU | 1 | 10 | 3.047 | 29.230 | 37.145 | 1.00 | 0.00 |
| ATOM | 67 | O | LEU | 1 | 10 | 3.769 | 30.204 | 37.045 | 1.00 | 0.00 |
| ATOM | 68 | CB | LEU | 1 | 10 | 3.176 | 28.409 | 39.531 | 1.00 | 0.00 |
| ATOM | 69 | CG | LEU | 1 | 10 | 2.041 | 27.485 | 40.074 | 1.00 | 0.00 |
| ATOM | 70 | CD1 | LEU | 1 | 10 | 0.728 | 27.903 | 39.503 | 1.00 | 0.00 |
| ATOM | 71 | CD2 | LEU | 1 | 10 | 2.366 | 26.000 | 39.832 | 1.00 | 0.00 |
| ATOM | 72 | H | LEU | 1 | 10 | 5.291 | 28.782 | 37.389 | 1.00 | 0.00 |
| ATOM | 73 | N | LEU | 1 | 11 | 1.850 | 29.001 | 36.566 | 1.00 | 0.00 |
| ATOM | 74 | CA | ASN | 1 | 11 | 1.355 | 29.849 | 35.463 | 1.00 | 0.00 |
| ATOM | 75 | C | ASN | 1 | 11 | -0.107 | 30.195 | 35.375 | 1.00 | 0.00 |
| ATOM | 76 | O | ASN | 1 | 11 | -0.745 | 29.756 | 34.411 | 1.00 | 0.00 |
| ATOM | 77 | CB | ASN | 1 | 11 | 2.047 | 29.486 | 34.124 | 1.00 | 0.00 |
| ATOM | 78 | CG | ASN | 1 | 11 | 1.754 | 30.546 | 33.096 | 1.00 | 0.00 |
| ATOM | 79 | OD1 | ASN | 1 | 11 | 1.217 | 31.610 | 33.377 | 1.00 | 0.00 |
| ATOM | 80 | ND2 | ASN | 1 | 11 | 1.971 | 30.162 | 31.811 | 1.00 | 0.00 |
| ATOM | 81 | H | ASN | 1 | 11 | 1.420 | 28.167 | 36.911 | 1.00 | 0.00 |
| ATOM | 82 | 1HD2 | ASN | 1 | 11 | 2.285 | 29.261 | 31.512 | 1.00 | 0.00 |
| ATOM | 83 | 2HD2 | ASN | 1 | 11 | 1.643 | 30.782 | 31.098 | 1.00 | 0.00 |
| ATOM | 84 | N | ASP | 1 | 12 | -0.619 | 30.939 | 36.323 | 1.00 | 0.00 |
| ATOM | 85 | CA | ASP | 1 | 12 | -2.064 | 31.262 | 36.250 | 1.00 | 0.00 |
| ATOM | 86 | C | ASP | 1 | 12 | -2.668 | 31.635 | 34.910 | 1.00 | 0.00 |
| ATOM | 87 | O | ASP | 1 | 12 | -3.709 | 31.008 | 34.539 | 1.00 | 0.00 |
| ATOM | 88 | CB | ASP | 1 | 12 | -2.517 | 32.237 | 37.409 | 1.00 | 0.00 |
| ATOM | 89 | CG | ASP | 1 | 12 | -1.293 | 32.675 | 38.157 | 1.00 | 0.00 |
| ATOM | 90 | OD1 | ASP | 1 | 12 | -0.497 | 33.446 | 37.645 | 1.00 | 0.00 |

FIG. 1B

| | | | | | | | | | |
|---|---|---|---|---|---|---|---|---|---|
| ATOM | 91 | OD2 | ASP | 1 | 12 | -1.057 | 32.123 | 39.266 | 1.00 0.00 |
| ATOM | 92 | H | ASP | 1 | 12 | -0.119 | 31.179 | 37.155 | 1.00 0.00 |
| ATOM | 93 | N | LEU | 1 | 13 | -2.099 | 32.601 | 34.132 | 1.00 0.00 |
| ATOM | 94 | CA | LEU | 1 | 13 | -2.827 | 33.180 | 32.995 | 1.00 0.00 |
| ATOM | 95 | C | LEU | 1 | 13 | -2.951 | 32.329 | 31.780 | 1.00 0.00 |
| ATOM | 96 | O | LEU | 1 | 13 | -3.808 | 32.567 | 30.921 | 1.00 0.00 |
| ATOM | 97 | CB | LEU | 1 | 13 | -2.337 | 34.600 | 32.584 | 1.00 0.00 |
| ATOM | 98 | CG | LEU | 1 | 13 | -3.491 | 35.515 | 32.232 | 1.00 0.00 |
| ATOM | 99 | CD1 | LEU | 1 | 13 | -4.133 | 36.006 | 33.554 | 1.00 0.00 |
| ATOM | 100 | CD2 | LEU | 1 | 13 | -2.935 | 36.524 | 31.217 | 1.00 0.00 |
| ATOM | 101 | H | LEU | 1 | 13 | -1.276 | 33.096 | 34.308 | 1.00 0.00 |
| ATOM | 102 | N | ALA | 1 | 14 | -2.089 | 31.252 | 31.763 | 1.00 0.00 |
| ATOM | 103 | CA | ALA | 1 | 14 | -2.227 | 30.131 | 30.792 | 1.00 0.00 |
| ATOM | 104 | C | ALA | 1 | 14 | -3.449 | 29.293 | 31.048 | 1.00 0.00 |
| ATOM | 105 | O | ALA | 1 | 14 | -3.724 | 28.399 | 30.301 | 1.00 0.00 |
| ATOM | 106 | CB | ALA | 1 | 14 | -1.062 | 29.249 | 30.600 | 1.00 0.00 |
| ATOM | 107 | H | ALA | 1 | 14 | -1.479 | 31.103 | 32.541 | 1.00 0.00 |
| ATOM | 108 | N | ARG | 1 | 15 | -4.037 | 29.445 | 32.285 | 1.00 0.00 |
| ATOM | 109 | CA | ARG | 1 | 15 | -5.241 | 28,633 | 32.573 | 1.00 0.00 |
| ATOM | 110 | C | ARG | 1 | 15 | -6.478 | 29.572 | 32.619 | 1.00 0.00 |
| ATOM | 111 | O | ARG | 1 | 15 | -7.563 | 29.184 | 32.147 | 1.00 0.00 |
| ATOM | 112 | CB | ARG | 1 | 15 | -5.074 | 27.850 | 33.877 | 1.00 0.00 |
| ATOM | 113 | CG | ARG | 1 | 15 | -5.256 | 26.348 | 33.808 | 1.00 0.00 |
| ATOM | 114 | CD | ARG | 1 | 15 | -6.599 | 25.816 | 34.374 | 1.00 0.00 |
| ATOM | 115 | NE | ARG | 1 | 15 | -7.738 | 26.515 | 33.767 | 1.00 0.00 |
| ATOM | 116 | CZ | ARG | 1 | 15 | -8.322 | 27.475 | 34.535 | 1.00 0.00 |
| ATOM | 117 | NH1 | ARG | 1 | 15 | -9.426 | 28.064 | 34.120 | 1.00 0.00 |
| ATOM | 118 | NH2 | ARG | 1 | 15 | -7.720 | 27.973 | 35.652 | 1.00 0.00 |
| ATOM | 119 | H | ARG | 1 | 15 | -3.720 | 30.097 | 32.975 | 1.00 0.00 |
| ATOM | 120 | HE | ARG | 1 | 15 | -8.062 | 26.201 | 32.875 | 1.00 0.00 |
| ATOM | 121 | 1HH1 | ARG | 1 | 15 | -9.878 | 28.795 | 34.631 | 1.00 0.00 |
| ATOM | 122 | 2HH1 | ARG | 1 | 15 | -9.779 | 27,853 | 33.209 | 1.00 0.00 |
| ATOM | 123 | 1HH2 | ARG | 1 | 15 | -8.137 | 28.803 | 36.022 | 1.00 0.00 |
| ATOM | 124 | 2HH2 | ARG | 1 | 15 | -6.866 | 27.700 | 36.093 | 1.00 0.00 |
| ATOM | 125 | N | ASP | 1 | 16 | -6.237 | 30.813 | 33.067 | 1.00 0.00 |
| ATOM | 126 | CA | ASP | 1 | 16 | -7.250 | 31.856 | 32.803 | 1.00 0.00 |
| ATOM | 127 | C | ASP | 1 | 16 | -6.824 | 33.136 | 32.067 | 1.00 0.00 |
| ATOM | 128 | O | ASP | 1 | 16 | -6.532 | 34.221 | 32.610 | 1.00 0.00 |
| ATOM | 129 | CB | ASP | 1 | 16 | -8.089 | 32.302 | 34.005 | 1.00 0.00 |
| ATOM | 130 | CG | ASP | 1 | 16 | -8.462 | 31.097 | 34.974 | 1.00 0.00 |
| ATOM | 131 | OD1 | ASP | 1 | 16 | -9.602 | 30.692 | 34.912 | 1.00 0.00 |
| ATOM | 132 | OD2 | ASP | 1 | 16 | -7.672 | 30.572 | 35.769 | 1.00 0.00 |
| ATOM | 133 | H | ASP | 1 | 16 | -5.451 | 31.212 | 33.539 | 1.00 0.00 |
| ATOM | 134 | N | PRO | 1 | 17 | -6.956 | 33.072 | 30.746 | 1.00 0.00 |
| ATOM | 135 | CA | PRO | 1 | 17 | -6.993 | 34.342 | 30.013 | 1.00 0.00 |

FIG. 1C

| | | | | | | | | | |
|---|---|---|---|---|---|---|---|---|---|
| ATOM | 136 | C | PRO | 1 | 17 | -8.205 | 35.156 | 30.521 | 1.00 0.00 |
| ATOM | 137 | O | PRO | 1 | 17 | -9.305 | 34.673 | 30.362 | 1.00 0.00 |
| ATOM | 138 | CB | PRO | 1 | 17 | -7.265 | 33.841 | 28.530 | 1.00 0.00 |
| ATOM | 139 | CG | PRO | 1 | 17 | -6.733 | 32.384 | 28.576 | 1.00 0.00 |
| ATOM | 140 | CD | PRO | 1 | 17 | -7.148 | 31.899 | 29.962 | 1.00 0.00 |
| ATOM | 141 | N | PRO | 1 | 18 | -7.965 | 36.355 | 31.086 | 1.00 0.00 |
| ATOM | 142 | CA | PRO | 1 | 18 | -9.083 | 37.138 | 31.627 | 1.00 0.00 |
| ATOM | 143 | C | PRO | 1 | 18 | -9.936 | 37.823 | 30.552 | 1.00 0.00 |
| ATOM | 144 | O | PRO | 1 | 18 | -10,510 | 37.184 | 29.678 | 1.00 0.00 |
| ATOM | 145 | CB | PRO | 1 | 18 | -8.415 | 37.993 | 32.696 | 1.00 0.00 |
| ATOM | 146 | CG | PRO | 1 | 18 | -6.972 | 38.217 | 32.269 | 1.00 0.00 |
| ATOM | 147 | CD | PRO | 1 | 18 | -6.703 | 36.974 | 31.360 | 1.00 0.00 |
| ATOM | 148 | N | ALA | 1 | 19 | -10.151 | 39.105 | 30.790 | 1.00 0.00 |
| ATOM | 149 | CA | ALA | 1 | 19 | -11.197 | 39.768 | 29.931 | 1.00 0.00 |
| ATOM | 150 | C | ALA | 1 | 19 | -10.607 | 40.086 | 28.534 | 1.00 0.00 |
| ATOM | 151 | O | ALA | 1 | 19 | -10.127 | 41.187 | 28.324 | 1.00 0.00 |
| ATOM | 152 | CB | ALA | 1 | 19 | -11.617 | 41.179 | 30.598 | 1.00 0.00 |
| ATOM | 153 | H | ALA | 1 | 19 | -9.561 | 39.653 | 31.383 | 1.00 0.00 |
| ATOM | 154 | N | GLN | 1 | 20 | -10.496 | 39.036 | 27.758 | 1.00 0.00 |
| ATOM | 155 | CA | GLN | 1 | 20 | -9.643 | 38.863 | 26.552 | 1.00 0.00 |
| ATOM | 156 | C | GLN | 1 | 20 | -8.342 | 39.556 | 26.683 | 1.00 0.00 |
| ATOM | 157 | O | GLN | 1 | 20 | -8.219 | 40.714 | 26.316 | 1.00 0.00 |
| ATOM | 158 | CB | GLN | 1 | 20 | -10.452 | 39.059 | 25.250 | 1.00 0.00 |
| ATOM | 159 | CG | GLN | 1 | 20 | -11.446 | 40.245 | 25.067 | 1.00 0.00 |
| ATOM | 160 | CD | GLN | 1 | 20 | -12.575 | 40.215 | 26.077 | 1.00 0.00 |
| ATOM | 161 | OE1 | GLN | 1 | 20 | -12.883 | 41.218 | 26.660 | 1.00 0.00 |
| ATOM | 162 | NE2 | GLN | 1 | 20 | -13.154 | 39.042 | 26.289 | 1.00 0.00 |
| ATOM | 163 | H | GLN | 1 | 20 | -11.149 | 38.324 | 28.017 | 1.00 0.00 |
| ATOM | 164 | 1HE2 | GLN | 1 | 20 | -12.901 | 38.240 | 25.748 | 1.00 0.00 |
| ATOM | 165 | 2HE2 | GLN | 1 | 20 | -13.792 | 38.993 | 27.058 | 1.00 0.00 |
| ATOM | 166 | N | CYS | 1 | 21 | -7.381 | 38.866 | 27.312 | 1.00 0.00 |
| ATOM | 167 | CA | CYS | 1 | 21 | -5.983 | 39.312 | 27.548 | 1.00 0.00 |
| ATOM | 168 | C | CYS | 1 | 21 | -5.049 | 38.159 | 27.644 | 1.00 0.00 |
| ATOM | 169 | O | CYS | 1 | 21 | -5.488 | 37.103 | 28.037 | 1.00 0.00 |
| ATOM | 170 | CB | CYS | 1 | 21 | -5.939 | 40.115 | 28.837 | 1.00 0.00 |
| ATOM | 171 | SG | CYS | 1 | 21 | -6.547 | 41.738 | 28.478 | 1.00 0.00 |
| ATOM | 172 | H | CYS | 1 | 21 | -7.581 | 37.909 | 27.521 | 1.00 0.00 |
| ATOM | 173 | N | SER | 1 | 22 | -3.768 | 38,479 | 27.242 | 1.00 0.00 |
| ATOM | 174 | CA | SER | 1 | 22 | -2.909 | 37.373 | 26.846 | 1.00 0.00 |
| ATOM | 175 | C | SER | 1 | 22 | -1.484 | 37.385 | 27.299 | 1.00 0.00 |
| ATOM | 176 | O | SER | 1 | 22 | -0.890 | 38.502 | 27.246 | 1.00 0.00 |
| ATOM | 177 | CB | SER | 1 | 22 | -3.010 | 37.109 | 25.307 | 1.00 0.00 |
| ATOM | 178 | OG | SER | 1 | 22 | -4.179 | 37.764 | 24.726 | 1.00 0.00 |
| ATOM | 179 | H | SER | 1 | 22 | -3.415 | 39.413 | 27.183 | 1.00 0.00 |
| ATOM | 180 | HG | SER | 1 | 22 | -3.987 | 37.872 | 23.804 | 1.00 0.00 |

FIG. 1D

| ATOM | 181 | N | ALA | 1 | 23 | -0.882 | 36.264 | 27.816 | 1.00 | 0.00 |
| ATOM | 182 | CA | ALA | 1 | 23 | 0.449 | 36.497 | 28.382 | 1.00 | 0.00 |
| ATOM | 183 | C | ALA | 1 | 23 | 1.533 | 35.875 | 27.516 | 1.00 | 0.00 |
| ATOM | 184 | O | ALA | 1 | 23 | 1.418 | 34.935 | 26.775 | 1.00 | 0.00 |
| ATOM | 185 | CB | ALA | 1 | 23 | 0.545 | 35.912 | 29.743 | 1.00 | 0.00 |
| ATOM | 186 | H | ALA | 1 | 23 | -1.458 | 35.449 | 27.752 | 1.00 | 0.00 |
| ATOM | 187 | N | GLY | 1 | 24 | 2.746 | 36.445 | 27.787 | 1.00 | 0.00 |
| ATOM | 188 | CA | GLY | 1 | 24 | 3.850 | 35.741 | 27.233 | 1.00 | 0.00 |
| ATOM | 189 | C | GLY | 1 | 24 | 5.127 | 36.253 | 27.699 | 1.00 | 0.00 |
| ATOM | 190 | O | GLY | 1 | 24 | 5.075 | 37.310 | 28.265 | 1.00 | 0.00 |
| ATOM | 191 | H | GLY | 1 | 24 | 3.000 | 37.253 | 28.319 | 1.00 | 0.00 |
| ATOM | 192 | N | PRO | 1 | 25 | 6.264 | 35.552 | 27.463 | 1.00 | 0.00 |
| ATOM | 193 | CA | PRO | 1 | 25 | 7.528 | 36.069 | 27.834 | 1.00 | 0.00 |
| ATOM | 194 | C | PRO | 1 | 25 | 7.954 | 37.302 | 27.064 | 1.00 | 0.00 |
| ATOM | 195 | O | PRO | 1 | 25 | 7.102 | 37.967 | 26.519 | 1.00 | 0.00 |
| ATOM | 196 | CB | PRO | 1 | 25 | 8.536 | 34.960 | 27.498 | 1.00 | 0.00 |
| ATOM | 197 | CG | PRO | 1 | 25 | 7.766 | 33.902 | 26.624 | 1.00 | 0.00 |
| ATOM | 198 | CD | PRO | 1 | 25 | 6.327 | 34.297 | 26.774 | 1.00 | 0.00 |
| ATOM | 199 | N | VAL | 1 | 26 | 9.251 | 37.652 | 27.070 | 1.00 | 0.00 |
| ATOM | 200 | CA | VAL | 1 | 26 | 9.831 | 38.466 | 25.975 | 1.00 | 0.00 |
| ATOM | 201 | C | VAL | 1 | 26 | 10.054 | 37.488 | 24.900 | 1.00 | 0.00 |
| ATOM | 202 | O | VAL | 1 | 26 | 9.071 | 36.906 | 24.424 | 1.00 | 0.00 |
| ATOM | 203 | CB | VAL | 1 | 26 | 11.032 | 39.240 | 26.509 | 1.00 | 0.00 |
| ATOM | 204 | CG1 | VAL | 1 | 26 | 10.726 | 40.772 | 26.799 | 1.00 | 0.00 |
| ATOM | 205 | CG2 | VAL | 1 | 26 | 11.723 | 38.692 | 27.823 | 1.00 | 0.00 |
| ATOM | 206 | H | VAL | 1 | 26 | 9.681 | 37.030 | 27.724 | 1.00 | 0.00 |
| ATOM | 207 | N | GLY | 1 | 27 | 11.292 | 37.168 | 24.590 | 1.00 | 0.00 |
| ATOM | 208 | CA | GLY | 1 | 27 | 11.482 | 35.738 | 24.271 | 1.00 | 0.00 |
| ATOM | 209 | C | GLY | 1 | 27 | 11.647 | 34.818 | 25.477 | 1.00 | 0.00 |
| ATOM | 210 | O | GLY | 1 | 27 | 11.513 | 35.432 | 26.503 | 1.00 | 0.00 |
| ATOM | 211 | H | GLY | 1 | 27 | 12.099 | 37.604 | 24.988 | 1.00 | 0.00 |
| ATOM | 212 | N | ASP | 1 | 28 | 12.041 | 33.489 | 25.391 | 1.00 | 0.00 |
| ATOM | 213 | CA | ASP | 1 | 28 | 12.052 | 32.693 | 26.625 | 1.00 | 0.00 |
| ATOM | 214 | C | ASP | 1 | 28 | 12.264 | 33.254 | 28.042 | 1.00 | 0.00 |
| ATOM | 215 | O | ASP | 1 | 28 | 11.812 | 32.613 | 29.013 | 1.00 | 0.00 |
| ATOM | 216 | CB | ASP | 1 | 28 | 12.848 | 31.459 | 26.313 | 1.00 | 0.00 |
| ATOM | 217 | CG | ASP | 1 | 28 | 12.220 | 30.275 | 26.971 | 1.00 | 0.00 |
| ATOM | 218 | OD1 | ASP | 1 | 28 | 11.048 | 29.929 | 26.718 | 1.00 | 0.00 |
| ATOM | 219 | OD2 | ASP | 1 | 28 | 12.910 | 29.622 | 27.780 | 1.00 | 0.00 |
| ATOM | 220 | H | ASP | 1 | 28 | 12.089 | 33.023 | 24.507 | 1.00 | 0.00 |
| ATOM | 221 | N | ASP | 1 | 29 | 13.052 | 34.361 | 28.176 | 1.00 | 0.00 |
| ATOM | 222 | CA | ASP | 1 | 29 | 13.109 | 34.931 | 29.560 | 1.00 | 0.00 |
| ATOM | 223 | C | ASP | 1 | 29 | 11.716 | 35.121 | 30.289 | 1.00 | 0.00 |
| ATOM | 224 | O | ASP | 1 | 29 | 10.664 | 35.488 | 29.732 | 1.00 | 0.00 |
| ATOM | 225 | CB | ASP | 1 | 29 | 14.006 | 36.222 | 29.650 | 1.00 | 0.00 |

FIG. 1E

| ATOM | 226 | CG | ASP | 1 | 29 | 13.724 | 37.078 | 30.916 | 1.00 | 0.00 |
| --- | --- | --- | --- | --- | --- | --- | --- | --- | --- | --- |
| ATOM | 227 | OD1 | ASP | 1 | 29 | 13.034 | 38.080 | 30.842 | 1.00 | 0.00 |
| ATOM | 228 | OD2 | ASP | 1 | 29 | 14.208 | 36.708 | 31.973 | 1.00 | 0.00 |
| ATOM | 229 | H | ASP | 1 | 29 | 13.367 | 34.766 | 27.317 | 1.00 | 0.00 |
| ATOM | 230 | N | MET | 1 | 30 | 11.742 | 34.874 | 31.593 | 1.00 | 0.00 |
| ATOM | 231 | CA | MET | 1 | 30 | 10.513 | 34.871 | 32.347 | 1.00 | 0.00 |
| ATOM | 232 | C | MET | 1 | 30 | 10.424 | 35.967 | 33.348 | 1.00 | 0.00 |
| ATOM | 233 | O | MET | 1 | 30 | 9.395 | 36.073 | 34.009 | 1.00 | 0.00 |
| ATOM | 234 | CB | MET | 1 | 30 | 10.024 | 33.562 | 32.904 | 1.00 | 0.00 |
| ATOM | 235 | CG | MET | 1 | 30 | 8.608 | 33.344 | 32.660 | 1.00 | 0.00 |
| ATOM | 236 | SD | MET | 1 | 30 | 8.121 | 33.393 | 30.892 | 1.00 | 0.00 |
| ATOM | 237 | CE | MET | 1 | 30 | 6.473 | 32.740 | 31.116 | 1.00 | 0.00 |
| ATOM | 238 | H | MET | 1 | 30 | 12.645 | 34.898 | 32.021 | 1.00 | 0.00 |
| ATOM | 239 | N | PHE | 1 | 31 | 11.476 | 36.831 | 33.387 | 1.00 | 0.00 |
| ATOM | 240 | CA | PHE | 1 | 31 | 11.426 | 37.966 | 34.248 | 1.00 | 0.00 |
| ATOM | 241 | C | PHE | 1 | 31 | 10.748 | 39.124 | 33.639 | 1.00 | 0.00 |
| ATOM | 242 | O | PHE | 1 | 31 | 10.171 | 39.983 | 34.265 | 1.00 | 0.00 |
| ATOM | 243 | CB | PHE | 1 | 31 | 12.847 | 38.280 | 34.753 | 1.00 | 0.00 |
| ATOM | 244 | CG | PHE | 1 | 31 | 13.502 | 36.936 | 35.115 | 1.00 | 0.00 |
| ATOM | 245 | CD1 | PHE | 1 | 31 | 14.835 | 36.780 | 34.734 | 1.00 | 0.00 |
| ATOM | 246 | CD2 | PHE | 1 | 31 | 12.856 | 35.900 | 35.819 | 1.00 | 0.00 |
| ATOM | 247 | CE1 | PHE | 1 | 31 | 15.477 | 35.585 | 34.972 | 1.00 | 0.00 |
| ATOM | 248 | CE2 | PHE | 1 | 31 | 13.540 | 34.632 | 36.102 | 1.00 | 0.00 |
| ATOM | 249 | CZ | PHE | 1 | 31 | 14.843 | 34.454 | 35.587 | 1.00 | 0.00 |
| ATOM | 250 | H | PHE | 1 | 31 | 12.277 | 36.803 | 32.788 | 1.00 | 0.00 |
| ATOM | 251 | N | HIS | 1 | 32 | 10.865 | 39.200 | 32.331 | 1.00 | 0.00 |
| ATOM | 252 | CA | HIS | 1 | 32 | 9.972 | 40.079 | 31.653 | 1.00 | 0.00 |
| ATOM | 253 | C | HIS | 1 | 32 | 8.924 | 39.415 | 30.769 | 1.00 | 0.00 |
| ATOM | 254 | O | HIS | 1 | 32 | 9.202 | 38.493 | 30.018 | 1.00 | 0.00 |
| ATOM | 255 | CB | HIS | 1 | 32 | 10.760 | 41.083 | 30.810 | 1.00 | 0.00 |
| ATOM | 256 | CG | HIS | 1 | 32 | 10.498 | 42.477 | 31.288 | 1.00 | 0.00 |
| ATOM | 257 | ND1 | HIS | 1 | 32 | 11.346 | 43.479 | 31.266 | 1.00 | 0.00 |
| ATOM | 258 | CD2 | HIS | 1 | 32 | 9.246 | 43.049 | 31.602 | 1.00 | 0.00 |
| ATOM | 259 | CE1 | HIS | 1 | 32 | 10.678 | 44.659 | 31.574 | 1.00 | 0.00 |
| ATOM | 260 | NE1 | HIS | 1 | 32 | 9.377 | 44.389 | 31.784 | 1.00 | 0.00 |
| ATOM | 261 | H | HIS | 1 | 32 | 11.489 | 38.555 | 31.889 | 1.00 | 0.00 |
| ATOM | 262 | 1HD | HIS | 1 | 32 | 12.295 | 43.246 | 31.197 | 1.00 | 0.00 |
| ATOM | 263 | N | TRP | 1 | 33 | 7.790 | 39.969 | 30.994 | 1.00 | 0.00 |
| ATOM | 264 | CA | TRP | 1 | 33 | 6.604 | 39.493 | 30.279 | 1.00 | 0.00 |
| ATOM | 265 | C | TRP | 1 | 33 | 6.205 | 40.551 | 29.240 | 1.00 | 0.00 |
| ATOM | 266 | O | TRP | 1 | 33 | 6.438 | 41.689 | 29.500 | 1.00 | 0.00 |
| ATOM | 267 | CB | TRP | 1 | 33 | 5.415 | 39.260 | 31.209 | 1.00 | 0.00 |
| ATOM | 268 | CG | TRP | 1 | 33 | 5.641 | 38.164 | 32.176 | 1.00 | 0.00 |
| ATOM | 269 | CD1 | TRP | 1 | 33 | 6.812 | 37.983 | 32.936 | 1.00 | 0.00 |
| ATOM | 270 | CD2 | TRP | 1 | 33 | 4.801 | 37.018 | 32.425 | 1.00 | 0.00 |

FIG. 1F

| ATOM | 271 | NE1 | TRP | 1 | 33 | 6.752 | 36.776 | 33.576 | 1.00 | 0.00 |
| ATOM | 272 | CE2 | TRP | 1 | 33 | 5.536 | 36.139 | 33.304 | 1.00 | 0.00 |
| ATOM | 273 | CE3 | TRP | 1 | 33 | 3.526 | 36.671 | 31.930 | 1.00 | 0.00 |
| ATOM | 274 | CZ2 | TRP | 1 | 33 | 5.043 | 34.854 | 33.676 | 1.00 | 0.00 |
| ATOM | 275 | CZ3 | TRP | 1 | 33 | 3.036 | 35.429 | 32.346 | 1.00 | 0.00 |
| ATOM | 276 | CH2 | TRP | 1 | 33 | 3.758 | 34.524 | 33.185 | 1.00 | 0.00 |
| ATOM | 277 | H | TRP | 1 | 33 | 7.826 | 40.663 | 31.713 | 1.00 | 0.00 |
| ATOM | 278 | 1HE | TRP | 1 | 33 | 7.482 | 36.492 | 34.165 | 1.00 | 0.00 |
| ATOM | 279 | N | GLN | 1 | 34 | 5.696 | 40.048 | 28.134 | 1.00 | 0.00 |
| ATOM | 280 | CA | GLN | 1 | 34 | 4.869 | 40.836 | 27.220 | 1.00 | 0.00 |
| ATOM | 281 | C | GLN | 1 | 34 | 3.424 | 40.408 | 27.177 | 1.00 | 0.00 |
| ATOM | 282 | O | GLN | 1 | 34 | 3.094 | 39.240 | 27.133 | 1.00 | 0.00 |
| ATOM | 283 | CB | GLN | 1 | 34 | 5.470 | 40.924 | 25.800 | 1.00 | 0.00 |
| ATOM | 284 | CG | GLN | 1 | 34 | 6.917 | 41.448 | 25.783 | 1.00 | 0.00 |
| ATOM | 285 | CD | GLN | 1 | 34 | 7.429 | 41.452 | 24.291 | 1.00 | 0.00 |
| ATOM | 286 | OE1 | GLN | 1 | 34 | 7.612 | 42.380 | 23.559 | 1.00 | 0.00 |
| ATOM | 287 | NE1 | GLN | 1 | 34 | 7.489 | 40.260 | 23.927 | 1.00 | 0.00 |
| ATOM | 288 | H | GLN | 1 | 34 | 5.517 | 39.064 | 28.146 | 1.00 | 0.00 |
| ATOM | 289 | 1HE2 | GLN | 1 | 34 | 7.323 | 39.442 | 24.478 | 1.00 | 0.00 |
| ATOM | 290 | 2HE2 | GLN | 1 | 34 | 7.792 | 40.263 | 22.974 | 1.00 | 0.00 |
| ATOM | 291 | N | ALA | 1 | 35 | 2.538 | 41.366 | 27.220 | 1.00 | 0.00 |
| ATOM | 292 | CA | ALA | 1 | 35 | 1.184 | 40.851 | 27.117 | 1.00 | 0.00 |
| ATOM | 293 | C | ALA | 1 | 35 | 0.289 | 41.720 | 26.273 | 1.00 | 0.00 |
| ATOM | 294 | O | ALA | 1 | 35 | 0.110 | 42.908 | 26.564 | 1.00 | 0.00 |
| ATOM | 295 | CB | ALA | 1 | 35 | 0.621 | 40.755 | 28.550 | 1.00 | 0.00 |
| ATOM | 296 | H | ALA | 1 | 35 | 2.893 | 42.286 | 27.389 | 1.00 | 0.00 |
| ATOM | 297 | N | THR | 1 | 36 | -0.357 | 40.970 | 25.395 | 1.00 | 0.00 |
| ATOM | 298 | CA | THR | 1 | 36 | -1.550 | 41.487 | 24.753 | 1.00 | 0.00 |
| ATOM | 299 | C | THR | 1 | 36 | -2.696 | 41.829 | 25.712 | 1.00 | 0.00 |
| ATOM | 300 | O | THR | 1 | 36 | -3.280 | 41.022 | 26.401 | 1.00 | 0.00 |
| ATOM | 301 | CB | THR | 1 | 36 | -2.200 | 40.523 | 23.714 | 1.00 | 0.00 |
| ATOM | 302 | OG1 | THR | 1 | 36 | -1.176 | 39.765 | 22.985 | 1.00 | 0.00 |
| ATOM | 303 | CG2 | THR | 1 | 36 | -3.302 | 41.301 | 22.943 | 1.00 | 0.00 |
| ATOM | 304 | H | THR | 1 | 36 | 0.086 | 40.113 | 25.129 | 1.00 | 0.00 |
| ATOM | 305 | 1HG | THR | 1 | 36 | -1.335 | 40.089 | 22.109 | 1.00 | 0.00 |
| ATOM | 306 | N | ILE | 1 | 37 | -3.026 | 43.130 | 25.648 | 1.00 | 0.00 |
| ATOM | 307 | CA | ILE | 1 | 37 | -4.191 | 43.548 | 26.429 | 1.00 | 0.00 |
| ATOM | 308 | C | ILE | 1 | 37 | -5.298 | 44.216 | 25.630 | 1.00 | 0.00 |
| ATOM | 309 | O | ILE | 1 | 37 | -5.101 | 45.204 | 24.964 | 1.00 | 0.00 |
| ATOM | 310 | CB | ILE | 1 | 37 | -3.797 | 44.351 | 27.724 | 1.00 | 0.00 |
| ATOM | 311 | CG1 | ILE | 1 | 37 | -4.897 | 45.181 | 28.449 | 1.00 | 0.00 |
| ATOM | 312 | CG2 | ILE | 1 | 37 | -2.542 | 45.130 | 27.448 | 1.00 | 0.00 |
| ATOM | 313 | CD1 | ILE | 1 | 37 | -4.556 | 46.013 | 29.659 | 1.00 | 0.00 |
| ATOM | 314 | H | ILE | 1 | 37 | -2.472 | 43.740 | 25.081 | 1.00 | 0.00 |
| ATOM | 315 | N | ILE | 1 | 37 | -6.458 | 43.574 | 25.878 | 1.00 | 0.00 |

FIG. 1G

| ATOM | 316 | CA | MET | 1 | 38 | -7.586 | 44.220 | 25.347 | 1.00 | 0.00 |
| ATOM | 317 | C | MET | 1 | 38 | 8.605 | 44.872 | 26.322 | 1.00 | 0.00 |
| ATOM | 318 | O | MET | 1 | 38 | -8.349 | 45.935 | 26.893 | 1.00 | 0.00 |
| ATOM | 319 | CB | MET | 1 | 38 | -8.343 | 43.241 | 24.447 | 1.00 | 0.00 |
| ATOM | 320 | CG | MET | 1 | 38 | -7.470 | 42.311 | 23.603 | 1.00 | 0.00 |
| ATOM | 321 | SD | MET | 1 | 38 | -8.288 | 40.905 | 22.853 | 1.00 | 0.00 |
| ATOM | 322 | CE | MET | 1 | 38 | -9.622 | 41.838 | 22.065 | 1.00 | 0.00 |
| ATOM | 323 | H | MET | 1 | 38 | 6.505 | 42.757 | 26.452 | 1.00 | 0.00 |
| ATOM | 324 | N | GLY | 1 | 39 | -9.770 | 44.272 | 26.496 | 1.00 | 0.00 |
| ATOM | 325 | CA | GLY | 1 | 39 | -11.056 | 44.966 | 26.850 | 1.00 | 0.00 |
| ATOM | 326 | C | GLY | 1 | 39 | -12.298 | 44.411 | 26.038 | 1.00 | 0.00 |
| ATOM | 327 | O | GLY | 1 | 39 | -12.214 | 43.940 | 24.916 | 1.00 | 0.00 |
| ATOM | 328 | H | GLY | 1 | 39 | -9.966 | 43.294 | 26.425 | 1.00 | 0.00 |
| ATOM | 329 | N | PRO | 1 | 40 | -13.477 | 44.500 | 26.766 | 1.00 | 0.00 |
| ATOM | 330 | CA | PRO | 1 | 40 | -14.704 | 43.852 | 26.332 | 1.00 | 0.00 |
| ATOM | 331 | C | PRO | 1 | 40 | -15.431 | 44.406 | 25.096 | 1.00 | 0.00 |
| ATOM | 332 | O | PRO | 1 | 40 | -15.378 | 45.605 | 24.835 | 1.00 | 0.00 |
| ATOM | 333 | CG | PRO | 1 | 40 | -15.528 | 43.836 | 27.644 | 1.00 | 0.00 |
| ATOM | 334 | CG | PRO | 1 | 40 | -15.102 | 45.100 | 28.414 | 1.00 | 0.00 |
| ATOM | 335 | CD | PRO | 1 | 40 | -13.575 | 45.060 | 28.122 | 1.00 | 0.00 |
| ATOM | 336 | N | ASN | 1 | 41 | -16.104 | 43.478 | 24.432 | 1.00 | 0.00 |
| ATOM | 337 | CA | ASN | 1 | 41 | -16.866 | 43.806 | 23.227 | 1.00 | 0.00 |
| ATOM | 338 | C | ASN | 1 | 41 | -17.788 | 45.030 | 23.243 | 1.00 | 0.00 |
| ATOM | 339 | O | ASN | 1 | 41 | -18.334 | 45.404 | 24.266 | 1.00 | 0.00 |
| ATOM | 340 | CB | ASN | 1 | 41 | -17.505 | 42.566 | 22.629 | 1.00 | 0.00 |
| ATOM | 341 | CG | ASN | 1 | 41 | -17.457 | 42.783 | 21.100 | 1.00 | 0.00 |
| ATOM | 342 | OD1 | ASN | 1 | 41 | -16.424 | 42.515 | 20.518 | 1.00 | 0.00 |
| ATOM | 343 | ND2 | ASN | 1 | 41 | -18.580 | 43.205 | 20.495 | 1.00 | 0.00 |
| ATOM | 344 | H | ASN | 1 | 41 | -16.031 | 42.509 | 24.671 | 1.00 | 0.00 |
| ATOM | 345 | 1HD2 | ASN | 1 | 41 | -19.340 | 43.519 | 21.065 | 1.00 | 0.00 |
| ATOM | 346 | 2HD2 | ASN | 1 | 41 | -18.839 | 43.307 | 19.534 | 1.00 | 0.00 |
| ATOM | 347 | N | ASP | 1 | 42 | -17.706 | 45.666 | 22.075 | 1.00 | 0.00 |
| ATOM | 348 | CA | ASP | 1 | 42 | -18.549 | 46.827 | 21.646 | 1.00 | 0.00 |
| ATOM | 349 | C | ASP | 1 | 42 | -17.990 | 48.094 | 22.183 | 1.00 | 0.00 |
| ATOM | 350 | O | ASP | 1 | 42 | -17.904 | 49.099 | 21.503 | 1.00 | 0.00 |
| ATOM | 351 | CB | ASP | 1 | 42 | -20.049 | 46.643 | 22.001 | 1.00 | 0.00 |
| ATOM | 352 | CG | ASP | 1 | 42 | -20.617 | 45.386 | 21.248 | 1.00 | 0.00 |
| ATOM | 353 | OD1 | ASP | 1 | 42 | -21.189 | 44.546 | 22.019 | 1.00 | 0.00 |
| ATOM | 354 | OD2 | ASP | 1 | 42 | -20.505 | 45.329 | 19.972 | 1.00 | 0.00 |
| ATOM | 355 | H | ASP | 1 | 42 | -17.172 | 45.239 | 21.345 | 1.00 | 0.00 |
| ATOM | 356 | N | SER | 1 | 43 | -17.518 | 47.956 | 23.425 | 1.00 | 0.00 |
| ATOM | 357 | CA | SER | 1 | 43 | -16.981 | 49.076 | 24.283 | 1.00 | 0.00 |
| ATOM | 358 | C | SER | 1 | 43 | -15.645 | 49.654 | 23.703 | 1.00 | 0.00 |
| ATOM | 359 | O | SER | 1 | 43 | -14.885 | 49.017 | 22.898 | 1.00 | 0.00 |
| ATOM | 360 | CB | SER | 1 | 43 | -16.864 | 48.550 | 25.721 | 1.00 | 0.00 |

FIG. 1H

| | | | | | | | | | |
|---|---|---|---|---|---|---|---|---|---|
| ATOM | 361 | OG | SER | 1 | 43 | -17.907 | 47.578 | 25.969 | 1.00 0.00 |
| ATOM | 362 | H | SER | 1 | 43 | -17.691 | 47.082 | 23.879 | 1.00 0.00 |
| ATOM | 363 | HG | SER | 1 | 43 | -17.668 | 46.770 | 25.535 | 1.00 0.00 |
| ATOM | 364 | N | PRO | 1 | 43 | -15.449 | 50.978 | 24.037 | 1.00 0.00 |
| ATOM | 365 | CA | PRO | 1 | 44 | -14.337 | 51.686 | 23.444 | 1.00 0.00 |
| ATOM | 366 | C | PRO | 1 | 44 | -12.965 | 51.042 | 23.266 | 1.00 0.00 |
| ATOM | 367 | O | PRO | 1 | 44 | -12.323 | 50.986 | 22.187 | 1.00 0.00 |
| ATOM | 368 | CB | PRO | 1 | 44 | -14.294 | 52.931 | 24.332 | 1.00 0.00 |
| ATOM | 369 | CG | PRO | 1 | 44 | -15.749 | 53.253 | 24.642 | 1.00 0.00 |
| ATOM | 370 | CD | PRO | 1 | 44 | -16.388 | 51.873 | 24.723 | 1.00 0.00 |
| ATOM | 371 | N | TYR | 1 | 45 | -12.499 | 50.612 | 24.469 | 1.00 0.00 |
| ATOM | 372 | CA | TYR | 1 | 45 | -11.173 | 49.936 | 24.432 | 1.00 0.00 |
| ATOM | 373 | C | TYR | 1 | 45 | -10.989 | 48.618 | 23.768 | 1.00 0.00 |
| ATOM | 374 | O | TYR | 1 | 45 | -9.874 | 48.082 | 23.625 | 1.00 0.00 |
| ATOM | 375 | CB | TYR | 1 | 45 | -10.642 | 49.821 | 25.898 | 1.00 0.00 |
| ATOM | 376 | CG | TYR | 1 | 45 | -10.263 | 51.093 | 26.551 | 1.00 0.00 |
| ATOM | 377 | CD1 | TYR | 1 | 45 | -11.055 | 51.437 | 27.637 | 1.00 0.00 |
| ATOM | 378 | CD2 | TYR | 1 | 45 | -9.186 | 51.866 | 26.062 | 1.00 0.00 |
| ATOM | 379 | CE1 | TYR | 1 | 45 | -10.678 | 52.632 | 28.338 | 1.00 0.00 |
| ATOM | 380 | CE2 | TYR | 1 | 45 | -8.954 | 53.120 | 26.707 | 1.00 0.00 |
| ATOM | 381 | CZ | TYR | 1 | 45 | -9.696 | 53.503 | 27.827 | 1.00 0.00 |
| ATOM | 382 | OH | TYR | 1 | 45 | -9.427 | 54.731 | 28.452 | 1.00 0.00 |
| ATOM | 383 | H | TYR | 1 | 45 | -12.786 | 50.950 | 25.365 | 1.00 0.00 |
| ATOM | 384 | HH | TYR | 1 | 45 | -9.015 | 55.269 | 27.788 | 1.00 0.00 |
| ATOM | 385 | N | GLN | 1 | 46 | -12.094 | 48.046 | 23.382 | 1.00 0.00 |
| ATOM | 386 | CA | GLN | 1 | 46 | -12.061 | 46.725 | 22.755 | 1.00 0.00 |
| ATOM | 387 | C | GLN | 1 | 46 | -11.454 | 46.729 | 21.459 | 1.00 0.00 |
| ATOM | 388 | O | GLN | 1 | 46 | -11.537 | 47.737 | 20.760 | 1.00 0.00 |
| ATOM | 389 | CB | GLN | 1 | 46 | -13.469 | 46.126 | 22.604 | 1.00 0.00 |
| ATOM | 390 | CG | GLN | 1 | 46 | -13.789 | 45.049 | 21.539 | 1.00 0.00 |
| ATOM | 391 | CD | GLN | 1 | 46 | -14.461 | 45.627 | 20.354 | 1.00 0.00 |
| ATOM | 392 | OE1 | GLN | 1 | 46 | -14.289 | 46.795 | 20.051 | 1.00 0.00 |
| ATOM | 393 | NE2 | GLN | 1 | 46 | -15.311 | 44.856 | 19.671 | 1.00 0.00 |
| ATOM | 394 | H | GLN | 1 | 46 | -12.898 | 48.611 | 23.201 | 1.00 0.00 |
| ATOM | 395 | 1HE2 | GLN | 1 | 46 | -15.436 | 43.884 | 19.867 | 1.00 0.00 |
| ATOM | 396 | 2HE2 | GLN | 1 | 46 | -15.796 | 45.251 | 18.890 | 1.00 0.00 |
| ATOM | 397 | N | GLY | 1 | 47 | -10.734 | 45.644 | 21.155 | 1.00 0.00 |
| ATOM | 398 | CA | GLY | 1 | 47 | -10.114 | 45.605 | 19.848 | 1.00 0.00 |
| ATOM | 399 | C | GLY | 1 | 47 | -8.629 | 45.843 | 19.905 | 1.00 0.00 |
| ATOM | 400 | O | GLY | 1 | 47 | -7.769 | 45.119 | 19.319 | 1.00 0.00 |
| ATOM | 401 | H | GLY | 1 | 47 | -10.775 | 44.822 | 21.723 | 1.00 0.00 |
| ATOM | 402 | N | GLY | 1 | 48 | -8.271 | 46.947 | 20.695 | 1.00 0.00 |
| ATOM | 403 | CA | GLY | 1 | 48 | -6.913 | 47.393 | 20.950 | 1.00 0.00 |
| ATOM | 404 | C | GLY | 1 | 48 | -6.009 | 46.228 | 21.154 | 1.00 0.00 |
| ATOM | 405 | O | GLY | 1 | 48 | -6.280 | 45.269 | 21.911 | 1.00 0.00 |

FIG. 1I

| ATOM | 406 | H | GLY | 1 | 48 | -9.072 | 47.442 | 21.032 | 1.00 | 0.00 |
|------|-----|-----|-----|---|----|--------|--------|--------|------|------|
| ATOM | 407 | N | VAL | 1 | 49 | -4.877 | 46.300 | 20.420 | 1.00 | 0.00 |
| ATOM | 408 | CA | VAL | 1 | 49 | -3.846 | 45.346 | 20.774 | 1.00 | 0.00 |
| ATOM | 409 | C | VAL | 1 | 49 | -2.700 | 46.129 | 21.429 | 1.00 | 0.00 |
| ATOM | 410 | O | VAL | 1 | 49 | -1.856 | 46.847 | 20.841 | 1.00 | 0.00 |
| ATOM | 411 | CB | VAL | 1 | 49 | -3.358 | 44.738 | 19.453 | 1.00 | 0.00 |
| ATOM | 412 | CG1 | VAL | 1 | 49 | -2.394 | 43.577 | 19.728 | 1.00 | 0.00 |
| ATOM | 413 | CG2 | VAL | 1 | 49 | -4.498 | 44.517 | 18.390 | 1.00 | 0.00 |
| ATOM | 414 | H | VAL | 1 | 49 | -4.707 | 47.023 | 19.750 | 1.00 | 0.00 |
| ATOM | 415 | N | PHE | 1 | 50 | -2.811 | 46.022 | 22.734 | 1.00 | 0.00 |
| ATOM | 416 | CA | PHE | 1 | 50 | -1.793 | 46.690 | 23.383 | 1.00 | 0.00 |
| ATOM | 417 | C | PHE | 1 | 50 | -0.835 | 45.766 | 23.937 | 1.00 | 0.00 |
| ATOM | 418 | O | PHE | 1 | 50 | -1.082 | 44.564 | 24.001 | 1.00 | 0.00 |
| ATOM | 419 | CB | PHE | 1 | 50 | -2.343 | 47.588 | 24.462 | 1.00 | 0.00 |
| ATOM | 420 | CG | PHE | 1 | 50 | -3.767 | 48.162 | 24.266 | 1.00 | 0.00 |
| ATOM | 421 | CD1 | PHE | 1 | 50 | -4.158 | 48.819 | 23.058 | 1.00 | 0.00 |
| ATOM | 422 | CD2 | PHE | 1 | 50 | -4.648 | 48.064 | 25.365 | 1.00 | 0.00 |
| ATOM | 423 | CE1 | PHE | 1 | 50 | -5.442 | 49.326 | 22.959 | 1.00 | 0.00 |
| ATOM | 424 | CE2 | PHE | 1 | 50 | -5.989 | 48.477 | 25.179 | 1.00 | 0.00 |
| ATOM | 425 | CZ | PHE | 1 | 50 | -6.378 | 49.138 | 23.978 | 1.00 | 0.00 |
| ATOM | 426 | H | PHE | 1 | 50 | -3.535 | 45.534 | 23.221 | 1.00 | 0.00 |
| ATOM | 427 | N | PHE | 1 | 51 | 0.269 | 46.369 | 24.384 | 1.00 | 0.00 |
| ATOM | 428 | CA | PHE | 1 | 51 | 1.219 | 45.510 | 25.011 | 1.00 | 0.00 |
| ATOM | 429 | C | PHE | 1 | 51 | 1.628 | 46.101 | 26.372 | 1.00 | 0.00 |
| ATOM | 430 | O | PHE | 1 | 51 | 1.290 | 47.244 | 26.681 | 1.00 | 0.00 |
| ATOM | 431 | CB | PHE | 1 | 51 | 2.558 | 45.235 | 24.183 | 1.00 | 0.00 |
| ATOM | 432 | CG | PHE | 1 | 51 | 2.071 | 44.870 | 22.735 | 1.00 | 0.00 |
| ATOM | 433 | CD1 | PHE | 1 | 51 | 1.474 | 43.648 | 22.482 | 1.00 | 0.00 |
| ATOM | 434 | CD2 | PHE | 1 | 51 | 2.253 | 45.869 | 21.762 | 1.00 | 0.00 |
| ATOM | 435 | CE1 | PHE | 1 | 51 | 1.003 | 43.443 | 21.104 | 1.00 | 0.00 |
| ATOM | 436 | CE2 | PHE | 1 | 51 | 1.858 | 45.668 | 20.423 | 1.00 | 0.00 |
| ATOM | 437 | CZ | PHE | 1 | 51 | 1.236 | 44.497 | 20.130 | 1.00 | 0.00 |
| ATOM | 438 | H | PHE | 1 | 51 | 0.598 | 47.248 | 24.040 | 1.00 | 0.00 |
| ATOM | 439 | N | LEU | 1 | 52 | 2.130 | 45.091 | 27.132 | 1.00 | 0.00 |
| ATOM | 440 | CA | LEU | 1 | 52 | 2.325 | 45.227 | 28.576 | 1.00 | 0.00 |
| ATOM | 441 | C | LEU | 1 | 52 | 3.524 | 44.445 | 29.054 | 1.00 | 0.00 |
| ATOM | 442 | O | LEU | 1 | 52 | 3.530 | 43.203 | 29.019 | 1.00 | 0.00 |
| ATOM | 443 | CB | LEU | 1 | 52 | 1.065 | 44.789 | 29.287 | 1.00 | 0.00 |
| ATOM | 444 | CG | LEU | 1 | 52 | 0.938 | 45.233 | 30.789 | 1.00 | 0.00 |
| ATOM | 445 | CD1 | LEU | 1 | 52 | -0.220 | 46.185 | 30.933 | 1.00 | 0.00 |
| ATOM | 446 | CD2 | LEU | 1 | 52 | 0.653 | 44.204 | 31.814 | 1.00 | 0.00 |
| ATOM | 447 | H | LEU | 1 | 52 | 2.068 | 44.177 | 26.732 | 1.00 | 0.00 |
| ATOM | 448 | N | THR | 1 | 53 | 4.567 | 45.174 | 29.416 | 1.00 | 0.00 |
| ATOM | 449 | CA | THR | 1 | 53 | 5.541 | 44.339 | 30.004 | 1.00 | 0.00 |
| ATOM | 450 | C | THR | 1 | 53 | 5.394 | 44.249 | 31.552 | 1.00 | 0.00 |

FIG. 1J

| ATOM | 451 | O | THR | 1 | 53 | 5.698 | 45.208 | 32.281 | 1.00 | 0.00 |
| ATOM | 452 | CB | THR | 1 | 53 | 6.993 | 44.839 | 29.721 | 1.00 | 0.00 |
| ATOM | 453 | OG1 | THR | 1 | 53 | 7.141 | 46.178 | 30.117 | 1.00 | 0.00 |
| ATOM | 454 | OG2 | THR | 1 | 53 | 7.449 | 44.539 | 28.336 | 1.00 | 0.00 |
| ATOM | 455 | H | THR | 1 | 53 | 4.610 | 46.165 | 29.290 | 1.00 | 0.00 |
| ATOM | 456 | 1HG | THR | 1 | 53 | 6.693 | 46.593 | 29.392 | 1.00 | 0.00 |
| ATOM | 457 | N | ILE | 1 | 54 | 5.055 | 43.019 | 32.006 | 1.00 | 0.00 |
| ATOM | 458 | CA | ILE | 1 | 54 | 5.201 | 42.975 | 33.500 | 1.00 | 0.00 |
| ATOM | 459 | C | ILE | 1 | 54 | 6.483 | 42.187 | 33.824 | 1.00 | 0.00 |
| ATOM | 460 | O | ILE | 1 | 54 | 6.624 | 41.049 | 33.449 | 1.00 | 0.00 |
| ATOM | 461 | CB | ILE | 1 | 54 | 3.895 | 42.546 | 34.056 | 1.00 | 0.00 |
| ATOM | 462 | CG1 | ILE | 1 | 54 | 4.116 | 42.239 | 35.538 | 1.00 | 0.00 |
| ATOM | 463 | CG2 | ILE | 1 | 54 | 3.293 | 41.330 | 33.449 | 1.00 | 0.00 |
| ATOM | 464 | CD1 | ILE | 1 | 54 | 2.835 | 42.116 | 36.297 | 1.00 | 0.00 |
| ATOM | 465 | H | ILE | 1 | 54 | 4.883 | 42.200 | 31.459 | 1.00 | 0.00 |
| ATOM | 466 | N | HIS | 1 | 55 | 7.356 | 42.905 | 34.533 | 1.00 | 0.00 |
| ATOM | 467 | CA | HIS | 1 | 55 | 8.680 | 42.432 | 35.034 | 1.00 | 0.00 |
| ATOM | 468 | C | HIS | 1 | 55 | 8.488 | 41.851 | 36.430 | 1.00 | 0.00 |
| ATOM | 469 | O | HIS | 1 | 55 | 8.711 | 42.401 | 37.499 | 1.00 | 0.00 |
| ATOM | 470 | CB | HIS | 1 | 55 | 9.677 | 43.626 | 35.221 | 1.00 | 0.00 |
| ATOM | 471 | CG | HIS | 1 | 55 | 11.084 | 43.145 | 35.610 | 1.00 | 0.00 |
| ATOM | 472 | ND1 | HIS | 1 | 55 | 11.463 | 42.849 | 36.889 | 1.00 | 0.00 |
| ATOM | 473 | CD2 | HIS | 1 | 55 | 12.160 | 43.008 | 34.734 | 1.00 | 0.00 |
| ATOM | 474 | CE1 | HIS | 1 | 55 | 12.798 | 42.553 | 36.874 | 1.00 | 0.00 |
| ATOM | 475 | NE2 | HIS | 1 | 55 | 13.166 | 42.652 | 35.589 | 1.00 | 0.00 |
| ATOM | 476 | H | HIS | 1 | 55 | 6.985 | 43.825 | 34.656 | 1.00 | 0.00 |
| ATOM | 477 | 1HD | HIS | 1 | 55 | 10.779 | 42.792 | 37.588 | 1.00 | 0.00 |
| ATOM | 478 | N | PHE | 1 | 56 | 8.004 | 40.579 | 36.294 | 1.00 | 0.00 |
| ATOM | 479 | CA | PHE | 1 | 56 | 8.124 | 39.740 | 37.478 | 1.00 | 0.00 |
| ATOM | 480 | C | PHE | 1 | 56 | 9.564 | 39.404 | 37.759 | 1.00 | 0.00 |
| ATOM | 481 | O | PHE | 1 | 56 | 10.111 | 38.735 | 36.928 | 1.00 | 0.00 |
| ATOM | 482 | CB | PHE | 1 | 56 | 7.431 | 38.414 | 37.221 | 1.00 | 0.00 |
| ATOM | 483 | CG | PHE | 1 | 56 | 5.957 | 38.636 | 37.218 | 1.00 | 0.00 |
| ATOM | 484 | CD1 | PHE | 1 | 56 | 5.243 | 38.642 | 38.488 | 1.00 | 0.00 |
| ATOM | 485 | CD2 | PHE | 1 | 56 | 5.258 | 38.651 | 36.021 | 1.00 | 0.00 |
| ATOM | 486 | CE1 | PHE | 1 | 56 | 3.843 | 38.681 | 38.472 | 1.00 | 0.00 |
| ATOM | 487 | CE2 | PHE | 1 | 56 | 3.883 | 38.677 | 36.013 | 1.00 | 0.00 |
| ATOM | 488 | CZ | PHE | 1 | 56 | 3.180 | 38.671 | 37.227 | 1.00 | 0.00 |
| ATOM | 489 | H | PHE | 1 | 56 | 8.146 | 40.122 | 35.416 | 1.00 | 0.00 |
| ATOM | 490 | N | PRO | 1 | 57 | 10.161 | 40.000 | 38.828 | 1.00 | 0.00 |
| ATOM | 491 | CA | PRO | 1 | 57 | 11.669 | 39.843 | 38.911 | 1.00 | 0.00 |
| ATOM | 492 | C | PRO | 1 | 57 | 12.092 | 38.428 | 39.104 | 1.00 | 0.00 |
| ATOM | 493 | O | PRO | 1 | 57 | 11.362 | 37.470 | 39.343 | 1.00 | 0.00 |
| ATOM | 494 | CB | PRO | 1 | 57 | 12.003 | 40.789 | 40.050 | 1.00 | 0.00 |
| ATOM | 495 | CG | PRO | 1 | 57 | 10.739 | 40.883 | 40.945 | 1.00 | 0.00 |

FIG. 1K

| ATOM | 496 | CD | PRO | 1 | 57 | 9.576 | 40.703 | 39.952 | 1.00 | 0.00 |
| ATOM | 497 | N | THR | 1 | 58 | 13.424 | 38.247 | 38.912 | 1.00 | 0.00 |
| ATOM | 498 | CA | THR | 1 | 58 | 14.071 | 37.056 | 39.470 | 1.00 | 0.00 |
| ATOM | 499 | C | THR | 1 | 58 | 13.788 | 36.737 | 40.841 | 1.00 | 0.00 |
| ATOM | 500 | O | THR | 1 | 58 | 13.926 | 35.629 | 41.294 | 1.00 | 0.00 |
| ATOM | 501 | CB | THR | 1 | 58 | 15.541 | 37.145 | 39.032 | 1.00 | 0.00 |
| ATOM | 502 | OG1 | THR | 1 | 58 | 15.680 | 37.609 | 37.672 | 1.00 | 0.00 |
| ATOM | 503 | CG2 | THR | 1 | 58 | 16.131 | 35.762 | 39.182 | 1.00 | 0.00 |
| ATOM | 504 | H | THR | 1 | 58 | 14.036 | 38.966 | 38.583 | 1.00 | 0.00 |
| ATOM | 505 | 1HG | THR | 1 | 58 | 16.524 | 37.297 | 37.373 | 1.00 | 0.00 |
| ATOM | 506 | N | ASP | 1 | 59 | 13.457 | 37.777 | 41.583 | 1.00 | 0.00 |
| ATOM | 507 | CA | ASP | 1 | 59 | 13.181 | 37.664 | 43.011 | 1.00 | 0.00 |
| ATOM | 508 | C | ASP | 1 | 59 | 11.769 | 37.504 | 43.490 | 1.00 | 0.00 |
| ATOM | 509 | O | ASP | 1 | 59 | 11.159 | 38.230 | 44.245 | 1.00 | 0.00 |
| ATOM | 510 | CB | ASP | 1 | 59 | 13.889 | 38.750 | 43.734 | 1.00 | 0.00 |
| ATOM | 511 | CG | ASP | 1 | 59 | 13.491 | 40.164 | 43.290 | 1.00 | 0.00 |
| ATOM | 512 | OD1 | ASP | 1 | 59 | 14.211 | 40.777 | 42.414 | 1.00 | 0.00 |
| ATOM | 513 | OD2 | ASP | 1 | 59 | 12.597 | 40.779 | 43.786 | 1.00 | 0.00 |
| ATOM | 514 | H | ASP | 1 | 59 | 13.329 | 38.682 | 41.178 | 1.00 | 0.00 |
| ATOM | 515 | N | TYR | 1 | 60 | 11.264 | 36.412 | 43.011 | 1.00 | 0.00 |
| ATOM | 516 | CA | TYR | 1 | 60 | 9.821 | 36.218 | 43.226 | 1.00 | 0.00 |
| ATOM | 517 | C | TYR | 1 | 60 | 9.406 | 35.407 | 44.477 | 1.00 | 0.00 |
| ATOM | 518 | O | TYR | 1 | 60 | 10.033 | 34.441 | 44.781 | 1.00 | 0.00 |
| ATOM | 519 | CB | TYR | 1 | 60 | 9.157 | 35.843 | 41.829 | 1.00 | 0.00 |
| ATOM | 520 | CG | TYR | 1 | 60 | 7.838 | 36.612 | 41.789 | 1.00 | 0.00 |
| ATOM | 521 | CD1 | TYR | 1 | 60 | 8.034 | 37.990 | 41.682 | 1.00 | 0.00 |
| ATOM | 522 | CD2 | TYR | 1 | 60 | 6.546 | 36.030 | 41.874 | 1.00 | 0.00 |
| ATOM | 523 | CE1 | TYR | 1 | 60 | 6.972 | 38.870 | 41.721 | 1.00 | 0.00 |
| ATOM | 524 | CE2 | TYR | 1 | 60 | 5.438 | 36.950 | 41.740 | 1.00 | 0.00 |
| ATOM | 525 | CZ | TYR | 1 | 60 | 5.729 | 38.357 | 41.751 | 1.00 | 0.00 |
| ATOM | 526 | OH | TYR | 1 | 60 | 4.710 | 39.254 | 41.968 | 1.00 | 0.00 |
| ATOM | 527 | H | TYR | 1 | 60 | 11.803 | 35.930 | 42.321 | 1.00 | 0.00 |
| ATOM | 528 | HH | TYR | 1 | 60 | 4.929 | 39.846 | 42.676 | 1.00 | 0.00 |
| ATOM | 529 | N | PRO | 1 | 61 | 8.341 | 35.745 | 45.277 | 1.00 | 0.00 |
| ATOM | 530 | CA | PRO | 1 | 61 | 7.611 | 36.986 | 45.163 | 1.00 | 0.00 |
| ATOM | 531 | C | PRO | 1 | 61 | 8.031 | 38.127 | 46.103 | 1.00 | 0.00 |
| ATOM | 532 | O | PRO | 1 | 61 | 7.544 | 38.281 | 47.197 | 1.00 | 0.00 |
| ATOM | 533 | CB | PRO | 1 | 61 | 6.241 | 36.440 | 45.549 | 1.00 | 0.00 |
| ATOM | 534 | CG | PRO | 1 | 61 | 6.451 | 35.361 | 46.551 | 1.00 | 0.00 |
| ATOM | 535 | CD | PRO | 1 | 61 | 7.874 | 34.846 | 46.340 | 1.00 | 0.00 |
| ATOM | 536 | N | PHE | 1 | 62 | 8.921 | 39.015 | 45.665 | 1.00 | 0.00 |
| ATOM | 537 | CA | PHE | 1 | 62 | 9.316 | 39.953 | 46.675 | 1.00 | 0.00 |
| ATOM | 538 | C | PHE | 1 | 62 | 9.091 | 41.436 | 46.494 | 1.00 | 0.00 |
| ATOM | 539 | O | PHE | 1 | 62 | 8.277 | 42.242 | 47.033 | 1.00 | 0.00 |
| ATOM | 540 | CB | PHE | 1 | 62 | 10.835 | 39.726 | 47.093 | 1.00 | 0.00 |

FIG. 1L

| ATOM | 541 | CG | PHE | 1 | 62 | 11.170 | 38.343 | 47.627 | 1.00 | 0.00 |
|------|-----|-----|-----|---|----|--------|--------|--------|------|------|
| ATOM | 542 | CD1 | PHE | 1 | 62 | 10.256 | 37.516 | 48.364 | 1.00 | 0.00 |
| ATOM | 543 | CD2 | PHE | 1 | 62 | 12.483 | 37.929 | 47.366 | 1.00 | 0.00 |
| ATOM | 544 | CD1 | PHE | 1 | 62 | 10.701 | 36.264 | 48.835 | 1.00 | 0.00 |
| ATOM | 545 | CE2 | PHE | 1 | 62 | 12.959 | 36.670 | 47.863 | 1.00 | 0.00 |
| ATOM | 546 | CZ | PHE | 1 | 62 | 12.047 | 35.848 | 48.625 | 1.00 | 0.00 |
| ATOM | 547 | H | PHE | 1 | 62 | 9.595 | 38.814 | 44.954 | 1.00 | 0.00 |
| ATOM | 548 | N | LYS | 1 | 63 | 9.863 | 41.843 | 45.495 | 1.00 | 0.00 |
| ATOM | 549 | CA | LYS | 1 | 63 | 9.548 | 43.072 | 44.849 | 1.00 | 0.00 |
| ATOM | 550 | C | LYS | 1 | 63 | 8.397 | 43.143 | 43.796 | 1.00 | 0.00 |
| ATOM | 551 | O | LYS | 1 | 63 | 8.195 | 42.199 | 42.989 | 1.00 | 0.00 |
| ATOM | 552 | CB | LYS | 1 | 63 | 10.812 | 43.763 | 44.268 | 1.00 | 0.00 |
| ATOM | 553 | CG | LYS | 1 | 63 | 11.675 | 44.228 | 45.486 | 1.00 | 0.00 |
| ATOM | 554 | CD | LYS | 1 | 63 | 13.008 | 44.744 | 45.085 | 1.00 | 0.00 |
| ATOM | 555 | CE | LYS | 1 | 63 | 14.141 | 43.689 | 44.873 | 1.00 | 0.00 |
| ATOM | 556 | NZ | LYS | 1 | 63 | 13.885 | 43.084 | 43.628 | 1.00 | 0.00 |
| ATOM | 557 | H | LYS | 1 | 63 | 10.564 | 41.264 | 45.080 | 1.00 | 0.00 |
| ATOM | 558 | 1HZ | LYS | 1 | 63 | 13.607 | 43.721 | 42.854 | 1.00 | 0.00 |
| ATOM | 559 | 2HZ | LYS | 1 | 63 | 14.604 | 42.424 | 43.268 | 1.00 | 0.00 |
| ATOM | 560 | 3HZ | LYS | 1 | 63 | 13.094 | 42.434 | 43.815 | 1.00 | 0.00 |
| ATOM | 561 | N | PRO | 1 | 64 | 7.612 | 44.296 | 44.014 | 1.00 | 0.00 |
| ATOM | 562 | CA | PRO | 1 | 64 | 6.552 | 44.555 | 43.047 | 1.00 | 0.00 |
| ATOM | 563 | C | PRO | 1 | 64 | 7.019 | 44.767 | 41.595 | 1.00 | 0.00 |
| ATOM | 564 | O | PRO | 1 | 64 | 7.827 | 45.556 | 41.196 | 1.00 | 0.00 |
| ATOM | 565 | CB | PRO | 1 | 64 | 5.886 | 45.784 | 43.752 | 1.00 | 0.00 |
| ATOM | 566 | CG | PRO | 1 | 64 | 6.176 | 45.623 | 45.213 | 1.00 | 0.00 |
| ATOM | 567 | CD | PRO | 1 | 64 | 7.675 | 45.291 | 45.131 | 1.00 | 0.00 |
| ATOM | 568 | N | PRO | 1 | 65 | 6.468 | 43.847 | 40.815 | 1.00 | 0.00 |
| ATOM | 569 | CA | PRO | 1 | 65 | 6.866 | 43.890 | 39.421 | 1.00 | 0.00 |
| ATOM | 570 | C | PRO | 1 | 65 | 6.657 | 45.256 | 38.732 | 1.00 | 0.00 |
| ATOM | 571 | O | PRO | 1 | 65 | 5.727 | 46.018 | 38.928 | 1.00 | 0.00 |
| ATOM | 572 | CB | PRO | 1 | 65 | 6.066 | 42.674 | 38.836 | 1.00 | 0.00 |
| ATOM | 573 | CG | PRO | 1 | 65 | 5.450 | 41.854 | 39.988 | 1.00 | 0.00 |
| ATOM | 574 | CD | PRO | 1 | 65 | 5.640 | 42.744 | 41.175 | 1.00 | 0.00 |
| ATOM | 575 | N | LYS | 1 | 66 | 7.616 | 45.558 | 37.920 | 1.00 | 0.00 |
| ATOM | 576 | CA | LYS | 1 | 66 | 7.582 | 46.638 | 36.943 | 1.00 | 0.00 |
| ATOM | 577 | C | LYS | 1 | 66 | 6.677 | 46.420 | 35.758 | 1.00 | 0.00 |
| ATOM | 578 | O | LYS | 1 | 66 | 6.975 | 45.573 | 34.895 | 1.00 | 0.00 |
| ATOM | 579 | CB | LYS | 1 | 66 | 9.042 | 47.057 | 36.632 | 1.00 | 0.00 |
| ATOM | 580 | CG | LYS | 1 | 66 | 9.026 | 47.916 | 35.359 | 1.00 | 0.00 |
| ATOM | 581 | CD | LYS | 1 | 66 | 9.426 | 47.170 | 34.096 | 1.00 | 0.00 |
| ATOM | 582 | CE | LYS | 1 | 66 | 8.561 | 47.715 | 32.960 | 1.00 | 0.00 |
| ATOM | 583 | NZ | LYS | 1 | 66 | 7.593 | 46.650 | 32.604 | 1.00 | 0.00 |
| ATOM | 584 | H | LYS | 1 | 66 | 8.315 | 44.850 | 37.823 | 1.00 | 0.00 |
| ATOM | 585 | 1HZ | LYS | 1 | 66 | 7.202 | 46.096 | 33.393 | 1.00 | 0.00 |

FIG. 1M

| ATOM | 586 | 2HZ | LYS | 1 | 66 | 6.840 | 46.784 | 31.900 | 1.00 | 0.00 |
| --- | --- | --- | --- | --- | --- | --- | --- | --- | --- | --- |
| ATOM | 587 | 3HZ | LYS | 1 | 66 | 8.051 | 45.940 | 31.997 | 1.00 | 0.00 |
| ATOM | 588 | N | VAL | 1 | 67 | 5.641 | 47.237 | 35.914 | 1.00 | 0.00 |
| ATOM | 589 | CA | VAL | 1 | 67 | 4.618 | 47.092 | 34.890 | 1.00 | 0.00 |
| ATOM | 590 | C | VAL | 1 | 67 | 4.669 | 48.202 | 33.838 | 1.00 | 0.00 |
| ATOM | 591 | O | VAL | 1 | 67 | 5.038 | 49.290 | 34.212 | 1.00 | 0.00 |
| ATOM | 592 | CB | VAL | 1 | 67 | 3.210 | 47.149 | 35.616 | 1.00 | 0.00 |
| ATOM | 593 | CG1 | VAL | 1 | 67 | 2.008 | 47.020 | 34.713 | 1.00 | 0.00 |
| ATOM | 594 | CG2 | VAL | 1 | 67 | 3.138 | 46.027 | 36.596 | 1.00 | 0.00 |
| ATOM | 595 | H | VAL | 1 | 67 | 5.652 | 47.816 | 36.730 | 1.00 | 0.00 |
| ATOM | 596 | N | ALA | 1 | 68 | 4.284 | 47.890 | 32.576 | 1.00 | 0.00 |
| ATOM | 597 | CA | ALA | 1 | 68 | 4.063 | 49.030 | 31.594 | 1.00 | 0.00 |
| ATOM | 598 | C | ALA | 1 | 68 | 3.210 | 48.782 | 30.295 | 1.00 | 0.00 |
| ATOM | 599 | O | ALA | 1 | 68 | 3.050 | 47.648 | 29.844 | 1.00 | 0.00 |
| ATOM | 600 | CB | ALA | 1 | 68 | 5.339 | 49.726 | 31.204 | 1.00 | 0.00 |
| ATOM | 601 | H | ALA | 1 | 68 | 3.936 | 46.964 | 32.435 | 1.00 | 0.00 |
| ATOM | 602 | N | PHE | 1 | 69 | 2.744 | 49.948 | 29.729 | 1.00 | 0.00 |
| ATOM | 603 | CA | PHE | 1 | 69 | 2.170 | 49.817 | 28.428 | 1.00 | 0.00 |
| ATOM | 604 | C | PHE | 1 | 69 | 3.003 | 49.993 | 27.243 | 1.00 | 0.00 |
| ATOM | 605 | O | PHE | 1 | 69 | 4.174 | 50.197 | 27.488 | 1.00 | 0.00 |
| ATOM | 606 | CB | PHE | 1 | 69 | 1.005 | 50.861 | 28.439 | 1.00 | 0.00 |
| ATOM | 607 | CG | PHE | 1 | 69 | -0.236 | 50.170 | 29.024 | 1.00 | 0.00 |
| ATOM | 608 | CD1 | PHE | 1 | 69 | -0.571 | 50.303 | 30.370 | 1.00 | 0.00 |
| ATOM | 609 | CD2 | PHE | 1 | 69 | -1.184 | 49.627 | 28.119 | 1.00 | 0.00 |
| ATOM | 610 | CE1 | PHE | 1 | 69 | -1.950 | 49.879 | 30.749 | 1.00 | 0.00 |
| ATOM | 611 | CE2 | PHE | 1 | 69 | -2.510 | 49.317 | 28.496 | 1.00 | 0.00 |
| ATOM | 612 | CZ | PHE | 1 | 69 | -2.919 | 49.553 | 29.836 | 1.00 | 0.00 |
| ATOM | 613 | H | PHE | 1 | 69 | 3.122 | 50.795 | 30.100 | 1.00 | 0.00 |
| ATOM | 614 | N | THR | 1 | 70 | 2.418 | 49.796 | 26.051 | 1.00 | 0.00 |
| ATOM | 615 | CA | THR | 1 | 70 | 3.174 | 50.059 | 24.865 | 1.00 | 0.00 |
| ATOM | 616 | C | THR | 1 | 70 | 2.540 | 50.869 | 23.691 | 1.00 | 0.00 |
| ATOM | 617 | O | THR | 1 | 70 | 3.101 | 51.454 | 22.774 | 1.00 | 0.00 |
| ATOM | 618 | CB | THR | 1 | 70 | 3.823 | 48.693 | 24.425 | 1.00 | 0.00 |
| ATOM | 619 | OG1 | THR | 1 | 70 | 4.392 | 47.934 | 25.445 | 1.00 | 0.00 |
| ATOM | 620 | OG2 | THR | 1 | 70 | 5.058 | 48.811 | 23.431 | 1.00 | 0.00 |
| ATOM | 621 | H | THR | 1 | 70 | 1.520 | 49.357 | 26.083 | 1.00 | 0.00 |
| ATOM | 622 | 1HG | THR | 1 | 70 | 4.658 | 48.583 | 26.082 | 1.00 | 0.00 |
| ATOM | 623 | N | THR | 1 | 71 | 1.197 | 50.942 | 23.754 | 1.00 | 0.00 |
| ATOM | 624 | CA | THR | 1 | 71 | 0.474 | 51.874 | 22.977 | 1.00 | 0.00 |
| ATOM | 625 | C | THR | 1 | 71 | 0.307 | 53.101 | 23.855 | 1.00 | 0.00 |
| ATOM | 626 | O | THR | 1 | 71 | 0.482 | 52.993 | 25.082 | 1.00 | 0.00 |
| ATOM | 627 | CB | THR | 1 | 71 | -0.890 | 51.230 | 22.586 | 1.00 | 0.00 |
| ATOM | 628 | OG1 | THR | 1 | 71 | -1.547 | 51.870 | 21.495 | 1.00 | 0.00 |
| ATOM | 629 | OG2 | THR | 1 | 71 | -1.785 | 51.219 | 23.771 | 1.00 | 0.00 |
| ATOM | 630 | H | THR | 1 | 71 | 0.626 | 50.488 | 24.439 | 1.00 | 0.00 |

FIG. 1N

| ATOM | 631 | 1HG | THR | 1 | 71 | -2.411 | 51.480 | 21.469 | 1.00 | 0.00 |
| ATOM | 632 | N | ARG | 1 | 72 | -0.235 | 54.173 | 23.226 | 1.00 | 0.00 |
| ATOM | 633 | CA | ARG | 1 | 72 | -0.698 | 55.208 | 24.180 | 1.00 | 0.00 |
| ATOM | 634 | C | ARG | 1 | 72 | -2.115 | 55.840 | 23.974 | 1.00 | 0.00 |
| ATOM | 635 | O | ARG | 1 | 72 | -2.217 | 57.065 | 23.776 | 1.00 | 0.00 |
| ATOM | 636 | CB | ARG | 1 | 72 | 0.288 | 56.308 | 24.307 | 1.00 | 0.00 |
| ATOM | 637 | CG | ARG | 1 | 72 | 0.826 | 56.516 | 25.720 | 1.00 | 0.00 |
| ATOM | 638 | CD | ARG | 1 | 72 | -0.223 | 57.282 | 26.573 | 1.00 | 0.00 |
| ATOM | 639 | NE | ARG | 1 | 72 | -0.810 | 58.398 | 25.780 | 1.00 | 0.00 |
| ATOM | 640 | CZ | ARG | 1 | 72 | -1.820 | 59.012 | 26.451 | 1.00 | 0.00 |
| ATOM | 641 | NH1 | ARG | 1 | 72 | -2.145 | 58.515 | 27.586 | 1.00 | 0.00 |
| ATOM | 642 | NH2 | ARG | 1 | 72 | -2.355 | 60.127 | 25.927 | 1.00 | 0.00 |
| ATOM | 643 | H | ARG | 1 | 72 | -0.234 | 54.315 | 22.236 | 1.00 | 0.00 |
| ATOM | 644 | HE | ARG | 1 | 72 | -0.329 | 58.774 | 24.988 | 1.00 | 0.00 |
| ATOM | 645 | 1HH1 | ARG | 1 | 72 | -2.785 | 59.051 | 28.137 | 1.00 | 0.00 |
| ATOM | 646 | 2HH1 | ARG | 1 | 72 | -1.825 | 57.675 | 28.024 | 1.00 | 0.00 |
| ATOM | 647 | 1HH2 | ARG | 1 | 72 | -3.097 | 60.500 | 26.484 | 1.00 | 0.00 |
| ATOM | 648 | 2HH2 | ARG | 1 | 72 | -2.152 | 60.596 | 25.068 | 1.00 | 0.00 |
| ATOM | 649 | N | ILE | 1 | 73 | -3.075 | 54.932 | 24.098 | 1.00 | 0.00 |
| ATOM | 650 | CA | ILE | 1 | 73 | -4.455 | 55.301 | 23.856 | 1.00 | 0.00 |
| ATOM | 651 | C | ILE | 1 | 73 | -5.133 | 55.989 | 25.011 | 1.00 | 0.00 |
| ATOM | 652 | O | ILE | 1 | 73 | -5.141 | 55.445 | 26.100 | 1.00 | 0.00 |
| ATOM | 653 | CB | ILE | 1 | 73 | -5.320 | 54.019 | 23.424 | 1.00 | 0.00 |
| ATOM | 654 | CG1 | ILE | 1 | 73 | -6.850 | 54.247 | 23.209 | 1.00 | 0.00 |
| ATOM | 655 | CG2 | ILE | 1 | 73 | -5.101 | 52.911 | 24.470 | 1.00 | 0.00 |
| ATOM | 656 | CD1 | ILE | 1 | 73 | -7.640 | 52.943 | 22.791 | 1.00 | 0.00 |
| ATOM | 657 | H | ILE | 1 | 73 | -2.810 | 53.985 | 24.276 | 1.00 | 0.00 |
| ATOM | 658 | N | TYR | 1 | 74 | -5.586 | 57.222 | 24.931 | 1.00 | 0.00 |
| ATOM | 659 | CA | TYR | 1 | 74 | -6.264 | 58.008 | 25.978 | 1.00 | 0.00 |
| ATOM | 660 | C | TYR | 1 | 74 | -6.963 | 57.448 | 27.192 | 1.00 | 0.00 |
| ATOM | 661 | O | TYR | 1 | 74 | -8.075 | 56.932 | 27.127 | 1.00 | 0.00 |
| ATOM | 662 | CB | TYR | 1 | 74 | -7.256 | 58.973 | 25.383 | 1.00 | 0.00 |
| ATOM | 663 | CG | TYR | 1 | 74 | -6.545 | 60.286 | 24.901 | 1.00 | 0.00 |
| ATOM | 664 | CD1 | TYR | 1 | 74 | -6.956 | 61.516 | 25.449 | 1.00 | 0.00 |
| ATOM | 665 | CD2 | TYR | 1 | 74 | -5.569 | 60.181 | 23.917 | 1.00 | 0.00 |
| ATOM | 666 | CE1 | TYR | 1 | 74 | -6.330 | 62.685 | 25.001 | 1.00 | 0.00 |
| ATOM | 667 | CE2 | TYR | 1 | 74 | -4.903 | 61.360 | 23.491 | 1.00 | 0.00 |
| ATOM | 668 | CZ | TYR | 1 | 74 | -5.267 | 62.542 | 24.077 | 1.00 | 0.00 |
| ATOM | 669 | OH | TYR | 1 | 74 | -4.459 | 63.643 | 23.767 | 1.00 | 0.00 |
| ATOM | 670 | H | TYR | 1 | 74 | -5.424 | 57.697 | 24.066 | 1.00 | 0.00 |
| ATOM | 671 | HH | TYR | 1 | 74 | -3.605 | 63.327 | 23.505 | 1.00 | 0.00 |
| ATOM | 672 | N | HIS | 1 | 75 | -6.244 | 57.542 | 28.315 | 1.00 | 0.00 |
| ATOM | 673 | CA | HIS | 1 | 75 | -6.712 | 57.415 | 29.691 | 1.00 | 0.00 |
| ATOM | 674 | C | HIS | 1 | 75 | -5.809 | 58.147 | 30.656 | 1.00 | 0.00 |
| ATOM | 675 | O | HIS | 1 | 75 | -4.618 | 58.037 | 30.567 | 1.00 | 0.00 |

FIG. 10

| ATOM | 676 | CB   | HIS | 1 | 75 | -6.903 | 55.932 | 30.164 | 1.00 | 0.00 |
| ATOM | 677 | CG   | HIS | 1 | 75 | -7.735 | 55.806 | 31.446 | 1.00 | 0.00 |
| ATOM | 678 | ND1  | HIS | 1 | 75 | -7.320 | 55.110 | 32.508 | 1.00 | 0.00 |
| ATOM | 679 | CD2  | HIS | 1 | 75 | -9.064 | 56.208 | 31.661 | 1.00 | 0.00 |
| ATOM | 680 | CE1  | HIS | 1 | 75 | -8.337 | 55.061 | 33.430 | 1.00 | 0.00 |
| ATOM | 681 | NE2  | HIS | 1 | 75 | -9.429 | 55.714 | 32.910 | 1.00 | 0.00 |
| ATOM | 682 | H    | HIS | 1 | 75 | -5.350 | 57.933 | 28.095 | 1.00 | 0.00 |
| ATOM | 683 | 1HD  | HIS | 1 | 75 | -6.505 | 54.575 | 32.609 | 1.00 | 0.00 |
| ATOM | 684 | N    | PRO | 1 | 76 | -6.406 | 58.853 | 31.622 | 1.00 | 0.00 |
| ATOM | 685 | CA   | PRO | 1 | 76 | -5.631 | 59.218 | 32.828 | 1.00 | 0.00 |
| ATOM | 686 | C    | PRO | 1 | 76 | -4.689 | 58.242 | 33.509 | 1.00 | 0.00 |
| ATOM | 687 | O    | PRO | 1 | 76 | -3.545 | 58.615 | 33.836 | 1.00 | 0.00 |
| ATOM | 688 | CB   | PRO | 1 | 76 | -6.733 | 59.744 | 33.703 | 1.00 | 0.00 |
| ATOM | 689 | CG   | PRO | 1 | 76 | -8.079 | 59.421 | 33.110 | 1.00 | 0.00 |
| ATOM | 690 | CD   | PRO | 1 | 76 | -7.793 | 59.273 | 31.629 | 1.00 | 0.00 |
| ATOM | 691 | N    | ASN | 1 | 77 | -5.120 | 56.969 | 33.592 | 1.00 | 0.00 |
| ATOM | 692 | CA   | ASN | 1 | 77 | -4.149 | 55.995 | 34.023 | 1.00 | 0.00 |
| ATOM | 693 | C    | ASN | 1 | 77 | -3.232 | 55.350 | 32.975 | 1.00 | 0.00 |
| ATOM | 694 | O    | ASN | 1 | 77 | -2.235 | 54.686 | 33.293 | 1.00 | 0.00 |
| ATOM | 695 | CB   | ASN | 1 | 77 | -4.544 | 55.069 | 35.221 | 1.00 | 0.00 |
| ATOM | 696 | CG   | ASN | 1 | 77 | -5.398 | 53.859 | 34.799 | 1.00 | 0.00 |
| ATOM | 697 | OD1  | ASN | 1 | 77 | -5.269 | 53.390 | 33.660 | 1.00 | 0.00 |
| ATOM | 698 | ND2  | ASN | 1 | 77 | -6.264 | 53.533 | 35.724 | 1.00 | 0.00 |
| ATOM | 699 | H    | ASN | 1 | 77 | -6.008 | 56.604 | 33.313 | 1.00 | 0.00 |
| ATOM | 700 | 1HD2 | ASN | 1 | 77 | -6.190 | 53.971 | 36.620 | 1.00 | 0.00 |
| ATOM | 701 | 2HD2 | ASN | 1 | 77 | -6.951 | 52.815 | 35.616 | 1.00 | 0.00 |
| ATOM | 702 | N    | ILE | 1 | 78 | -3.577 | 55.500 | 31.719 | 1.00 | 0.00 |
| ATOM | 703 | CA   | ILE | 1 | 78 | -2.428 | 55.111 | 30.819 | 1.00 | 0.00 |
| ATOM | 704 | C    | ILE | 1 | 78 | -1.366 | 56.277 | 30.720 | 1.00 | 0.00 |
| ATOM | 705 | O    | ILE | 1 | 78 | -1.137 | 56.911 | 29.708 | 1.00 | 0.00 |
| ATOM | 706 | CB   | ILE | 1 | 78 | -2.914 | 54.640 | 29.485 | 1.00 | 0.00 |
| ATOM | 707 | CG1  | ILE | 1 | 78 | -4.001 | 53.586 | 29.802 | 1.00 | 0.00 |
| ATOM | 708 | CG2  | ILE | 1 | 78 | -1.718 | 53.970 | 28.701 | 1.00 | 0.00 |
| ATOM | 709 | CD1  | ILE | 1 | 78 | -4.663 | 53.021 | 28.578 | 1.00 | 0.00 |
| ATOM | 710 | H    | ILE | 1 | 78 | -4.240 | 56.191 | 31.434 | 1.00 | 0.00 |
| ATOM | 711 | N    | ASN | 1 | 79 | -0.702 | 56.476 | 31.895 | 1.00 | 0.00 |
| ATOM | 712 | CA   | ASN | 1 | 79 |  0.362 | 57.504 | 31.918 | 1.00 | 0.00 |
| ATOM | 713 | C    | ASN | 1 | 79 |  1.462 | 57.177 | 30.980 | 1.00 | 0.00 |
| ATOM | 714 | O    | ASN | 1 | 79 |  1.783 | 56.010 | 30.852 | 1.00 | 0.00 |
| ATOM | 715 | CB   | ASN | 1 | 79 |  0.977 | 57.697 | 33.357 | 1.00 | 0.00 |
| ATOM | 716 | CG   | ASN | 1 | 79 |  1.977 | 58.941 | 33.383 | 1.00 | 0.00 |
| ATOM | 717 | OD1  | ASN | 1 | 79 |  3.102 | 58.857 | 32.913 | 1.00 | 0.00 |
| ATOM | 718 | ND2  | ASN | 1 | 79 |  1.421 | 59.936 | 34.047 | 1.00 | 0.00 |
| ATOM | 719 | H    | ASN | 1 | 79 | -0.879 | 55.970 | 32.740 | 1.00 | 0.00 |
| ATOM | 720 | 1HD2 | ASN | 1 | 79 |  0.480 | 59.871 | 34.380 | 1.00 | 0.00 |

FIG. 1P

| ATOM | 721 | 2HD2 | ASN | 1 | 79 | 1.919 | 60.793 | 34.181 | 1.00 | 0.00 |
|------|-----|------|-----|---|----|-------|--------|--------|------|------|
| ATOM | 722 | N | SER | 1 | 80 | 2.012 | 58.274 | 30.296 | 1.00 | 0.00 |
| ATOM | 723 | CA | SER | 1 | 80 | 3.020 | 58.037 | 29.307 | 1.00 | 0.00 |
| ATOM | 724 | C | SER | 1 | 80 | 4.213 | 57.172 | 29.722 | 1.00 | 0.00 |
| ATOM | 725 | O | SER | 1 | 80 | 4.736 | 56.463 | 28.906 | 1.00 | 0.00 |
| ATOM | 726 | CB | SER | 1 | 80 | 3.540 | 59.374 | 28.740 | 1.00 | 0.00 |
| ATOM | 727 | OG | SER | 1 | 80 | 2.464 | 60.229 | 28.410 | 1.00 | 0.00 |
| ATOM | 728 | H | SER | 1 | 80 | 1.733 | 59.222 | 30.444 | 1.00 | 0.00 |
| ATOM | 729 | HG | SER | 1 | 80 | 2.142 | 59.977 | 27.555 | 1.00 | 0.00 |
| ATOM | 730 | N | ASN | 1 | 81 | 4.499 | 57.059 | 31.048 | 1.00 | 0.00 |
| ATOM | 731 | CA | ASN | 1 | 81 | 5.499 | 56.121 | 31.571 | 1.00 | 0.00 |
| ATOM | 732 | C | ASN | 1 | 81 | 5.049 | 54.722 | 31.893 | 1.00 | 0.00 |
| ATOM | 733 | O | ASN | 1 | 81 | 5.800 | 53.806 | 32.205 | 1.00 | 0.00 |
| ATOM | 734 | CB | ASN | 1 | 81 | 6.239 | 56.638 | 32.776 | 1.00 | 0.00 |
| ATOM | 735 | CG | ASN | 1 | 81 | 5.190 | 57.043 | 33.835 | 1.00 | 0.00 |
| ATOM | 736 | OD1 | ASN | 1 | 81 | 4.206 | 56.324 | 33.995 | 1.00 | 0.00 |
| ATOM | 737 | ND2 | ASN | 1 | 81 | 5.364 | 58.167 | 34.505 | 1.00 | 0.00 |
| ATOM | 738 | H | ASN | 1 | 81 | 4.021 | 57.645 | 31.702 | 1.00 | 0.00 |
| ATOM | 739 | 1HD2 | ASN | 1 | 81 | 6.256 | 58.616 | 34.550 | 1.00 | 0.00 |
| ATOM | 740 | 2HD2 | ASN | 1 | 81 | 4.596 | 58.637 | 34.941 | 1.00 | 0.00 |
| ATOM | 741 | N | GLY | 1 | 82 | 3.733 | 54.599 | 31.889 | 1.00 | 0.00 |
| ATOM | 742 | CA | GLY | 1 | 82 | 3.169 | 53.260 | 32.012 | 1.00 | 0.00 |
| ATOM | 743 | C | GLY | 1 | 82 | 2.883 | 52.770 | 33.467 | 1.00 | 0.00 |
| ATOM | 744 | O | GLY | 1 | 82 | 2.757 | 51.537 | 33.677 | 1.00 | 0.00 |
| ATOM | 745 | H | GLY | 1 | 82 | 3.081 | 55.355 | 31.943 | 1.00 | 0.00 |
| ATOM | 746 | N | SER | 1 | 83 | 2.699 | 53.686 | 34.408 | 1.00 | 0.00 |
| ATOM | 747 | CA | SER | 1 | 83 | 2.182 | 53.325 | 35.707 | 1.00 | 0.00 |
| ATOM | 748 | C | SER | 1 | 83 | 0.653 | 53.291 | 35.565 | 1.00 | 0.00 |
| ATOM | 749 | O | SER | 1 | 83 | 0.005 | 53.943 | 34.723 | 1.00 | 0.00 |
| ATOM | 750 | CB | SER | 1 | 83 | 2.747 | 54.306 | 36.709 | 1.00 | 0.00 |
| ATOM | 751 | OG | SER | 1 | 83 | 4.143 | 54.436 | 36.565 | 1.00 | 0.00 |
| ATOM | 752 | H | SER | 1 | 83 | 2.728 | 54.661 | 34.188 | 1.00 | 0.00 |
| ATOM | 753 | HG | SER | 1 | 83 | 4.292 | 55.334 | 36.830 | 1.00 | 0.00 |
| ATOM | 754 | N | ILE | 1 | 84 | 0.097 | 52.428 | 36.385 | 1.00 | 0.00 |
| ATOM | 755 | CA | ILE | 1 | 84 | -1.370 | 52.476 | 36.461 | 1.00 | 0.00 |
| ATOM | 756 | C | ILE | 1 | 84 | -1.850 | 52.509 | 37.900 | 1.00 | 0.00 |
| ATOM | 757 | O | ILE | 1 | 84 | -1.165 | 51.998 | 38.770 | 1.00 | 0.00 |
| ATOM | 758 | CB | ILE | 1 | 84 | -1.937 | 51.310 | 35.649 | 1.00 | 0.00 |
| ATOM | 759 | CG1 | ILE | 1 | 84 | -0.929 | 50.116 | 35.676 | 1.00 | 0.00 |
| ATOM | 760 | CG2 | ILE | 1 | 84 | -2.392 | 51.652 | 34.199 | 1.00 | 0.00 |
| ATOM | 761 | CD1 | ILE | 1 | 84 | -0.862 | 49.238 | 36.911 | 1.00 | 0.00 |
| ATOM | 762 | H | ILE | 1 | 84 | 0.585 | 51.890 | 37.073 | 1.00 | 0.00 |
| ATOM | 763 | N | CYS | 1 | 85 | -3.050 | 53.104 | 38.044 | 1.00 | 0.00 |
| ATOM | 764 | CA | CYS | 1 | 85 | -3.456 | 53.377 | 39.430 | 1.00 | 0.00 |
| ATOM | 765 | C | CYS | 1 | 85 | -3.946 | 52.219 | 40.300 | 1.00 | 0.00 |

FIG. 1Q

| ATOM | 766 | O | CYS | 1 | 85 | -3.154 | 51.631 | 40.977 | 1.00 | 0.00 |
| --- | --- | --- | --- | --- | --- | --- | --- | --- | --- | --- |
| ATOM | 767 | CB | CYS | 1 | 85 | -4.494 | 54.530 | 39.493 | 1.00 | 0.00 |
| ATOM | 768 | SG | CYS | 1 | 85 | -3.719 | 56.051 | 38.899 | 1.00 | 0.00 |
| ATOM | 769 | H | CYS | 1 | 85 | -3.555 | 53.567 | 37.316 | 1.00 | 0.00 |
| ATOM | 770 | N | LEU | 1 | 86 | -5.235 | 51.872 | 40.178 | 1.00 | 0.00 |
| ATOM | 771 | CA | LEU | 1 | 86 | -5.836 | 50.570 | 40.669 | 1.00 | 0.00 |
| ATOM | 772 | C | LEU | 1 | 86 | -5.198 | 49.716 | 41.738 | 1.00 | 0.00 |
| ATOM | 773 | O | LEU | 1 | 86 | -4.347 | 48.854 | 41.497 | 1.00 | 0.00 |
| ATOM | 774 | CB | LEU | 1 | 86 | -6.178 | 49.687 | 39.435 | 1.00 | 0.00 |
| ATOM | 775 | CG | LEU | 1 | 86 | -5.062 | 49.502 | 38.390 | 1.00 | 0.00 |
| ATOM | 776 | CD1 | LEU | 1 | 86 | -4.529 | 48.072 | 38.326 | 1.00 | 0.00 |
| ATOM | 777 | CD2 | LEU | 1 | 86 | -5.429 | 49.889 | 36.984 | 1.00 | 0.00 |
| ATOM | 778 | H | LEU | 1 | 86 | -5.624 | 52.275 | 39.349 | 1.00 | 0.00 |
| ATOM | 779 | N | ASP | 1 | 87 | -5.646 | 49.975 | 42.971 | 1.00 | 0.00 |
| ATOM | 780 | CA | ASP | 1 | 87 | -5.525 | 49.028 | 44.088 | 1.00 | 0.00 |
| ATOM | 781 | C | ASP | 1 | 87 | -4.109 | 48.504 | 44.263 | 1.00 | 0.00 |
| ATOM | 782 | O | ASP | 1 | 87 | -3.363 | 49.082 | 45.066 | 1.00 | 0.00 |
| ATOM | 783 | CB | ASP | 1 | 87 | -6.527 | 47.893 | 43.964 | 1.00 | 0.00 |
| ATOM | 784 | CG | ASP | 1 | 87 | -6.431 | 46.788 | 45.001 | 1.00 | 0.00 |
| ATOM | 785 | OD1 | ASP | 1 | 87 | -6.114 | 47.067 | 46.154 | 1.00 | 0.00 |
| ATOM | 786 | OD2 | ASP | 1 | 87 | -6.744 | 45.628 | 44.680 | 1.00 | 0.00 |
| ATOM | 787 | H | ASP | 1 | 87 | -6.293 | 50.722 | 43.123 | 1.00 | 0.00 |
| ATOM | 788 | N | ILE | 1 | 88 | -3.811 | 47.376 | 43.540 | 1.00 | 0.00 |
| ATOM | 789 | CA | ILE | 1 | 88 | -2.601 | 46.573 | 43.737 | 1.00 | 0.00 |
| ATOM | 790 | C | ILE | 1 | 88 | -1.296 | 47.330 | 43.558 | 1.00 | 0.00 |
| ATOM | 791 | O | ILE | 1 | 88 | -0.504 | 47.300 | 44.477 | 1.00 | 0.00 |
| ATOM | 792 | CB | ILE | 1 | 88 | -2.715 | 45.322 | 42.836 | 1.00 | 0.00 |
| ATOM | 793 | CG1 | ILE | 1 | 88 | -2.555 | 45.432 | 41.275 | 1.00 | 0.00 |
| ATOM | 794 | CG2 | ILE | 1 | 88 | -4.113 | 44.647 | 42.978 | 1.00 | 0.00 |
| ATOM | 795 | CD1 | ILE | 1 | 88 | -2.522 | 44.051 | 40.547 | 1.00 | 0.00 |
| ATOM | 796 | H | ILE | 1 | 88 | -4.311 | 47.348 | 42.674 | 1.00 | 0.00 |
| ATOM | 797 | N | LEU | 1 | 89 | -1.124 | 48.012 | 42.405 | 1.00 | 0.00 |
| ATOM | 798 | CA | LEU | 1 | 89 | -0.037 | 48.937 | 42.290 | 1.00 | 0.00 |
| ATOM | 799 | C | LEU | 1 | 89 | -0.284 | 50.287 | 42.862 | 1.00 | 0.00 |
| ATOM | 800 | O | LEU | 1 | 89 | -0.472 | 51.269 | 42.113 | 1.00 | 0.00 |
| ATOM | 801 | CB | LEU | 1 | 89 | -0.443 | 49.094 | 40.838 | 1.00 | 0.00 |
| ATOM | 802 | CG | LEU | 1 | 89 | 1.420 | 48.043 | 40.288 | 1.00 | 0.00 |
| ATOM | 803 | CD1 | LEU | 1 | 89 | 2.636 | 47.915 | 41.237 | 1.00 | 0.00 |
| ATOM | 804 | CD2 | LEU | 1 | 89 | 0.675 | 46.722 | 39.962 | 1.00 | 0.00 |
| ATOM | 805 | H | LEU | 1 | 89 | -1.933 | 48.260 | 41.873 | 1.00 | 0.00 |
| ATOM | 806 | N | ARG | 1 | 90 | -0.418 | 50.340 | 44.189 | 1.00 | 0.00 |
| ATOM | 807 | CA | ARG | 1 | 90 | -0.026 | 51.384 | 45.135 | 1.00 | 0.00 |
| ATOM | 808 | C | ARG | 1 | 90 | -0.473 | 51.119 | 46.614 | 1.00 | 0.00 |
| ATOM | 809 | O | ARG | 1 | 90 | 0.338 | 50.878 | 47.480 | 1.00 | 0.00 |
| ATOM | 810 | CB | ARG | 1 | 90 | -0.202 | 52.892 | 44.694 | 1.00 | 0.00 |

FIG. 1R

| ATOM | 811 | CG | ARG | 1 | 90 | -1.614 | 53.327 | 44.386 | 1.00 | 0.00 |
| --- | --- | --- | --- | --- | --- | --- | --- | --- | --- | --- |
| ATOM | 812 | CD | ARG | 1 | 90 | -1.771 | 54.741 | 43.914 | 1.00 | 0.00 |
| ATOM | 813 | NE | ARG | 1 | 90 | -3.140 | 55.176 | 43.940 | 1.00 | 0.00 |
| ATOM | 814 | CZ | ARG | 1 | 90 | -3.469 | 56.121 | 43.129 | 1.00 | 0.00 |
| ATOM | 815 | NH1 | ARG | 1 | 90 | -4.669 | 56.743 | 43.266 | 1.00 | 0.00 |
| ATOM | 816 | NH2 | ARG | 1 | 90 | -2.772 | 56.487 | 42.010 | 1.00 | 0.00 |
| ATOM | 817 | H | ARG | 1 | 90 | -0.600 | 49.477 | 44.659 | 1.00 | 0.00 |
| ATOM | 818 | HE | ARG | 1 | 90 | -3.649 | 54.776 | 44.702 | 1.00 | 0.00 |
| ATOM | 819 | 1HH1 | ARG | 1 | 90 | -4.832 | 57.565 | 42.721 | 1.00 | 0.00 |
| ATOM | 820 | 2HH1 | ARG | 1 | 90 | -5.240 | 56.526 | 44.058 | 1.00 | 0.00 |
| ATOM | 821 | 1HH2 | ARG | 1 | 90 | -3.123 | 57.247 | 41.464 | 1.00 | 0.00 |
| ATOM | 822 | 2HH2 | ARG | 1 | 90 | -1.861 | 56.172 | 41.743 | 1.00 | 0.00 |
| ATOM | 823 | N | SER | 1 | 91 | -1.779 | 51.132 | 46.880 | 1.00 | 0.00 |
| ATOM | 824 | CA | SER | 1 | 91 | -2.246 | 50.840 | 48.231 | 1.00 | 0.00 |
| ATOM | 825 | C | SER | 1 | 91 | -2.039 | 49.496 | 48.865 | 1.00 | 0.00 |
| ATOM | 826 | O | SER | 1 | 91 | -2.155 | 49.290 | 50.084 | 1.00 | 0.00 |
| ATOM | 827 | CB | SER | 1 | 91 | -3.706 | 51.221 | 48.212 | 1.00 | 0.00 |
| ATOM | 828 | OG | SER | 1 | 91 | -3.945 | 52.494 | 47.464 | 1.00 | 0.00 |
| ATOM | 829 | H | SER | 1 | 91 | -2.454 | 51.157 | 46.142 | 1.00 | 0.00 |
| ATOM | 830 | HG | SER | 1 | 91 | -4.217 | 53.128 | 48.114 | 1.00 | 0.00 |
| ATOM | 831 | N | GLN | 1 | 92 | -1.695 | 48.524 | 47.995 | 1.00 | 0.00 |
| ATOM | 832 | CA | GLN | 1 | 92 | -1.634 | 47.187 | 48.509 | 1.00 | 0.00 |
| ATOM | 833 | C | GLN | 1 | 92 | -0.236 | 46.696 | 48.873 | 1.00 | 0.00 |
| ATOM | 834 | O | GLN | 1 | 92 | 0.410 | 46.150 | 47.994 | 1.00 | 0.00 |
| ATOM | 835 | CB | GLN | 1 | 92 | -2.345 | 46.228 | 47.634 | 1.00 | 0.00 |
| ATOM | 836 | CG | GLN | 1 | 92 | -2.649 | 44.788 | 48.100 | 1.00 | 0.00 |
| ATOM | 837 | CD | GLN | 1 | 92 | -3.525 | 44.132 | 47.065 | 1.00 | 0.00 |
| ATOM | 838 | OE1 | GLN | 1 | 92 | -3.152 | 43.262 | 46.300 | 1.00 | 0.00 |
| ATOM | 839 | NE2 | GLN | 1 | 92 | -4.730 | 44.710 | 46.949 | 1.00 | 0.00 |
| ATOM | 840 | H | GLN | 1 | 92 | -1.391 | 48.636 | 47.050 | 1.00 | 0.00 |
| ATOM | 841 | 1HE2 | GLN | 1 | 92 | -5.066 | 45.404 | 47.585 | 1.00 | 0.00 |
| ATOM | 842 | 2HE2 | GLN | 1 | 92 | -5.388 | 44.626 | 46.200 | 1.00 | 0.00 |
| ATOM | 843 | N | TRP | 1 | 93 | 0.004 | 46.795 | 50.177 | 1.00 | 0.00 |
| ATOM | 844 | CA | TRP | 1 | 93 | 1.331 | 46.337 | 50.664 | 1.00 | 0.00 |
| ATOM | 845 | C | TRP | 1 | 93 | 1.379 | 44.847 | 50.786 | 1.00 | 0.00 |
| ATOM | 846 | O | TRP | 1 | 93 | 1.413 | 44.260 | 51.903 | 1.00 | 0.00 |
| ATOM | 847 | CB | TRP | 1 | 93 | 1.747 | 47.092 | 51.956 | 1.00 | 0.00 |
| ATOM | 848 | CG | TRP | 1 | 93 | 3.202 | 46.849 | 52.298 | 1.00 | 0.00 |
| ATOM | 849 | CD1 | TRP | 1 | 93 | 3.639 | 46.472 | 53.600 | 1.00 | 0.00 |
| ATOM | 850 | CD2 | TRP | 1 | 93 | 4.403 | 46.830 | 51.462 | 1.00 | 0.00 |
| ATOM | 851 | NE1 | TRP | 1 | 93 | 4.988 | 46.241 | 53.629 | 1.00 | 0.00 |
| ATOM | 852 | CE2 | TRP | 1 | 93 | 5.507 | 46.452 | 52349 | 1.00 | 0.00 |
| ATOM | 853 | CE3 | TRP | 1 | 93 | 4.729 | 47.037 | 50.081 | 1.00 | 0.00 |
| ATOM | 854 | CZ2 | TRP | 1 | 93 | 6.827 | 46.319 | 51.969 | 1.00 | 0.00 |
| ATOM | 855 | CZ3 | TRP | 1 | 93 | 6.089 | 46.803 | 49.652 | 1.00 | 0.00 |

FIG. 1S

| ATOM | 856 | CH2 | GLN | 1 | 93 | 7.087 | 46.544 | 50.614 | 1.00 | 0.00 |
| --- | --- | --- | --- | --- | --- | --- | --- | --- | --- | --- |
| ATOM | 857 | H | TRP | 1 | 93 | -0.649 | 47.178 | 50.831 | 1.00 | 0.00 |
| ATOM | 858 | 1HE | TRP | 1 | 93 | 5.547 | 46.033 | 54.407 | 1.00 | 0.00 |
| ATOM | 859 | N | SER | 1 | 94 | 1.490 | 44.234 | 49.587 | 1.00 | 0.00 |
| ATOM | 860 | CA | SER | 1 | 94 | 1.669 | 42.774 | 49.495 | 1.00 | 0.00 |
| ATOM | 861 | C | SER | 1 | 94 | 2.312 | 42.502 | 48.181 | 1.00 | 0.00 |
| ATOM | 862 | O | SER | 1 | 94 | 1.754 | 42.899 | 47.152 | 1.00 | 0.00 |
| ATOM | 863 | CB | SER | 1 | 94 | 0.262 | 42.108 | 49.593 | 1.00 | 0.00 |
| ATOM | 864 | OG | SER | 1 | 94 | -0.412 | 42.387 | 48.358 | 1.00 | 0.00 |
| ATOM | 865 | H | SER | 1 | 94 | 1.514 | 44.787 | 48.753 | 1.00 | 0.00 |
| ATOM | 866 | HG | SER | 1 | 94 | -0.092 | 43.219 | 48.036 | 1.00 | 0.00 |
| ATOM | 867 | N | PRO | 1 | 95 | 3.435 | 41.722 | 48.161 | 1.00 | 0.00 |
| ATOM | 868 | CA | PRO | 1 | 95 | 3.724 | 41.167 | 46.814 | 1.00 | 0.00 |
| ATOM | 869 | C | PRO | 1 | 95 | 2.942 | 39.914 | 46.539 | 1.00 | 0.00 |
| ATOM | 870 | O | PRO | 1 | 95 | 3.473 | 38.913 | 46.075 | 1.00 | 0.00 |
| ATOM | 871 | CB | PRO | 1 | 95 | 5.243 | 40.974 | 46.986 | 1.00 | 0.00 |
| ATOM | 872 | CG | PRO | 1 | 95 | 5.541 | 40.527 | 48.437 | 1.00 | 0.00 |
| ATOM | 873 | CD | PRO | 1 | 95 | 4.449 | 41.477 | 49.162 | 1.00 | 0.00 |
| ATOM | 874 | N | ALA | 1 | 96 | 1.631 | 39.963 | 46.751 | 1.00 | 0.00 |
| ATOM | 875 | CA | ALA | 1 | 96 | 0.742 | 38.929 | 46.296 | 1.00 | 0.00 |
| ATOM | 876 | C | ALA | 1 | 96 | 0.008 | 39.214 | 45.017 | 1.00 | 0.00 |
| ATOM | 877 | O | ALA | 1 | 96 | -1.215 | 39.302 | 44.930 | 1.00 | 0.00 |
| ATOM | 878 | CB | ALA | 1 | 96 | -0.170 | 38.368 | 47.410 | 1.00 | 0.00 |
| ATOM | 879 | H | ALA | 1 | 96 | 1.330 | 40.893 | 46.964 | 1.00 | 0.00 |
| ATOM | 880 | N | LEU | 1 | 97 | 0.914 | 39.429 | 44.050 | 1.00 | 0.00 |
| ATOM | 881 | CA | LEU | 1 | 97 | -.494 | 39.917 | 42.699 | 1.00 | 0.00 |
| ATOM | 882 | C | LEU | 1 | 97 | 0.773 | 38.935 | 41.618 | 1.00 | 0.00 |
| ATOM | 883 | O | LEU | 1 | 97 | 1.827 | 38.934 | 40.926 | 1.00 | 0.00 |
| ATOM | 884 | CB | LEU | 1 | 97 | 1.151 | 41.281 | 42.350 | 1.00 | 0.00 |
| ATOM | 885 | CG | LEU | 1 | 97 | 1.297 | 42.490 | 43.278 | 1.00 | 0.00 |
| ATOM | 886 | CD1 | LEU | 1 | 97 | 1.815 | 43.697 | 42.585 | 1.00 | 0.00 |
| ATOM | 887 | CD2 | LEU | 1 | 97 | -0.071 | 42.794 | 44.045 | 1.00 | 0.00 |
| ATOM | 888 | H | LEU | 1 | 97 | 1.874 | 39.401 | 44.330 | 1.00 | 0.00 |
| ATOM | 889 | N | THR | 1 | 98 | -0.195 | 38.052 | 41.512 | 1.00 | 0.00 |
| ATOM | 890 | CA | THR | 1 | 98 | -0.030 | 37.084 | 40.473 | 1.00 | 0.00 |
| ATOM | 891 | C | THR | 1 | 98 | -0.990 | 37.340 | 39.335 | 1.00 | 0.00 |
| ATOM | 892 | O | THR | 1 | 98 | -2.041 | 37.953 | 39.480 | 1.00 | 0.00 |
| ATOM | 893 | CB | THR | 1 | 98 | -0.163 | 35.572 | 41.034 | 1.00 | 0.00 |
| ATOM | 894 | OG1 | THR | 1 | 98 | 0.762 | 34.750 | 40.274 | 1.00 | 0.00 |
| ATOM | 895 | CG2 | THR | 1 | 98 | -1.504 | 35.029 | 41.173 | 1.00 | 0.00 |
| ATOM | 896 | H | THR | 1 | 98 | -1.027 | 38.138 | 42.060 | 1.00 | 0.00 |
| ATOM | 897 | 1HG | THR | 1 | 98 | 0.266 | 34.090 | 39.808 | 1.00 | 0.00 |
| ATOM | 898 | N | ILE | 1 | 99 | -0.363 | 37.052 | 38.234 | 1.00 | 0.00 |
| ATOM | 899 | CA | ILE | 1 | 99 | -0.894 | 37.527 | 37.020 | 1.00 | 0.00 |
| ATOM | 900 | C | ILE | 1 | 99 | -2.380 | 37.698 | 36.697 | 1.00 | 0.00 |

FIG. 1T

| | | | | | | | | | |
|---|---|---|---|---|---|---|---|---|---|
| ATOM | 901 | O | ILE | 1 | 99 | -2.724 | 38.764 | 36.246 | 1.00 | 0.00 |
| ATOM | 902 | CB | ILE | 1 | 99 | -0.082 | 37.024 | 35.825 | 1.00 | 0.00 |
| ATOM | 903 | CG1 | ILE | 1 | 99 | -0.308 | 37.613 | 34.450 | 1.00 | 0.00 |
| ATOM | 904 | CG2 | ILE | 1 | 99 | -0.305 | 35.483 | 35.600 | 1.00 | 0.00 |
| ATOM | 905 | CD1 | ILE | 1 | 99 | 0.494 | 38.884 | 34.205 | 1.00 | 0.00 |
| ATOM | 906 | H | ILE | 1 | 99 | 0.345 | 36.354 | 38.343 | 1.00 | 0.00 |
| ATOM | 907 | N | SER | 1 | 100 | -3.270 | 36.706 | 36.849 | 1.00 | 0.00 |
| ATOM | 908 | CA | SER | 1 | 100 | -4.724 | 36.906 | 36.744 | 1.00 | 0.00 |
| ATOM | 909 | C | SER | 1 | 100 | -5.204 | 38.211 | 37.355 | 1.00 | 0.00 |
| ATOM | 910 | O | SER | 1 | 100 | -5.742 | 39.096 | 36.685 | 1.00 | 0.00 |
| ATOM | 911 | CB | SER | 1 | 100 | -5.415 | 35.624 | 37.222 | 1.00 | 0.00 |
| ATOM | 912 | OG | SER | 1 | 100 | -4.736 | 35.233 | 38.459 | 1.00 | 0.00 |
| ATOM | 913 | H | SER | 1 | 100 | -2.868 | 35.938 | 37.348 | 1.00 | 0.00 |
| ATOM | 914 | HG | SER | 1 | 100 | -5.204 | 34.561 | 38.936 | 1.00 | 0.00 |
| ATOM | 915 | N | LYS | 1 | 101 | -4.768 | 38.359 | 38.639 | 1.00 | 0.00 |
| ATOM | 916 | CA | LYS | 1 | 101 | -5.113 | 39.564 | 39.413 | 1.00 | 0.00 |
| ATOM | 917 | C | LYS | 1 | 101 | -4.402 | 40.879 | 39.024 | 1.00 | 0.00 |
| ATOM | 918 | O | LYS | 1 | 101 | -4.754 | 41.953 | 39.522 | 1.00 | 0.00 |
| ATOM | 919 | CB | LYS | 1 | 101 | -4.912 | 39.238 | 40.866 | 1.00 | 0.00 |
| ATOM | 920 | CG | LYS | 1 | 101 | -5.274 | 40.259 | 42.002 | 1.00 | 0.00 |
| ATOM | 921 | CD | LYS | 1 | 101 | -3.984 | 40.688 | 42.680 | 1.00 | 0.00 |
| ATOM | 922 | CE | LYS | 1 | 101 | -4.365 | 40.819 | 44.136 | 1.00 | 0.00 |
| ATOM | 923 | NZ | LYS | 1 | 101 | -3.203 | 41.272 | 44.871 | 1.00 | 0.00 |
| ATOM | 924 | H | LYS | 1 | 101 | -4.189 | 37.616 | 38.973 | 1.00 | 0.00 |
| ATOM | 925 | 1HZ | LYS | 1 | 101 | -2.880 | 42.183 | 44.487 | 1.00 | 0.00 |
| ATOM | 926 | 2HZ | LYS | 1 | 101 | -3.296 | 41.474 | 45.887 | 1.00 | 0.00 |
| ATOM | 927 | 3HZ | LYS | 1 | 101 | -2.424 | 40.594 | 44.747 | 1.00 | 0.00 |
| ATOM | 928 | N | VAL | 1 | 102 | -3.475 | 40.750 | 38.077 | 1.00 | 0.00 |
| ATOM | 929 | CA | VAL | 1 | 102 | -2.860 | 41.961 | 37.557 | 1.00 | 0.00 |
| ATOM | 930 | C | VAL | 1 | 102 | -3.510 | 42.388 | 36.239 | 1.00 | 0.00 |
| ATOM | 931 | O | VAL | 1 | 102 | -3.849 | 43.567 | 35.957 | 1.00 | 0.00 |
| ATOM | 932 | CB | VAL | 1 | 102 | -1.348 | 41.798 | 37.381 | 1.00 | 0.00 |
| ATOM | 933 | CG1 | VAL | 1 | 102 | -0.665 | 43.196 | 37.067 | 1.00 | 0.00 |
| ATOM | 934 | CG2 | VAL | 1 | 102 | -0.609 | 41.199 | 38.633 | 1.00 | 0.00 |
| ATOM | 935 | H | VAL | 1 | 102 | -3.259 | 39.834 | 37.736 | 1.00 | 0.00 |
| ATOM | 936 | N | LEU | 1 | 103 | -3.744 | 41.406 | 35.354 | 1.00 | 0.00 |
| ATOM | 937 | CA | LEU | 1 | 103 | -4.192 | 41.772 | 34.076 | 1.00 | 0.00 |
| ATOM | 938 | C | LEU | 1 | 103 | -5.690 | 42.032 | 34.111 | 1.00 | 0.00 |
| ATOM | 939 | O | LEU | 1 | 103 | -6.211 | 42.990 | 33.448 | 1.00 | 0.00 |
| ATOM | 940 | CB | LEU | 1 | 103 | -3.726 | 40.740 | 32.995 | 1.00 | 0.00 |
| ATOM | 941 | CG | LEU | 1 | 103 | -2.507 | 41.346 | 32.267 | 1.00 | 0.00 |
| ATOM | 942 | CD1 | LEU | 1 | 103 | -1.795 | 40.254 | 31.459 | 1.00 | 0.00 |
| ATOM | 943 | CD2 | LEU | 1 | 103 | -2.903 | 42.587 | 31.541 | 1.00 | 0.00 |
| ATOM | 944 | H | LEU | 1 | 103 | -3.911 | 40.514 | 35.773 | 1.00 | 0.00 |
| ATOM | 945 | N | LEU | 1 | 104 | -6.424 | 41.145 | 34.856 | 1.00 | 0.00 |

FIG. 1U

| ATOM | 946 | CA | LEU | 1 | 104 | -7.810 | 41.575 | 35.127 | 1.00 | 0.00 |
| ATOM | 947 | C | LEU | 1 | 104 | -7.855 | 42.961 | 35.724 | 1.00 | 0.00 |
| ATOM | 948 | O | LEU | 1 | 104 | -8.500 | 43.819 | 35.130 | 1.00 | 0.00 |
| ATOM | 949 | CB | LEU | 1 | 104 | -8.506 | 40.520 | 35.983 | 1.00 | 0.00 |
| ATOM | 950 | CG | LEU | 1 | 104 | -9.953 | 40.895 | 36.094 | 1.00 | 0.00 |
| ATOM | 951 | CD1 | LEU | 1 | 104 | -10.722 | 40.812 | 34.846 | 1.00 | 0.00 |
| ATOM | 952 | CD2 | LEU | 1 | 104 | -10.702 | 40.028 | 37.125 | 1.00 | 0.00 |
| ATOM | 953 | H | LEU | 1 | 104 | -6.131 | 40.287 | 35.278 | 1.00 | 0.00 |
| ATOM | 954 | N | SER | 1 | 105 | -7.118 | 43.132 | 36.833 | 1.00 | 0.00 |
| ATOM | 955 | CA | SER | 1 | 105 | -7.386 | 44.418 | 37.550 | 1.00 | 0.00 |
| ATOM | 956 | C | SER | 1 | 105 | -6.973 | 45.720 | 36.778 | 1.00 | 0.00 |
| ATOM | 957 | O | SER | 1 | 105 | -7.602 | 46.7373 | 36.986 | 1.00 | 0.00 |
| ATOM | 958 | CB | SER | 1 | 105 | -6.761 | 44.419 | 38.909 | 1.00 | 0.00 |
| ATOM | 959 | OG | SER | 1 | 105 | -7.437 | 43.369 | 39.676 | 1.00 | 0.00 |
| ATOM | 960 | H | SER | 1 | 105 | -6.570 | 42.378 | 37.194 | 1.00 | 0.00 |
| ATOM | 961 | HG | SER | 1 | 105 | -7.053 | 42.532 | 39.449 | 1.00 | 0.00 |
| ATOM | 962 | N | ILE | 1 | 106 | -5.953 | 45.587 | 35.942 | 1.00 | 0.00 |
| ATOM | 963 | CA | ILE | 1 | 106 | -5.565 | 46.649 | 34.950 | 1.00 | 0.00 |
| ATOM | 964 | C | ILE | 1 | 106 | -6.694 | 46.937 | 33.906 | 1.00 | 0.00 |
| ATOM | 965 | O | ILE | 1 | 106 | -7.039 | 48.044 | 33.459 | 1.00 | 0.00 |
| ATOM | 966 | CB | ILE | 1 | 106 | -4.240 | 46.330 | 34.320 | 1.00 | 0.00 |
| ATOM | 967 | CG1 | ILE | 1 | 106 | -3.013 | 46.371 | 35.246 | 1.00 | 0.00 |
| ATOM | 968 | CG2 | ILE | 1 | 106 | -3.926 | 47.235 | 33.094 | 1.00 | 0.00 |
| ATOM | 969 | CD1 | ILE | 1 | 106 | -1.919 | 45.558 | 34.629 | 1.00 | 0.00 |
| ATOM | 970 | H | ILE | 1 | 106 | -5.752 | 44.610 | 35.861 | 1.00 | 0.00 |
| ATOM | 971 | N | CYS | 1 | 107 | -7.274 | 45.781 | 33.409 | 1.00 | 0.00 |
| ATOM | 972 | CA | CYS | 1 | 107 | -8.520 | 45.970 | 32.586 | 1.00 | 0.00 |
| ATOM | 973 | C | CYS | 1 | 107 | -9.757 | 46.433 | 33.338 | 1.00 | 0.00 |
| ATOM | 974 | O | CYS | 1 | 107 | -10.600 | 47.145 | 32.731 | 1.00 | 0.00 |
| ATOM | 975 | CB | CYS | 1 | 107 | -8.856 | 44.670 | 31.741 | 1.00 | 0.00 |
| ATOM | 976 | SG | CYS | 1 | 107 | -7.429 | 44.342 | 30.720 | 1.00 | 0.00 |
| ATOM | 977 | H | CYS | 1 | 107 | -7.117 | 44.941 | 33.928 | 1.00 | 0.00 |
| ATOM | 978 | N | SER | 1 | 108 | -9.830 | 46.108 | 34.695 | 1.00 | 0.00 |
| ATOM | 979 | CA | SER | 1 | 108 | -11.060 | 46.479 | 35.328 | 1.00 | 0.00 |
| ATOM | 980 | C | SER | 1 | 108 | -11.219 | 47.952 | 35.369 | 1.00 | 0.00 |
| ATOM | 981 | O | SER | 1 | 108 | -12.337 | 48.405 | 35.150 | 1.00 | 0.00 |
| ATOM | 982 | CB | SER | 1 | 108 | -11.152 | 45.799 | 36.770 | 1.00 | 0.00 |
| ATOM | 983 | OG | SER | 1 | 108 | -11.173 | 44.322 | 36.587 | 1.00 | 0.00 |
| ATOM | 984 | H | SER | 1 | 108 | -9.241 | 45.357 | 34.991 | 1.00 | 0.00 |
| ATOM | 985 | HG | SER | 1 | 108 | -11.732 | 44.168 | 35.837 | 1.00 | 0.00 |
| ATOM | 986 | N | LEU | 1 | 109 | -10.155 | 48.631 | 35.780 | 1.00 | 0.00 |
| ATOM | 987 | CA | LEU | 1 | 109 | -10.220 | 50.104 | 35.653 | 1.00 | 0.00 |
| ATOM | 988 | C | LEU | 1 | 109 | -9.817 | 50.687 | 34.332 | 1.00 | 0.00 |
| ATOM | 989 | O | LEU | 1 | 109 | -9.444 | 51.821 | 34.154 | 1.00 | 0.00 |
| ATOM | 990 | CB | LEU | 1 | 109 | -9.558 | 50.849 | 36.830 | 1.00 | 0.00 |

FIG. 1V

| | | | | | | | | | |
|---|---|---|---|---|---|---|---|---|---|
| ATOM | 991 | CG | LEU | 1 | 109 | -10.330 | 50.611 | 38.192 | 1.00 0.00 |
| ATOM | 992 | CD1 | LEU | 1 | 109 | -9.530 | 51.170 | 39.297 | 1.00 0.00 |
| ATOM | 993 | CD2 | LEU | 1 | 109 | -11.727 | 51.119 | 38.162 | 1.00 0.00 |
| ATOM | 994 | H | LEU | 1 | 109 | -9.232 | 48.266 | 35.900 | 1.00 0.00 |
| ATOM | 995 | N | LEU | 1 | 110 | -9.934 | 49.766 | 33.374 | 1.00 0.00 |
| ATOM | 996 | CA | LEU | 1 | 110 | -10.049 | 50.216 | 32.023 | 1.00 0.00 |
| ATOM | 997 | C | LEU | 1 | 110 | -11.371 | 49.745 | 31.298 | 1.00 0.00 |
| ATOM | 998 | O | LEU | 1 | 110 | -11.455 | 49.615 | 30.102 | 1.00 0.00 |
| ATOM | 999 | CB | LEU | 1 | 110 | -8.751 | 49.816 | 31.312 | 1.00 0.00 |
| ATOM | 1000 | CG | LEU | 1 | 110 | -7.942 | 50.875 | 30.483 | 1.00 0.00 |
| ATOM | 1001 | CD1 | LEU | 1 | 110 | -7.368 | 51.879 | 31.470 | 1.00 0.00 |
| ATOM | 1002 | CD2 | LEU | 1 | 110 | -6.829 | 50.314 | 29.656 | 1.00 0.00 |
| ATOM | 1003 | H | LEU | 1 | 110 | -10.041 | 48.784 | 33.533 | 1.00 0.00 |
| ATOM | 1004 | N | CYS | 1 | 111 | -12.308 | 49.338 | 32.152 | 1.00 0.00 |
| ATOM | 1005 | CA | CYS | 1 | 111 | -13.548 | 48.999 | 31.551 | 1.00 0.00 |
| ATOM | 1006 | C | CYS | 1 | 111 | -14.398 | 50.255 | 31.331 | 1.00 0.00 |
| ATOM | 1007 | O | CYS | 1 | 111 | -14.130 | 50.937 | 30.370 | 1.00 0.00 |
| ATOM | 1008 | CB | CYS | 1 | 111 | -14.416 | 48.026 | 32.492 | 1.00 0.00 |
| ATOM | 1009 | SG | CYS | 1 | 111 | -14.116 | 46.278 | 32.379 | 1.00 0.00 |
| ATOM | 1010 | H | CYS | 1 | 111 | -12.026 | 49.328 | 33.112 | 1.00 0.00 |
| ATOM | 1011 | N | ASP | 1 | 112 | -15.364 | 50.587 | 32.178 | 1.00 0.00 |
| ATOM | 1012 | CA | ASP | 1 | 112 | -15.593 | 51.987 | 32.403 | 1.00 0.00 |
| ATOM | 1013 | C | ASP | 1 | 112 | -14.518 | 52.650 | 33.331 | 1.00 0.00 |
| ATOM | 1014 | O | ASP | 1 | 112 | -14.507 | 52.386 | 34.545 | 1.00 0.00 |
| ATOM | 1015 | CB | ASP | 1 | 112 | -17.121 | 52.182 | 32.807 | 1.00 0.00 |
| ATOM | 1016 | CG | ASP | 1 | 112 | -17.888 | 52.937 | 31.766 | 1.00 0.00 |
| ATOM | 1017 | OD1 | ASP | 1 | 112 | -19.113 | 52.989 | 31.785 | 1.00 0.00 |
| ATOM | 1018 | OD2 | ASP | 1 | 112 | -17.199 | 53.537 | 30.912 | 1.00 0.00 |
| ATOM | 1019 | H | ASP | 1 | 112 | -15.765 | 49.992 | 32.874 | 1.00 0.00 |
| ATOM | 1020 | N | PRO | 1 | 113 | -13.531 | 53.288 | 32.615 | 1.00 0.00 |
| ATOM | 1021 | CA | PRO | 1 | 113 | -12.199 | 53.281 | 33.187 | 1.00 0.00 |
| ATOM | 1022 | C | PRO | 1 | 113 | -12.012 | 54.384 | 34.243 | 1.00 0.00 |
| ATOM | 1023 | O | PRO | 1 | 113 | -12.637 | 55.445 | 34.025 | 1.00 0.00 |
| ATOM | 1024 | CB | PRO | 1 | 113 | -11.398 | 53.419 | 31.897 | 1.00 0.00 |
| ATOM | 1025 | CG | PRO | 1 | 113 | -12.171 | 54.275 | 30.881 | 1.00 0.00 |
| ATOM | 1026 | CD | PRO | 1 | 113 | -13.610 | 53.875 | 31.275 | 1.00 0.00 |
| ATOM | 1027 | N | ASN | 1 | 114 | -11.261 | 54.180 | 35.336 | 1.00 0.00 |
| ATOM | 1028 | CA | ASN | 1 | 114 | -11.182 | 55.245 | 36.355 | 1.00 0.00 |
| ATOM | 1029 | C | ASN1 | 1 | 114 | -10.597 | 56.637 | 35.865 | 1.00 0.00 |
| ATOM | 1030 | O | ASN | 1 | 114 | -9.378 | 56.803 | 35.714 | 1.00 0.00 |
| ATOM | 1031 | CB | ASN | 1 | 114 | -10.330 | 54.764 | 37.541 | 1.00 0.00 |
| ATOM | 1032 | CG | ASN | 1 | 114 | -10.137 | 55.772 | 38.647 | 1.00 0.00 |
| ATOM | 1033 | OD1 | ASN | 1 | 114 | -9.345 | 56.731 | 38.656 | 1.00 0.00 |
| ATOM | 1034 | ND2 | ASN | 1 | 114 | -10.980 | 55.677 | 39.678 | 1.00 0.00 |
| ATOM | 1035 | H | ASN | 1 | 114 | -10.615 | 53.417 | 35.332 | 1.00 0.00 |

FIG. 1W

| ATOM | 1036 | 1HD2 | ASN | 1 | 114 | -11.523 | 54.841 | 39.754 | 1.00 | 0.00 |
|------|------|------|-----|---|-----|---------|--------|--------|------|------|
| ATOM | 1037 | 2HD2 | ASN | 1 | 114 | -11.318 | 56.332 | 40.354 | 1.00 | 0.00 |
| ATOM | 1038 | N    | PRO | 1 | 115 | -11.568 | 57.547 | 35.930 | 1.00 | 0.00 |
| ATOM | 1039 | CA   | PRO | 1 | 115 | -11.202 | 58.938 | 35.634 | 1.00 | 0.00 |
| ATOM | 1040 | C    | PRO | 1 | 115 | -10.529 | 59.625 | 36.725 | 1.00 | 0.00 |
| ATOM | 1041 | O    | PRO | 1 | 115 | -9.921  | 60.690 | 36.497 | 1.00 | 0.00 |
| ATOM | 1042 | CB   | PRO | 1 | 115 | -12.673 | 59.470 | 35.330 | 1.00 | 0.00 |
| ATOM | 1043 | CG   | PRO | 1 | 115 | -13.720 | 58.740 | 58.740 | 1.00 | 0.00 |
| ATOM | 1044 | CD   | PRO | 1 | 115 | -12.975 | 57.417 | 36.159 | 1.00 | 0.00 |
| ATOM | 1045 | N    | ASP | 1 | 116 | -10.763 | 59.056 | 37.948 | 1.00 | 0.00 |
| ATOM | 1046 | CA   | ASP | 1 | 116 | -10.371 | .59.852 | 39.097 | 1.00 | 0.00 |
| ATOM | 1047 | C    | ASP | 1 | 116 | -8.965  | 60.130 | 39.381 | 1.00 | 0.00 |
| ATOM | 1048 | O    | ASP | 1 | 116 | -8.729  | 61.091 | 40.080 | 1.00 | 0.00 |
| ATOM | 1049 | CB   | ASP | 1 | 116 | -11.112 | 59.169 | 40.210 | 1.00 | 0.00 |
| ATOM | 1050 | CG   | ASP | 1 | 116 | -12.562 | 59.525 | 40.004 | 1.00 | 0.00 |
| ATOM | 1051 | OD1  | ASP | 1 | 116 | -12.897 | 60.693 | 40.229 | 1.00 | 0.00 |
| ATOM | 1052 | OD2  | ASP | 1 | 116 | -13.360 | 58.645 | 39.645 | 1.00 | 0.00 |
| ATOM | 1053 | H    | ASP | 1 | 116 | -11.087 | 58.122 | 38.101 | 1.00 | 0.00 |
| ATOM | 1054 | N    | ASP | 1 | 117 | -8.046  | 59.379 | 38.889 | 1.00 | 0.00 |
| ATOM | 1055 | CA   | ASP | 1 | 117 | -6.667  | 59.696 | 39.115 | 1.00 | 0.00 |
| ATOM | 1056 | C    | ASP | 1 | 117 | -6.000  | 60.362 | 37.956 | 1.00 | 0.00 |
| ATOM | 1057 | O    | ASP | 1 | 117 | -5.912  | 59.906 | 36.817 | 1.00 | 0.00 |
| ATOM | 1058 | CB   | ASP | 1 | 117 | -5.812  | 58.462 | 39.672 | 1.00 | 0.00 |
| ATOM | 1059 | CG   | ASP | 1 | 117 | -5.071  | 58.862 | 40.969 | 1.00 | 0.00 |
| ATOM | 1060 | OD1  | ASP | 1 | 117 | -5.706  | 59.224 | 41.919 | 1.00 | 0.00 |
| ATOM | 1061 | OD2  | ASP | 1 | 117 | -3.839  | 58.861 | 40.982 | 1.00 | 0.00 |
| ATOM | 1062 | H    | ASP | 1 | 117 | -8.297  | 58.676 | 38.225 | 1.00 | 0.00 |
| ATOM | 1063 | N    | PRO | 1 | 118 | -5.510  | 61.616 | 38.265 | 1.00 | 0.00 |
| ATOM | 1064 | CA   | PRO | 1 | 118 | -4.974  | 62.450 | 37.154 | 1.00 | 0.00 |
| ATOM | 1065 | C    | PRO | 1 | 118 | -3.551  | 62.218 | 36.754 | 1.00 | 0.00 |
| ATOM | 1066 | O    | PRO | 1 | 118 | -2.677  | 63.093 | 36.734 | 1.00 | 0.00 |
| ATOM | 1067 | CB   | PRO | 1 | 118 | -5.149  | 63.800 | 37.805 | 1.00 | 0.00 |
| ATOM | 1068 | CG   | PRO | 1 | 118 | -4.936  | 63.597 | 39.311 | 1.00 | 0.00 |
| ATOM | 1069 | CD   | PRO | 1 | 118 | -5.578  | 62.267 | 39.561 | 1.00 | 0.00 |
| ATOM | 1070 | N    | LEU | 1 | 119 | -3.257  | 60.906 | 36.463 | 1.00 | 0.00 |
| ATOM | 1071 | CA   | LEU | 1 | 119 | -1.905  | 60.688 | 35.982 | 1.00 | 0.00 |
| ATOM | 1072 | C    | LEU | 1 | 119 | -1.307  | 61.479 | 34.745 | 1.00 | 0.00 |
| ATOM | 1073 | O    | LEU | 1 | 119 | -0.441  | 62.318 | 34.908 | 1.00 | 0.00 |
| ATOM | 1074 | CB   | LEU | 1 | 119 | -1.456  | 59.254 | 35.930 | 1.00 | 0.00 |
| ATOM | 1075 | CG   | LEU | 1 | 119 | -1.532  | 58.349 | 37.167 | 1.00 | 0.00 |
| ATOM | 1076 | CD1  | LEU | 1 | 119 | -0.912  | 56.912 | 36.972 | 1.00 | 0.00 |
| ATOM | 1077 | CD2  | LEU | 1 | 119 | -0.790  | 58.990 | 38.341 | 1.00 | 0.00 |
| ATOM | 1078 | H    | LEU | 1 | 119 | -3.921  | 60.164 | 36.368 | 1.00 | 0.00 |
| ATOM | 1079 | N    | VAL | 1 | 120 | -1.971  | 61.216 | 33.617 | 1.00 | 0.00 |
| ATOM | 1080 | CA   | VAL | 1 | 120 | -1.959  | 62.209 | 32.538 | 1.00 | 0.00 |

FIG. 1X

| ATOM | 1081 | C   | VAL | 1 | 120 |  3.329  | 62.894 | 32.518 | 1.00 | 0.00 |
| ATOM | 1082 | O   | VAL | 1 | 120 | -4.360  | 62.293 | 32.613 | 1.00 | 0.00 |
| ATOM | 1083 | CB  | VAL | 1 | 120 | -1.499  | 61.604 | 31.253 | 1.00 | 0.00 |
| ATOM | 1084 | CG1 | VAL | 1 | 120 |  0.035  | 61.659 | 31.162 | 1.00 | 0.00 |
| ATOM | 1085 | CG2 | VAL | 1 | 120 | -2.097  | 60.128 | 30.928 | 1.00 | 0.00 |
| ATOM | 1086 | H   | VAL | 1 | 120 | -2.662  | 60.500 | 33.718 | 1.00 | 0.00 |
| ATOM | 1087 | N   | PRO | 1 | 121 | -3.277  | 64.280 | 32.514 | 1.00 | 0.00 |
| ATOM | 1088 | CA  | PRO | 1 | 121 | -4.501  | 65.112 | 32.553 | 1.00 | 0.00 |
| ATOM | 1089 | C   | PRO | 1 | 121 | -5.183  | 65.158 | 31.223 | 1.00 | 0.00 |
| ATOM | 1090 | O   | PRO | 1 | 121 | -5.005  | 66.142 | 30.408 | 1.00 | 0.00 |
| ATOM | 1091 | CB  | PRO | 1 | 121 | -4.078  | 66.545 | 32.890 | 1.00 | 0.00 |
| ATOM | 1092 | CG  | PRO | 1 | 121 | -2.593  | 66.574 | 32.951 | 1.00 | 0.00 |
| ATOM | 1093 | CD  | PRO | 1 | 121 | -2.099  | 65.167 | 32.581 | 1.00 | 0.00 |
| ATOM | 1094 | N   | GLU | 1 | 122 | -5.946  | 64.072 | 30.888 | 1.00 | 0.00 |
| ATOM | 1095 | CA  | GLU | 1 | 122 | -6.357  | 64.028 | 29.506 | 1.00 | 0.00 |
| ATOM | 1096 | C   | GLU | 1 | 122 | -7.790  | 64.010 | 29.329 | 1.00 | 0.00 |
| ATOM | 1097 | O   | GLU | 1 | 122 | -8.390  | 64.999 | 28.991 | 1.00 | 0.00 |
| ATOM | 1098 | CB  | GLU | 1 | 122 | -5.562  | 62.967 | 28.680 | 1.00 | 0.00 |
| ATOM | 1099 | CG  | GLU | 1 | 122 | -5.508  | 61.536 | 29.110 | 1.00 | 0.00 |
| ATOM | 1100 | CD  | GLU | 1 | 122 | -4.428  | 60.841 | 28.287 | 1.00 | 0.00 |
| ATOM | 1101 | OE1 | GLU | 1 | 122 | -4.533  | 59.662 | 28.084 | 1.00 | 0.00 |
| ATOM | 1102 | OE2 | GLU | 1 | 122 | -3.419  | 61.458 | 27.964 | 1.00 | 0.00 |
| ATOM | 1103 | H   | GLU | 1 | 122 | -5.977  | 63.325 | 31.552 | 1.00 | 0.00 |
| ATOM | 1104 | N   | ILE | 1 | 123 | -8.356  | 62.858 | 29.591 | 1.00 | 0.00 |
| ATOM | 1105 | CA  | ILE | 1 | 123 | -9.817  | 62.884 | 29.471 | 1.00 | 0.00 |
| ATOM | 1106 | C   | ILE | 1 | 123 | -10.637 | 62.807 | 30.714 | 1.00 | 0.00 |
| ATOM | 1107 | O   | ILE | 1 | 123 | -11.593 | 63.548 | 30.791 | 1.00 | 0.00 |
| ATOM | 1108 | CB  | ILE | 1 | 123 | -10.141 | 61.868 | 28.403 | 1.00 | 0.00 |
| ATOM | 1109 | CG1 | ILE | 1 | 123 | -11.547 | 62.072 | 27.779 | 1.00 | 0.00 |
| ATOM | 1110 | CG2 | ILE | 1 | 123 | -10.056 | 60.403 | 28.786 | 1.00 | 0.00 |
| ATOM | 1111 | CD1 | ILE | 1 | 123 | -11.761 | 63.221 | 26.711 | 1.00 | 0.00 |
| ATOM | 1112 | H   | ILE | 1 | 123 | -7.841  | 62.124 | 30.034 | 1.00 | 0.00 |
| ATOM | 1113 | N   | ALA | 1 | 124 | -10.185 | 61.872 | 31.630 | 1.00 | 0.00 |
| ATOM | 1114 | CA  | ALA | 1 | 124 | -10.610 | 61.878 | 33.046 | 1.00 | 0.00 |
| ATOM | 1115 | C   | ALA | 1 | 124 | -12.162 | 62.048 | 33.276 | 1.00 | 0.00 |
| ATOM | 1116 | O   | ALA | 1 | 124 | -13.048 | 61.516 | 32.542 | 1.00 | 0.00 |
| ATOM | 1117 | CB  | ALA | 1 | 124 | -9.795  | 63.009 | 33.690 | 1.00 | 0.00 |
| ATOM | 1118 | H   | ALA | 1 | 124 | -9.351  | 61.353 | 31.444 | 1.00 | 0.00 |
| ATOM | 1119 | N   | ARG | 1 | 125 | -12.434 | 62.735 | 34.377 | 1.00 | 0.00 |
| ATOM | 1120 | CA  | ARG | 1 | 125 | -13.795 | 63.212 | 34.682 | 1.00 | 0.00 |
| ATOM | 1121 | C   | ARG | 1 | 125 | -14.747 | 63.817 | 33.616 | 1.00 | 0.00 |
| ATOM | 1122 | O   | ARG | 1 | 125 | -15.960 | 63.759 | 33.744 | 1.00 | 0.00 |
| ATOM | 1123 | CB  | ARG | 1 | 125 | -13.769 | 64.204 | 35.773 | 1.00 | 0.00 |
| ATOM | 1124 | CG  | ARG | 1 | 125 | -13.675 | 63.377 | 37.072 | 1.00 | 0.00 |
| ATOM | 1125 | CD  | ARG | 1 | 125 | -14.972 | 62.537 | 37.191 | 1.00 | 0.00 |

FIG. 1Y

| ATOM | 1126 | NE | ARG | 1 | 125 | -14.854 | 61.500 | 38.232 | 1.00 | 0.00 |
| ATOM | 1127 | CZ | ARG | 1 | 125 | -15.861 | 60.967 | 38.847 | 1.00 | 0.00 |
| ATOM | 1128 | NH1 | ARG | 1 | 125 | -15.655 | 59.990 | 39.749 | 1.00 | 0.00 |
| ATOM | 1129 | NH2 | ARG | 1 | 125 | -17.122 | 61.349 | 38.534 | 1.00 | 0.00 |
| ATOM | 1130 | H | ARG | 1 | 125 | -11.855 | 63.259 | 35.001 | 1.00 | 0.00 |
| ATOM | 1131 | HE | ARG | 1 | 125 | -13.919 | 61.221 | 38.454 | 1.00 | 0.00 |
| ATOM | 1132 | 1HH1 | ARG | 1 | 125 | -16.416 | 59.493 | 40.167 | 1.00 | 0.00 |
| ATOM | 1133 | 2HH1 | ARG | 1 | 125 | -14.748 | 59.735 | 40.086 | 1.00 | 0.00 |
| ATOM | 1134 | 1HH2 | ARG | 1 | 125 | -17.856 | 61.089 | 39.162 | 1.00 | 0.00 |
| ATOM | 1135 | 2HH2 | ARG | 1 | 125 | -17.314 | 61.932 | 37.745 | 1.00 | 0.00 |
| ATOM | 1136 | N | ILE | 1 | 126 | -14.127 | 64.432 | 32.608 | 1.00 | 0.00 |
| ATOM | 1137 | CA | ILE | 1 | 126 | -14.788 | 64.980 | 31.466 | 1.00 | 0.00 |
| ATOM | 1138 | C | ILE | 1 | 126 | -15.410 | 63.856 | 30.692 | 1.00 | 0.00 |
| ATOM | 1139 | O | ILE | 1 | 126 | -16.523 | 63.970 | 30.167 | 1.00 | 0.00 |
| ATOM | 1140 | CB | ILE | 1 | 126 | -13.766 | 65.724 | 30.522 | 1.00 | 0.00 |
| ATOM | 1141 | CG1 | ILE | 1 | 126 | -13.082 | 66.752 | 31.461 | 1.00 | 0.00 |
| ATOM | 1142 | CG2 | ILE | 1 | 126 | -14.467 | 66.385 | 29.299 | 1.00 | 0.00 |
| ATOM | 1143 | CD1 | ILE | 1 | 126 | -11.753 | 67.296 | 30.873 | 1.00 | 0.00 |
| ATOM | 1144 | H | ILE | 1 | 126 | -13.135 | 64.303 | 32.601 | 1.00 | 0.00 |
| ATOM | 1145 | N | TYR | 1 | 127 | -14.624 | 62.715 | 30.636 | 1.00 | 0.00 |
| ATOM | 1146 | CA | TYR | 1 | 127 | -15.167 | 61.452 | 30.126 | 1.00 | 0.00 |
| ATOM | 1147 | C | TYR | 1 | 127 | -16.529 | 61.083 | 30.734 | 1.00 | 0.00 |
| ATOM | 1148 | O | TYR | 1 | 127 | -17.440 | 60.554 | 30.100 | 1.00 | 0.00 |
| ATOM | 1149 | CB | TYR | 1 | 127 | -14.051 | 60.272 | 30.134 | 1.00 | 0.00 |
| ATOM | 1150 | CG | TYR | 1 | 127 | -14.489 | 59.022 | 30.878 | 1.00 | 0.00 |
| ATOM | 1151 | CD1 | TYR | 1 | 127 | -15.254 | 58.078 | 30.129 | 1.00 | 0.00 |
| ATOM | 1152 | CD2 | TYR | 1 | 127 | -14.209 | 58.796 | 32.260 | 1.00 | 0.00 |
| ATOM | 1153 | CE1 | TYR | 1 | 127 | -15.911 | 56.995 | 30.838 | 1.00 | 0.00 |
| ATOM | 1154 | CE2 | TYR | 1 | 127 | -14.809 | 57.674 | 32.912 | 1.00 | 0.00 |
| ATOM | 1155 | CZ | TYR | 1 | 127 | -15.750 | 56.817 | 32.219 | 1.00 | 0.00 |
| ATOM | 1156 | OH | TYR | 1 | 127 | -16.381 | 55.818 | 32.877 | 1.00 | 0.00 |
| ATOM | 1157 | H | TYR | 1 | 127 | -13.751 | 62.624 | 31.115 | 1.00 | 0.00 |
| ATOM | 1158 | HH | TYR | 1 | 127 | -16.924 | 55.379 | 32.236 | 1.00 | 0.00 |
| ATOM | 1159 | N | GLN | 1 | 128 | -16.689 | 61.447 | 32.006 | 1.00 | 0.00 |
| ATOM | 1160 | CA | GLN | 1 | 128 | -17.972 | 61.076 | 32.613 | 1.00 | 0.00 |
| ATOM | 1161 | C | GLN | 1 | 128 | -18.820 | 62.307 | 32.767 | 1.00 | 0.00 |
| ATOM | 1162 | O | GLN | 1 | 128 | -19.700 | 62.437 | 33.627 | 1.00 | 0.00 |
| ATOM | 1163 | CB | GLN | 1 | 128 | -17.573 | 60.544 | 33.940 | 1.00 | 0.00 |
| ATOM | 1164 | CG | GLN | 1 | 128 | -18.401 | 59.339 | 34.361 | 1.00 | 0.00 |
| ATOM | 1165 | CD | GLN | 1 | 128 | -17.669 | 58.576 | 35.474 | 1.00 | 0.00 |
| ATOM | 1166 | OE1 | GLN | 1 | 128 | -17.437 | 59.077 | 36.587 | 1.00 | 0.00 |
| ATOM | 1067 | NE2 | GLN | 1 | 128 | -17.060 | 57.418 | 35.047 | 1.00 | 0.00 |
| ATOM | 1068 | H | GLN | 1 | 128 | -15.933 | 61.976 | 32.392 | 1.00 | 0.00 |
| ATOM | 1069 | 1HE2 | GLN | 1 | 128 | -17.400 | 56.974 | 34.218 | 1.00 | 0.00 |
| ATOM | 1070 | 2HE2 | GLN | 1 | 128 | -16.287 | 57.080 | 35.584 | 1.00 | 0.00 |

FIG. 1Z

| ATOM | 1171 | N    | THR | 1 | 129 | -18.610 | 63.261 | 31.790 | 1.00 | 0.00 |
| ATOM | 1172 | CA   | THR | 1 | 129 | -19.554 | 64.402 | 31.531 | 1.00 | 0.00 |
| ATOM | 1173 | C    | THR | 1 | 129 | -20.034 | 64.338 | 30.090 | 1.00 | 0.00 |
| ATOM | 1174 | O    | THR | 1 | 129 | -21.188 | 64.645 | 29.868 | 1.00 | 0.00 |
| ATOM | 1175 | CB   | THR | 1 | 129 | -18.694 | 65.689 | 31.759 | 1.00 | 0.00 |
| ATOM | 1176 | OG1  | THR | 1 | 129 | -17.843 | 65.533 | 32.883 | 1.00 | 0.00 |
| ATOM | 1177 | CG2  | THR | 1 | 129 | -19.575 | 66.877 | 31.994 | 1.00 | 0.00 |
| ATOM | 1178 | H    | THR | 1 | 129 | -17.822 | 63.069 | 31.205 | 1.00 | 0.00 |
| ATOM | 1179 | 1HG  | THR | 1 | 129 | -17.276 | 64.776 | 32.808 | 1.00 | 0.00 |
| ATOM | 1180 | N    | ASP | 1 | 130 | -19.100 | 63.839 | 29.242 | 1.00 | 0.00 |
| ATOM | 1181 | CA   | ASP | 1 | 130 | -19.272 | 63.530 | 27.815 | 1.00 | 0.00 |
| ATOM | 1182 | C    | ASP | 1 | 130 | -18.547 | 62.268 | 27.468 | 1.00 | 0.00 |
| ATOM | 1183 | O    | ASP | 1 | 130 | -17.360 | 62.026 | 27.412 | 1.00 | 0.00 |
| ATOM | 1184 | CB   | ASP | 1 | 130 | -18.822 | 64.757 | 26.978 | 1.00 | 0.00 |
| ATOM | 1185 | CG   | ASP | 1 | 130 | -18.897 | 64.631 | 25.454 | 1.00 | 0.00 |
| ATOM | 1186 | OD1  | ASP | 1 | 130 | -19.920 | 64.947 | 24.888 | 1.00 | 0.00 |
| ATOM | 1187 | OD2  | ASP | 1 | 130 | 017.905 | 64.242 | 24.882 | 1.00 | 0.00 |
| ATOM | 1188 | H    | ASP | 1 | 130 | -18.255 | 63.427 | 29.582 | 1.00 | 0.00 |
| ATOM | 1189 | N    | ARG | 1 | 131 | -19.410 | 61.274 | 27.309 | 1.00 | 0.00 |
| ATOM | 1190 | CA   | ARG | 1 | 131 | -18.935 | 59.959 | 26.768 | 1.00 | 0.00 |
| ATOM | 1191 | C    | ARG | 1 | 131 | -18.469 | 60.154 | 25.366 | 1.00 | 0.00 |
| ATOM | 1192 | O    | ARG | 1 | 131 | -17.594 | 59.446 | 24.815 | 1.00 | 0.00 |
| ATOM | 1193 | CB   | ARG | 1 | 131 | -20.032 | 58.855 | 26.756 | 1.00 | 0.00 |
| ATOM | 1194 | CG   | ARG | 1 | 131 | -20.416 | 58.478 | 28.193 | 1.00 | 0.00 |
| ATOM | 1195 | CD   | ARG | 1 | 131 | -19.194 | 57.782 | 28.955 | 1.00 | 0.00 |
| ATOM | 1196 | NE   | ARG | 1 | 131 | -18.986 | 56.441 | 28.423 | 1.00 | 0.00 |
| ATOM | 1197 | CZ   | ARG | 1 | 131 | -19.071 | 55.351 | 29.184 | 1.00 | 0.00 |
| ATOM | 1198 | NH1  | ARG | 1 | 131 | -18.900 | 54.185 | 28.671 | 1.00 | 0.00 |
| ATOM | 1199 | NH2  | ARG | 1 | 131 | -19.376 | 55.517 | 30.503 | 1.00 | 0.00 |
| ATOM | 1200 | H    | ARG | 1 | 131 | -20.369 | 61.548 | 27.370 | 1.00 | 0.00 |
| ATOM | 1201 | HE   | ARG | 1 | 131 | -18.632 | 56.469 | 27.488 | 1.00 | 0.00 |
| ATOM | 1202 | 1HH1 | ARG | 1 | 131 | -18.956 | 53.332 | 29.191 | 1.00 | 0.00 |
| ATOM | 1203 | 2HH1 | ARG | 1 | 131 | -18.792 | 54.024 | 27.690 | 1.00 | 0.00 |
| ATOM | 1204 | 1HH2 | ARG | 1 | 131 | -19.481 | 54.718 | 31.095 | 1.00 | 0.00 |
| ATOM | 1205 | 2HH2 | ARG | 1 | 131 | -19.542 | 56.412 | 30.918 | 1.00 | 0.00 |
| ATOM | 1206 | N    | GLU | 1 | 132 | -19.073 | 61.146 | 24.679 | 1.00 | 0.00 |
| ATOM | 1207 | CA   | GLU | 1 | 132 | -19.097 | 61.123 | 23.223 | 1.00 | 0.00 |
| ATOM | 1208 | C    | GLU | 1 | 132 | -17.704 | 61.256 | 22.550 | 1.00 | 0.00 |
| ATOM | 1209 | O    | GLU | 1 | 132 | -17.303 | 60.476 | 21.676 | 1.00 | 0.00 |
| ATOM | 1210 | CB   | GLU | 1 | 132 | -20.158 | 62.165 | 22.829 | 1.00 | 0.00 |
| ATOM | 1211 | CG   | GLU | 1 | 132 | -20.663 | 62.490 | 21.437 | 1.00 | 0.00 |
| ATOM | 1212 | CD   | GLU | 1 | 132 | -19.538 | 62.468 | 20.507 | 1.00 | 0.00 |
| ATOM | 1213 | OE1  | GLU | 1 | 132 | -18.751 | 63.417 | 20.464 | 1.00 | 0.00 |
| ATOM | 1214 | OE2  | GLU | 1 | 132 | -19.328 | 61.449 | 19.842 | 1.00 | 0.00 |
| ATOM | 1215 | H    | GLU | 1 | 132 | -19.447 | 61.944 | 25.151 | 1.00 | 0.00 |

FIG. 1AA

| ATOM | 1216 | N | LYS | 1 | 133 | -16.973 | 62.276 | 23.084 | 1.00 | 0.00 |
|---|---|---|---|---|---|---|---|---|---|---|
| ATOM | 1217 | CA | LYS | 1 | 133 | -15.616 | 62.452 | 22.586 | 1.00 | 0.00 |
| ATOM | 1218 | C | LYS | 1 | 133 | -14.629 | 61.391 | 22.856 | 1.00 | 0.00 |
| ATOM | 1219 | O | LYS | 1 | 133 | -13.837 | 60.980 | 22.044 | 1.00 | 0.00 |
| ATOM | 1220 | CB | LYS | 1 | 133 | -15.115 | 63.846 | 22.950 | 1.00 | 0.00 |
| ATOM | 1221 | CG | LYS | 1 | 133 | -15.678 | 64.917 | 22.035 | 1.00 | 0.00 |
| ATOM | 1222 | CD | LYS | 1 | 133 | -16.243 | 66.106 | 22.825 | 1.00 | 0.00 |
| ATOM | 1223 | CE | LYS | 1 | 133 | -17.623 | 66.499 | 22.255 | 1.00 | 0.00 |
| ATOM | 1224 | NZ | LYS | 1 | 133 | -18.680 | 65.449 | 22.4551 | 1.00 | 0.00 |
| ATOM | 1225 | H | LYS | 1 | 133 | -17.198 | 62.759 | 23.930 | 1.00 | 0.00 |
| ATOM | 1226 | 1HZ | LYS | 1 | 133 | -18.725 | 64.799 | 21.645 | 1.00 | 0.00 |
| ATOM | 1227 | 2HZ | LYS | 1 | 133 | -18.439 | 64.912 | 23.313 | 1.00 | 0.00 |
| ATOM | 1228 | 3HZ | LYS | 1 | 133 | -19.642 | 65.786 | 22.663 | 1.00 | 0.00 |
| ATOM | 1229 | N | TYR | 1 | 134 | -14.790 | 60.794 | 24.068 | 1.00 | 0.00 |
| ATOM | 1230 | CA | TYR | 1 | 134 | -14.077 | 59.548 | 24.365 | 1.00 | 0.00 |
| ATOM | 1231 | C | TYR | 1 | 134 | -14.477 | 58.281 | 23.495 | 1.00 | 0.00 |
| ATOM | 1232 | O | TYR | 1 | 134 | -13.564 | 57.463 | 23.191 | 1.00 | 0.00 |
| ATOM | 1233 | CB | TYR | 1 | 134 | -14.163 | 59.285 | 25.901 | 1.00 | 0.00 |
| ATOM | 1234 | CG | TYR | 1 | 134 | -13.902 | 57.807 | 26.279 | 1.00 | 0.00 |
| ATOM | 1235 | CD1 | TYR | 1 | 134 | -12.616 | 57.238 | 26.234 | 1.00 | 0.00 |
| ATOM | 1236 | CD2 | TYR | 1 | 143 | -14.952 | 56.954 | 26.703 | 1.00 | 0.00 |
| ATOM | 1237 | CE1 | TYR | 1 | 134 | -12.308 | 55.950 | 26.691 | 1.00 | 0.00 |
| ATOM | 1238 | CE2 | TYR | 1 | 134 | -14.739 | 55.641 | 27.144 | 1.00 | 0.00 |
| ATOM | 1239 | CZ | TYR | 1 | 134 | -13.388 | 55.147 | 27.137 | 1.00 | 0.00 |
| ATOM | 1240 | OH | TYR | 1 | 134 | -13.089 | 53.833 | 27.509 | 1.00 | 0.00 |
| ATOM | 1241 | H | TYR | 1 | 134 | -15.605 | 61.016 | 24.604 | 1.00 | 0.00 |
| ATOM | 1242 | HH | TYR | 1 | 134 | -12.629 | 53.955 | 28.329 | 1.00 | 0.00 |
| ATOM | 1243 | N | ASN | 1 | 135 | -15.732 | 58.290 | 23.026 | 1.00 | 0.00 |
| ATOM | 1244 | CA | ASN | 1 | 135 | -16.023 | 57.578 | 21.793 | 1.00 | 0.00 |
| ATOM | 1245 | C | ASN | 1 | 135 | -15.345 | 58.003 | 20.446 | 1.00 | 0.00 |
| ATOM | 1246 | O | ASN | 1 | 135 | -16.007 | 57.968 | 19.385 | 1.00 | 0.00 |
| ATOM | 1247 | CB | ASN | 1 | 135 | -17.458 | 57.139 | 21.710 | 1.00 | 0.00 |
| ATOM | 1248 | CG | ASN | 1 | 135 | -17,585 | 55.762 | 22.262 | 1.00 | 0.00 |
| ATOM | 1249 | OD1 | ASN | 1 | 135 | -17.810 | 55.462 | 23.457 | 1.00 | 0.00 |
| ATOM | 1250 | ND2 | ASN | 1 | 135 | -17.359 | 54.819 | 21.344 | 1.00 | 0.00 |
| ATOM | 1251 | H | ASN | 1 | 135 | -16.422 | 58.886 | 23.436 | 1.00 | 0.00 |
| ATOM | 1252 | 1HD2 | ASN | 1 | 135 | -17.077 | 54.977 | 20.398 | 1.00 | 0.00 |
| ATOM | 1253 | 2HD2 | ASN | 1 | 135 | -17.430 | 53.873 | 21.660 | 1.00 | 0.00 |
| ATOM | 1254 | N | ARG | 1 | 136 | -14.053 | 58.370 | 20.478 | 1.00 | 0.00 |
| ATOM | 1255 | CA | ARG | 1 | 136 | -13.385 | 58.938 | 19.318 | 1.00 | 0.00 |
| ATOM | 1256 | C | ARG | 1 | 136 | -11.907 | 59.136 | 19.706 | 1.00 | 0.00 |
| ATOM | 1257 | O | ARG | 1 | 136 | -11.120 | 58.192 | 19.624 | 1.00 | 0.00 |
| ATOM | 1258 | CB | ARG | 1 | 136 | -13.963 | 60.323 | 18.860 | 1.00 | 0.00 |
| ATOM | 1259 | CG | ARG | 1 | 136 | -13.759 | 60.585 | 17.391 | 1.00 | 0.00 |
| ATOM | 1260 | CD | ARG | 1 | 136 | -15.027 | 60.276 | 16.539 | 1.00 | 0.00 |

FIG. 1BB

| | | | | | | | | | |
|---|---|---|---|---|---|---|---|---|---|
| ATOM | 1261 | NE | ARG | 1 | 136 | -16.001 | 61.343 | 16.710 | 1.00 0.00 |
| ATOM | 1262 | CZ | ARG | 1 | 136 | -16.953 | 61.385 | 17.722 | 1.00 0.00 |
| ATOM | 1263 | NH1 | ARG | 1 | 136 | -17.634 | 62.501 | 17.758 | 1.00 0.00 |
| ATOM | 1264 | NH2 | ARG | 1 | 136 | -17.160 | 60.427 | 18.572 | 1.00 0.00 |
| ATOM | 1265 | H | ARG | 1 | 136 | -13.577 | 58.270 | 21.352 | 1.00 0.00 |
| ATOM | 1266 | HE | ARG | 1 | 136 | -15.978 | 62.141 | 16.108 | 1.00 0.00 |
| ATOM | 1267 | 1HH1 | ARG | 1 | 136 | -18.194 | 62.691 | 18.565 | 1.00 0.00 |
| ATOM | 1268 | 2HH1 | ARG | 1 | 136 | -17.585 | 63.094 | 16.955 | 1.00 0.00 |
| ATOM | 1269 | 1HH2 | ARG | 1 | 136 | -17.955 | 60.445 | 19.178 | 1.00 0.00 |
| ATOM | 1270 | 2HH2 | ARG | 1 | 136 | -16.527 | 59.655 | 18.631 | 1.00 0.00 |
| ATOM | 1271 | N | ILE | 1 | 137 | -11.553 | 60.299 | 20.250 | 1.00 0.00 |
| ATOM | 1272 | CA | ILE | 1 | 137 | -10.216 | 60.181 | 20.894 | 1.00 0.00 |
| ATOM | 1273 | C | ILE | 1 | 137 | -10.249 | 59.245 | 22.086 | 1.00 0.00 |
| ATOM | 1274 | O | ILE | 1 | 137 | -10.876 | 59.502 | 23.085 | 1.00 0.00 |
| ATOM | 1275 | CB | ILE | 1 | 137 | -9.737 | 61.669 | 21.177 | 1.00 0.00 |
| ATOM | 1276 | CG1 | ILE | 1 | 137 | -10.160 | 62.400 | 22.437 | 1.00 0.00 |
| ATOM | 1277 | CG2 | ILE | 1 | 137 | -10.058 | 62.553 | 19.908 | 1.00 0.00 |
| ATOM | 1278 | CD1 | ILE | 1 | 137 | -9.379 | 63.684 | 22.863 | 1.00 0.00 |
| ATOM | 1279 | H | ILE | 1 | 137 | -12.189 | 61.029 | 20.500 | 1.00 0.00 |
| ATOM | 1280 | N | ALA | 1 | 138 | -9.665 | 58.091 | 21.783 | 1.00 0.00 |
| ATOM | 1281 | CA | ALA | 1 | 138 | -9.599 | 56.705 | 22.426 | 1.00 0.00 |
| ATOM | 1282 | C | ALA | 1 | 138 | -10.195 | 55.649 | 21.536 | 1.00 0.00 |
| ATOM | 1283 | O | ALA | 1 | 138 | -9.601 | 54.689 | 21.054 | 1.00 0.00 |
| ATOM | 1284 | CB | ALA | 1 | 138 | -10.297 | 56.767 | 23.804 | 1.00 0.00 |
| ATOM | 1285 | H | ALA | 1 | 138 | -9.100 | 58.150 | 20.960 | 1.00 0.00 |
| ATOM | 1286 | N | ARG | 1 | 139 | -11.487 | 55.821 | 21.280 | 1.00 0.00 |
| ATOM | 1287 | CA | ARG | 1 | 139 | -11.974 | 55.035 | 20.159 | 1.00 0.00 |
| ATOM | 1288 | C | ARG | 1 | 139 | -11.531 | 55.522 | 18.757 | 1.00 0.00 |
| ATOM | 1289 | O | ARG | 1 | 139 | -12.365 | 55.995 | 17.960 | 1.00 0.00 |
| ATOM | 1290 | CB | ARG | 1 | 139 | -13.446 | 54.877 | 20.345 | 1.00 0.00 |
| ATOM | 1291 | CG | ARG | 1 | 139 | -14.037 | 53.544 | 20.350 | 1.00 0.00 |
| ATOM | 1292 | CD | ARG | 1 | 139 | -13.777 | 52.739 | 19.100 | 1.00 0.00 |
| ATOM | 1293 | NE | ARG | 1 | 139 | -13.294 | 51.422 | 19.446 | 1.00 0.00 |
| ATOM | 1294 | CZ | ARG | 1 | 139 | -14.070 | 50.451 | 19.933 | 1.00 0.00 |
| ATOM | 1295 | NH1 | ARG | 1 | 139 | -15.376 | 50.557 | 20.176 | 1.00 0.00 |
| ATOM | 1296 | NH2 | ARG | 1 | 139 | -13.546 | 49.286 | 20.238 | 1.00 0.00 |
| ATOM | 1297 | H | ARG | 1 | 139 | -11.953 | 56.599 | 21.701 | 1.00 0.00 |
| ATOM | 1298 | HE | ARG | 1 | 139 | -12.325 | 51.217 | 19.213 | 1.00 0.00 |
| ATOM | 1299 | 1HH1 | ARG | 1 | 139 | -15.852 | 49.744 | 20.511 | 1.00 0.00 |
| ATOM | 1300 | 2HH1 | ARG | 1 | 139 | -15.778 | 51.473 | 20.172 | 1.00 0.00 |
| ATOM | 1301 | 1HH2 | ARG | 1 | 139 | -14.068 | 48.524 | 20.623 | 1.00 0.00 |
| ATOM | 1302 | 2HH2 | ARG | 1 | 139 | -12.550 | 49.203 | 20.209 | 1.00 0.00 |
| ATOM | 1303 | N | GLU | 1 | 140 | -10.248 | 55.319 | 18.431 | 1.00 0.00 |
| ATOM | 1304 | CA | GLU | 1 | 140 | -9.561 | 55.842 | 17.254 | 1.00 0.00 |
| ATOM | 1305 | C | GLU | 1 | 140 | -8.281 | 54.950 | 17.238 | 1.00 0.00 |

FIG. 1CC

| ATOM | 1306 | O | GLU | 1 | 140 | -8.151 | 54.134 | 16.315 | 1.00 | 0.00 |
| ATOM | 1307 | CB | GLU | 1 | 140 | -9.381 | 57.331 | 17.443 | 1.00 | 0.00 |
| ATOM | 1308 | CG | GLU | 1 | 140 | -9.055 | 58.269 | 16.321 | 1.00 | 0.00 |
| ATOM | 1309 | CD | GLU | 1 | 140 | -7.581 | 57.782 | 15.971 | 1.00 | 0.00 |
| ATOM | 1310 | OE1 | GLU | 1 | 140 | -6.649 | 57.991 | 16.665 | 1.00 | 0.00 |
| ATOM | 1311 | OE2 | GLU | 1 | 140 | -7.440 | 57.213 | 14.940 | 1.00 | 0.00 |
| ATOM | 1312 | H | GLU | 1 | 140 | -9.824 | 54.778 | 19.157 | 1.00 | 0.00 |
| ATOM | 1313 | N | TRP | 1 | 141 | -7.528 | 55.060 | 18.298 | 1.00 | 0.00 |
| ATOM | 1314 | CA | TRP | 1 | 141 | -6.370 | 54.173 | 18.571 | 1.00 | 0.00 |
| ATOM | 1315 | C | TRP | 1 | 141 | -6.737 | 52.782 | 18.944 | 1.00 | 0.00 |
| ATOM | 1316 | O | TRP | 1 | 141 | -5.982 | 51.968 | 19.452 | 1.00 | 0.00 |
| ATOM | 1317 | CB | TRP | 1 | 141 | -5.483 | 54.663 | 19.722 | 1.00 | 0.00 |
| ATOM | 1318 | CG | TRP | 1 | 141 | -4.774 | 55.962 | 19.326 | 1.00 | 0.00 |
| ATOM | 1319 | CD1 | TRP | 1 | 141 | -3.685 | 56.131 | 18.409 | 1.00 | 0.00 |
| ATOM | 1320 | CD2 | TRP | 1 | 141 | -5.095 | 57.289 | 19.700 | 1.00 | 0.00 |
| ATOM | 1321 | NE1 | TRP | 1 | 141 | -3.327 | 57.468 | 18.247 | 1.00 | 0.00 |
| ATOM | 1322 | CE2 | TRP | 1 | 141 | -4.213 | 58.240 | 19.050 | 1.00 | 0.00 |
| ATOM | 1323 | CE3 | TRP | 1 | 141 | -6.038 | 57.792 | 20.591 | 1.00 | 0.00 |
| ATOM | 1324 | CZ2 | TRP | 1 | 141 | -4.413 | 59.642 | 19.300 | 1.00 | 0.00 |
| ATOM | 1325 | CZ3 | TRP | 1 | 141 | -6.247 | 59.169 | 20.882 | 1.00 | 0.00 |
| ATOM | 1326 | CH2 | TRP | 1 | 141 | -5.415 | 60.068 | 20.154 | 1.00 | 0.00 |
| ATOM | 1327 | H | TRP | 1 | 141 | -7.623 | 55.892 | 18.845 | 1.00 | 0.00 |
| ATOM | 1328 | 1HE | TRP | 1 | 141 | -2.570 | 57.837 | 17.746 | 1.00 | 0.00 |
| ATOM | 1329 | N | THR | 1 | 142 | -7.945 | 52.388 | 18.669 | 1.00 | 0.00 |
| ATOM | 1330 | CA | THR | 1 | 142 | -8.470 | 51.003 | 18.796 | 1.00 | 0.00 |
| ATOM | 1331 | C | THR | 1 | 142 | -8.785 | 50.384 | 17.443 | 1.00 | 0.00 |
| ATOM | 1332 | O | THR | 1 | 142 | -8.951 | 49.195 | 17.303 | 1.00 | 0.00 |
| ATOM | 1333 | CB | THR | 1 | 142 | -9.836 | 51.112 | 19.635 | 1.00 | 0.00 |
| ATOM | 1334 | OG1 | THR | 1 | 142 | -10.085 | 52.512 | 20.129 | 1.00 | 0.00 |
| ATOM | 1335 | CG2 | THR | 1 | 142 | -9.646 | 50.189 | 20.902 | 1.00 | 0.00 |
| ATOM | 1336 | H | THR | 1 | 142 | -8.557 | 53.070 | 18.268 | 1.00 | 0.00 |
| ATOM | 1337 | 1HG | THR | 1 | 142 | -9.297 | 52.761 | 20.593 | 1.00 | 0.00 |
| ATOM | 1338 | N | GLN | 1 | 143 | -8.798 | 51.237 | 16.420 | 1.00 | 0.00 |
| ATOM | 1339 | CA | GLN | 1 | 143 | -8.800 | 50.759 | 15.056 | 1.00 | 0.00 |
| ATOM | 1340 | C | GLN | 1 | 143 | -7.468 | 50.990 | 14.393 | 1.00 | 0.00 |
| ATOM | 1341 | O | GLN | 1 | 143 | -6.836 | 49.990 | 14.069 | 1.00 | 0.00 |
| ATOM | 1342 | CB | GLN | 1 | 143 | -9.874 | 51.493 | 14.234 | 1.00 | 0.00 |
| ATOM | 1343 | CG | GLN | 1 | 143 | -10.095 | 50.582 | 13.074 | 1.00 | 0.00 |
| ATOM | 1344 | CD | GLN | 1 | 143 | -10.628 | 51.426 | 11.972 | 1.00 | 0.00 |
| ATOM | 1345 | OE1 | GLN | 1 | 143 | -11.716 | 51.960 | 12.091 | 1.00 | 0.00 |
| ATOM | 1346 | NE2 | GLN | 1 | 143 | -9.832 | 51.593 | 10.953 | 1.00 | 0.00 |
| ATOM | 1347 | H | GLN | 1 | 143 | -8.441 | 52.158 | 16.577 | 1.00 | 0.00 |
| ATOM | 1348 | 1HE2 | GLN | 1 | 143 | -8.858 | 51.392 | 10.856 | 1.00 | 0.00 |
| ATOM | 1349 | 2HE2 | GLN | 1 | 143 | -10.262 | 52.137 | 10.232 | 1.00 | 0.00 |
| ATOM | 1350 | N | LYS | 1 | 144 | -7.185 | 52.353 | 14.272 | 1.00 | 0.00 |

FIG. 1DD

| ATOM | 1351 | CA | LYS | 1 | 144 | -5.872 | 52.774 | 13.923 | 1.00 | 0.00 |
| ATOM | 1352 | C | LYS | 1 | 144 | -4.944 | 52.505 | 15.064 | 1.00 | 0.00 |
| ATOM | 1353 | O | LYS | 1 | 144 | -4.948 | 53.182 | 16.090 | 1.00 | 0.00 |
| ATOM | 1354 | CB | LYS | 1 | 144 | -6.052 | 54.219 | 13.415 | 1.00 | 0.00 |
| ATOM | 1355 | CG | LYS | 1 | 144 | -4.756 | 54.831 | 12.839 | 1.00 | 0.00 |
| ATOM | 1356 | CD | LYS | 1 | 144 | -4.529 | 56.258 | 13.351 | 1.00 | 0.00 |
| ATOM | 1357 | CE | LYS | 1 | 144 | -4.289 | 56.135 | 14.821 | 1.00 | 0.00 |
| ATOM | 1358 | NZ | LYS | 1 | 144 | -4.298 | 57.465 | 15.486 | 1.00 | 0.00 |
| ATOM | 1359 | H | LYS | 1 | 144 | -7.735 | 53.032 | 14.760 | 1.00 | 0.00 |
| ATOM | 1360 | 1HZ | LYS | 1 | 144 | -5.272 | 57.787 | 15.657 | 1.00 | 0.00 |
| ATOM | 1361 | 2HZ | LYS | 1 | 144 | -3.709 | 57.497 | 16.342 | 1.00 | 0.00 |
| ATOM | 1362 | 3HZ | LYS | 1 | 144 | -3.674 | 58.052 | 14.895 | 1.00 | 0.00 |
| ATOM | 1363 | N | TYR | 1 | 145 | -4.035 | 51.523 | 14.725 | 1.00 | 0.00 |
| ATOM | 1364 | CA | TYR | 1 | 145 | -2.783 | 51.563 | 15.405 | 1.00 | 0.00 |
| ATOM | 1365 | C | TYR | 1 | 145 | -1.705 | 51.911 | 14.373 | 1.00 | 0.00 |
| ATOM | 1366 | O | TYR | 1 | 145 | -1.262 | 51.077 | 13.622 | 1.00 | 0.00 |
| ATOM | 1367 | CB | TYR | 1 | 145 | -2.651 | 50.166 | 16.073 | 1.00 | 0.00 |
| ATOM | 1368 | CG | TYR | 1 | 145 | -1.338 | 50.008 | 16.760 | 1.00 | 0.00 |
| ATOM | 1369 | CD1 | TYR | 1 | 145 | -1.119 | 50.509 | 18.043 | 1.00 | 0.00 |
| ATOM | 1370 | CD2 | TYR | 1 | 145 | -0.302 | 49.394 | 16.035 | 1.00 | 0.00 |
| ATOM | 1371 | CE1 | TYR | 1 | 145 | 0.150 | 50.465 | 18.579 | 1.00 | 0.00 |
| ATOM | 1372 | CE2 | TYR | 1 | 145 | 0.972 | 49.409 | 16.589 | 1.00 | 0.00 |
| ATOM | 1373 | CZ | TYR | 1 | 145 | 1.210 | 49.922 | 17.847 | 1.00 | 0.00 |
| ATOM | 1374 | OH | TYR | 1 | 145 | 2.486 | 49.934 | 18.410 | 1.00 | 0.00 |
| ATOM | 1375 | H | TYR | 1 | 145 | -4.122 | 50.802 | 14.038 | 1.00 | 0.00 |
| ATOM | 1376 | HH | TYR | 1 | 145 | 2.907 | 50.776 | 18.294 | 1.00 | 0.00 |
| ATOM | 1377 | N | ALA | 1 | 146 | -1.219 | 53.200 | 14.453 | 1.00 | 0.00 |
| ATOM | 1378 | CA | ALA | 1 | 146 | -0.018 | 53.540 | 13.627 | 1.00 | 0.00 |
| ATOM | 1379 | C | ALA | 1 | 146 | 0.585 | 54.832 | 14.174 | 1.00 | 0.00 |
| ATOM | 1380 | O | ALA | 1 | 146 | 1.508 | 54.792 | 14.958 | 1.00 | 0.00 |
| ATOM | 1381 | CB | ALA | 1 | 146 | -0.347 | 53.708 | 12.163 | 1.00 | 0.00 |
| ATOM | 1382 | H | ALA | 1 | 146 | -1.694 | 53.960 | 14.896 | 1.00 | 0.00 |
| ATOM | 1383 | N | MET | 1 | 147 | 0.146 | 55.965 | 13.712 | 1.00 | 0.00 |
| ATOM | 1384 | CA | MET | 1 | 147 | 0.072 | 57.199 | 14.504 | 1.00 | 0.00 |
| ATOM | 1385 | C | MET | 1 | 147 | -1.165 | 57.157 | 15.439 | 1.00 | 0.00 |
| ATOM | 1386 | O | MET | 1 | 147 | -1.746 | 58.134 | 15.774 | 1.00 | 0.00 |
| ATOM | 1387 | CB | MET | 1 | 147 | 0.219 | 58.444 | 13.697 | 1.00 | 0.00 |
| ATOM | 1388 | CG | MET | 1 | 147 | -0.769 | 58.439 | 12.499 | 1.00 | 0.00 |
| ATOM | 1389 | SD | MET | 1 | 147 | -0.431 | 59.820 | 11.346 | 1.00 | 0.00 |
| ATOM | 1390 | CE | MET | 1 | 147 | -2.099 | 59.928 | 10.616 | 1.00 | 0.00 |
| ATOM | 1391 | OXT | MET | 1 | 147 | -1.521 | 56.064 | 15.926 | 1.00 | 0.00 |
| ATOM | 1392 | H | MET | 1 | 147 | -0.461 | 55.994 | 12.919 | 1.00 | 0.00 |
| END | | | | | | | | | | |

FIG. 1EE

| ATOM | 1 | N | CYS *1 | 85 | 12.813 | -15.194 | 42.441 | 1.00 | 0.00 |
|------|---|---|--------|----|--------|---------|--------|------|------|
| ATOM | 2 | H | CYS *1 | 85 | 13.027 | -15.873 | 41.738 | 1.00 | 0.00 |
| ATOM | 3 | CA | CYS *1 | 85 | 13.822 | -14.593 | 43.296 | 1.00 | 0.00 |
| ATOM | 4 | CB | CYS *1 | 85 | 14.815 | -15.616 | 43.734 | 1.00 | 0.00 |
| ATOM | 5 | SG | CYS *1 | 85 | 15.117 | -15.447 | 45.437 | 1.00 | 0.00 |
| ATOM | 6 | C | CYS *1 | 85 | 14.478 | -13.341 | 42.778 | 1.00 | 0.00 |
| ATOM | 7 | O | CYS *1 | 85 | 13.994 | -12.195 | 43.023 | 1.00 | 0.00 |
| ATOM | 8 | N | LEU 1 | 86 | 15.596 | -13.553 | 42.021 | 1.00 | 0.00 |
| ATOM | 9 | CA | LEU 1 | 86 | 16.482 | -12.490 | 41.469 | 1.00 | 0.00 |
| ATOM | 10 | C | LEU 1 | 86 | 17.155 | -11.557 | 42.453 | 1.00 | 0.00 |
| ATOM | 11 | O | LEU 1 | 86 | 16.664 | -11.390 | 43.514 | 1.00 | 0.00 |
| ATOM | 12 | CB | LEU 1 | 86 | 15.850 | -11.805 | 40.281 | 1.00 | 0.00 |
| ATOM | 13 | CG | LEU 1 | 86 | 14.624 | -12.437 | 39.580 | 1.00 | 0.00 |
| ATOM | 14 | CD1 | LEU 1 | 86 | 14.040 | -11.515 | 38.482 | 1.00 | 0.00 |
| ATOM | 15 | CD2 | LEU 1 | 86 | 14.916 | -13.795 | 38.925 | 1.00 | 0.00 |
| ATOM | 16 | H | LEU 1 | 86 | 15.932 | -14.493 | 41.961 | 1.00 | 0.00 |
| ATOM | 17 | N | ASP 1 | 87 | 18.301 | -10.942 | 42.020 | 1.00 | 0.00 |
| ATOM | 18 | CA | ASP 1 | 87 | 18.887 | -9.697 | 42.577 | 1.00 | 0.00 |
| ATOM | 19 | C | ASP 1 | 87 | 17.933 | -8.538 | 42.215 | 1.00 | 0.00 |
| ATOM | 20 | O | ASP 1 | 87 | 17.603 | -7.688 | 42.977 | 1.00 | 0.00 |
| ATOM | 21 | CB | ASP 1 | 87 | 20.280 | -9.473 | 41.980 | 1.00 | 0.00 |
| ATOM | 22 | CG | ASP 1 | 87 | 20.280 | -9.437 | 40.434 | 1.00 | 0.00 |
| ATOM | 23 | OD1 | ASP 1 | 87 | 21.191 | -8.936 | 39.856 | 1.00 | 0.00 |
| ATOM | 24 | OD2 | ASP 1 | 87 | 19.409 | -9.977 | 39.792 | 1.00 | 0.00 |
| ATOM | 25 | H | ASP 1 | 87 | 18.468 | -11.284 | 41.095 | 1.00 | 0.00 |
| ATOM | 26 | N | ILE 1 | 88 | 17.532 | -8.458 | 40.922 | 1.00 | 0.00 |
| ATOM | 27 | CA | ILE 1 | 88 | 16.874 | -7.254 | 40.484 | 1.00 | 0.00 |
| ATOM | 28 | C | ILE 1 | 88 | 15.486 | -7.061 | 40.987 | 1.00 | 0.00 |
| ATOM | 29 | O | ILE 1 | 88 | 14.834 | -5.995 | 40.819 | 1.00 | 0.00 |
| ATOM | 30 | CB | ILE 1 | 88 | 16.911 | -7.193 | 38.904 | 1.00 | 0.00 |
| ATOM | 31 | CG1 | ILE 1 | 88 | 16.078 | -8.320 | 38.291 | 1.00 | 0.00 |
| ATOM | 32 | CG2 | ILE 1 | 88 | 18.322 | -7.055 | 38.472 | 1.00 | 0.00 |
| ATOM | 33 | CD | ILE 1 | 88 | 14.676 | -8.014 | 37.765 | 1.00 | 0.00 |
| ATOM | 34 | H | ILE 1 | 88 | 17.739 | -9.251 | 40.349 | 1.00 | 0.00 |
| ATOM | 35 | N | ARG 1 | 90 | 14.426 | -7.619 | 44.251 | 1.00 | 0.00 |
| ATOM | 36 | CA | ARG 1 | 90 | 14.634 | -7.627 | 45.688 | 1.00 | 0.00 |
| ATOM | 37 | C | ARG 1 | 90 | 15.897 | -6.845 | 46.216 | 1.00 | 0.00 |
| ATOM | 38 | O | ARG 1 | 90 | 15.818 | -5.995 | 47.079 | 1.00 | 0.00 |
| ATOM | 39 | CB | ARG 1 | 90 | 14.624 | -9.055 | 46.305 | 1.00 | 0.00 |
| ATOM | 40 | CG | ARG 1 | 90 | 15.765 | -10.003 | 46.039 | 1.00 | 0.00 |
| ATOM | 41 | CD | ARG 1 | 90 | 15.221 | -11.397 | 46.218 | 1.00 | 0.00 |
| ATOM | 42 | NE | ARG 1 | 90 | 14.864 | -11.584 | 47.622 | 1.00 | 0.00 |
| ATOM | 43 | CZ | ARG 1 | 90 | 13.976 | -12.617 | 47.838 | 1.00 | 0.00 |
| ATOM | 44 | NH1 | ARG 1 | 90 | 13.824 | -13.004 | 49.063 | 1.00 | 0.00 |
| ATOM | 45 | NH2 | ARG 1 | 90 | 13.426 | -13.227 | 46.779 | 1.00 | 0.00 |

FIG. 3A

| ATOM | 46 | H | ARG | 1 | 90 | 14.907 | -6.934 | 43.703 | 1.00 | 0.00 |
| ATOM | 47 | HE | ARG | 1 | 90 | 15.187 | -11.015 | 48.378 | 1.00 | 0.00 |
| ATOM | 48 | 1HH1 | ARG | 1 | 90 | 13.264 | -13.807 | 49.262 | 1.00 | 0.00 |
| ATOM | 49 | 2HH1 | ARG | 1 | 90 | 14.153 | -12.435 | 49.817 | 1.00 | 0.00 |
| ATOM | 50 | 2HH1 | ARG | 1 | 90 | 12.658 | -13.824 | 47.013 | 1.00 | 0.00 |
| ATOM | 51 | 2HH2 | ARG | 1 | 90 | 13.676 | -13.086 | 45.821 | 1.00 | 0.00 |
| ATOM | 52 | N | SER | 1 | 91 | 17.097 | -7.261 | 45.695 | 1.00 | 0.00 |
| ATOM | 53 | CA | SER | 1 | 91 | 18.257 | -6.643 | 46.299 | 1.00 | 0.00 |
| ATOM | 54 | C | SER | 1 | 91 | 19.180 | -5.852 | 45.357 | 1.00 | 0.00 |
| ATOM | 55 | O | SER | 1 | 91 | 20.364 | -5.736 | 45.486 | 1.00 | 0.00 |
| ATOM | 56 | CB | SER | 1 | 91 | 19.094 | -7.651 | 47.083 | 1.00 | 0.00 |
| ATOM | 57 | OG | SER | 1 | 91 | 18.260 | -8.522 | 47.886 | 1.00 | 0.00 |
| ATOM | 58 | H | SER | 1 | 91 | 17.222 | -7.822 | 44.876 | 1.00 | 0.00 |
| ATOM | 59 | HG | SER | 1 | 91 | 17.859 | -7.970 | 48.544 | 1.00 | 0.00 |
| ATOM | 60 | N | LEU | 1 | 109 | 18.852 | -18.359 | 38.255 | 1.00 | 0.00 |
| ATOM | 61 | CA | LEU | 1 | 109 | 18.365 | -18.942 | 39.568 | 1.00 | 0.00 |
| ATOM | 62 | C | LEU | 1 | 109 | 17.179 | -19.841 | 39.495 | 1.00 | 0.00 |
| ATOM | 63 | O | LEU | 1 | 109 | 16.540 | -20.333 | 40.413 | 1.00 | 0.00 |
| ATOM | 64 | CB | LEU | 1 | 109 | 18.387 | -17.901 | 40.725 | 1.00 | 0.00 |
| ATOM | 65 | CG | LEU | 1 | 109 | 19.746 | -17.216 | 40.897 | 1.00 | 0.00 |
| ATOM | 66 | CD1 | LEU | 1 | 109 | 19.834 | -15.819 | 40.391 | 1.00 | 0.00 |
| ATOM | 67 | CD2 | LEU | 1 | 109 | 20.454 | -17.598 | 42.195 | 1.00 | 0.00 |
| ATOM | 68 | H | LEU | 1 | 109 | 18.274 | -17.735 | 37.728 | 1.00 | 0.00 |
| ATOM | 69 | N | ASN | 1 | 114 | 17.767 | -21.723 | 43.157 | 1.00 | 0.00 |
| ATOM | 70 | CA | ASN | 1 | 114 | 17.585 | -21.498 | 44.611 | 1.00 | 0.00 |
| ATOM | 71 | C | ASN | 1 | 114 | 16.288 | -22.097 | 45.204 | 1.00 | 0.00 |
| ATOM | 72 | O | ASN | 1 | 114 | 15.110 | -21.738 | 44.968 | 1.00 | 0.00 |
| ATOM | 73 | CB | ASN | 1 | 114 | 17.738 | -20.004 | 44.811 | 1.00 | 0.00 |
| ATOM | 74 | CG | ASN | 1 | 114 | 17.761 | -19.604 | 46.263 | 1.00 | 0.00 |
| ATOM | 75 | OD1 | ASN | 1 | 114 | 17.013 | -18.825 | 46.820 | 1.00 | 0.00 |
| ATOM | 76 | ND2 | ASN | 1 | 114 | 18.754 | -20.204 | 46.933 | 1.00 | 0.00 |
| ATOM | 77 | H | ASN | 1 | 114 | 17.244 | -21.387 | 42.373 | 1.00 | 0.00 |
| ATOM | 78 | 1HD2 | ASN | 1 | 114 | 19.381 | -20.849 | 46.496 | 1.00 | 0.00 |
| ATOM | 79 | 2HD2 | ASN | 1 | 114 | 19.079 | -20.336 | 47.869 | 1.00 | 0.00 |
| ATOM | 80 | N | ASP | 1 | 116 | 16.009 | -21.817 | 48.288 | 1.00 | 0.00 |
| ATOM | 81 | CA | ASP | 1 | 116 | 16.037 | -21.119 | 49.574 | 1.00 | 0.00 |
| ATOM | 82 | C | ASP | 1 | 116 | 15.396 | -19.793 | 49.630 | 1.00 | 0.00 |
| ATOM | 83 | O | ASP | 1 | 116 | 15.774 | -18.837 | 50.337 | 1.00 | 0.00 |
| ATOM | 84 | CB | ASP | 1 | 116 | 17.464 | -20.968 | 50.072 | 1.00 | 0.00 |
| ATOM | 85 | CG | ASP | 1 | 116 | 18.319 | -22.224 | 49.976 | 1.00 | 0.00 |
| ATOM | 86 | OD1 | ASP | 1 | 116 | 18.006 | -23.130 | 50.730 | 1.00 | 0.00 |
| ATOM | 87 | OD2 | ASP | 1 | 116 | 19.236 | -22.263 | 49.180 | 1.00 | 0.00 |
| ATOM | 88 | H | ASP | 1 | 116 | 16.323 | -21.489 | 47.396 | 1.00 | 0.00 |
| ATOM | 89 | N | ASP | 1 | 117 | 14.372 | -19.664 | 48.769 | 1.00 | 0.00 |
| ATOM | 90 | CA | ASP | 1 | 117 | 13.409 | -18.653 | 49.009 | 1.00 | 0.00 |

FIG. 3B

| ATOM | 91 | C | ASP | 1 | 117 | 12.024 | -19.105 | 48.641 | 1.00 | 0.00 |
| ATOM | 92 | O | ASP | 1 | 117 | 11.645 | -19.083 | 47.471 | 1.00 | 0.00 |
| ATOM | 93 | CB | ASP | 1 | 117 | 13.801 | -17.459 | 48.181 | 1.00 | 0.00 |
| ATOM | 94 | CG | ASP | 1 | 117 | 13.342 | -16.211 | 48.889 | 1.00 | 0.00 |
| ATOM | 95 | OD1 | ASP | 1 | 117 | 13.889 | -15.978 | 49.966 | 1.00 | 0.00 |
| ATOM | 96 | OD2 | ASP | 1 | 117 | 12.577 | -15.397 | 48.399 | 1.00 | 0.00 |
| ATOM | 97 | H | ASP | 1 | 117 | 14.092 | -20.522 | 48.339 | 1.00 | 0.00 |

END

```
Human      Met Ala Leu Lys Arg Ile His Lys Glu Leu Asn Asp Leu Ala Arg Asp Pro Pro Ala Gln Cys Ser Ala Gly Pro Val Gly
S Pombe    Met Ala Leu Lys Arg Ile Asn Arg Glu Leu Ala Asp Leu Gly Lys Asp Pro Pro Ser Ser Cys Ser Ala Gly Pro Val Gly
C Albicans Met Ser Leu Lys Arg Ile Asn Lys Glu Leu Ser Asp Leu Gly Arg Asp Pro Pro Ser Ser Cys Ser Ala Gly Pro Val Gly Asp Asp Met Phe His Trp Gln Ala Thr Ile Met Gly Pro Asn Asp Ser Pro Tyr Gln Gly Gly Val Phe Phe Leu Thr Ile
Asp Asp Leu Phe His Trp Gln Ala Thr Ile Met Gly Pro Ala Asp Ser Pro Tyr Ala Gly Gly Val Phe Leu Leu Ser Ile
Asp Asp Leu Tyr His Trp Gln Ala Ser Ile Met Gly Pro Pro Asp Ser Pro Tyr Ala Gly Gly Val Phe Leu Leu Ser Ile His Phe Pro Thr Asp Tyr Pro Phe Lys Pro Pro Lys Val Ala Phe Thr Thr Arg Ile Tyr His Pro Asn Ile Asn Ser Asn
His Phe Pro Thr Asp Tyr Pro Phe Lys Pro Pro Lys Val Asn Phe Thr Thr Arg Ile Tyr His Pro Asn Ile Asn Ser Asn
His Phe Pro Thr Asp Tyr Pro Leu Lys Pro Pro Lys Ile Ala Leu Thr Lys Thr Lys Ile Tyr His Pro Asn Ile Asn Ser Asn Gly Ser Ile Cys Leu Asp Ile Leu Arg Ser Gln Trp Ser Pro Ala Leu Thr Ile Ser Lys Val Leu Leu Ser Ile Cys Ser
Gly Ser Ile Cys Leu Asp Ile Leu Arg Asp Gln Trp Ser Pro Ala Leu Thr Ile Ser Lys Val Leu Leu Ser Ile Cys Ser
Gly Asn Ile Cys Leu Asp Ile Leu Lys Asp Gln Trp Ser Pro Ala Leu Thr Ile Ser Lys Val Leu Leu Ser Ile Cys Ser Leu Leu Cys Asp Pro Asn Pro Asp Asp Pro Leu Val Pro Glu Ile Ala Arg Ile Tyr Gln Thr Asp Arg Glu Lys Tyr Asn
Leu Leu Thr Asp Pro Asn Pro Asp Asp Pro Leu Val Pro Glu Ile Ala His Val Tyr Lys Thr Asp Arg Ser Arg Tyr Glu
Leu Leu Thr Asp Ala Asn Pro Asp Asp Pro Leu Val Pro Glu Ile Ala His Ile Tyr Lys Thr Asp Arg Ala Lys Tyr Glu Arg Ile Ala Arg Glu Trp Thr Gln Lys Tyr Ala Met
Leu Ser Ala Arg Glu Trp Thr Arg Lys Tyr Ala Ile
Ala Thr Ala Lys Glu Trp Thr Lys Lys Tyr Ala Val
```

UBIQUITIN CONJUGATING ENZYMES

RELATED APPLICATIONS

This application is a continuation-in-part of U.S. Ser. No. 08/247,904, entitled "Human Ubiquitin Conjugating Enzyme", which is a continuation-in-part of U.S. Ser. No. 08/176,937 filed Jan. 4, 1994, now abandoned, entitled "Assay and Reagents for Detecting Inhibitors of Ubiquitin-dependent Degradation of Cell Cycle Regulatory Proteins", the specification of which are incorporated by reference herein.

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Ubiquitin is itself a substrate for ubiquitination. Depending on the ubiquitin-conjugating enzyme and the nature of the substrate., specific lysine residues of ubiquitin are used as acceptor sites for further ubiquitinations. This can lead to either a linear multi-ubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for degradation, multi-ubiquitination appears to be required in most cases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells.

For instance, the p53 protein is a key regulator of mammalian cell growth and its gene is frequently mutated in a wide range of human tumors (Hollstein et al. (1991) *Science* 253:49–53). Furthermore, many DNA tumor viruses encode viral antigens that inactivate p53 (e.g., see Vogelstein et al. (1992) *Cell* 70:523–526). The high risk human papillomaviruses, such as HPV-16 and -18, are strongly implicated in the pathogenesis of cervical carcinoma (zur Hansen et al. (1991) *Science* 254:1167–1173). These viruses encode two transforming proteins, E6 and E7, that target the cellular growth regulators p53 and pRb respectively. The mode of inactivation of p53 by E6 is apparently mediated by a ubiquitin-dependent pathway. Viral E6 and a cellular E6-associated protein (E6AP) combine to stimulate the ubiquitination of p53, thus targeting p53 for degradation (Scheffner et al. (1990) *Cell* 63:1129–1136. In this reaction, E6 and E6AP are thought to be providing a ubiquitin ligase, or E3-like activity (Scheffner et al. (1993) *Cell* 75:495–505). However, the ubiquitin-conjugating enzyme (E2) involved in p53 ubiquitination has not previously been characterized.

SUMMARY OF THE INVENTION

The present invention relates to the discovery in eukaryotic cells, particularly human cells and certain yeast cells, of a novel ubiquitin conjugating enzyme (hereinafter "UbCE"). In human cells, the enzyme can function to mediate ubiquitination of cell check regulatory proteins, e.g. p53, and is therefore involved in regulating cell cycle progression, e.g. cell growth.

One aspect of the invention features a substantially pure preparation of an a human UbCE polypeptide ("hUbCE"), or a fragment thereof, which can function as a ubiquitin conjugating enzyme. In a preferred embodiment: the polypeptide has an amino acid sequence at least 90% homologous to the amino acid sequence of SEQ ID No. 2; the polypeptide has an amino acid sequence at least 95% homologous to the amino acid sequence of SEQ ID No. 2; the polypeptide has an amino acid sequence at least 97% homologous to the amino acid sequence of SEQ ID No. 2; the polypeptide has an amino acid sequence identical to the amino acid sequence of SEQ ID No. 2. In a preferred embodiment: the fragment comprises at least 5 contiguous amino acid residues of SEQ ID No. 2; the fragment comprises at least 20 contiguous amino acid residues of SEQ ID No. 2; the fragment comprises at least 50 contiguous amino acid residues of SEQ ID No. 2. In a preferred embodiment, the fragment comprises at least a portion of amino acid residues Cys-107 through Met-147, e.g. 5 amino acid residues, e.g. 15 amino acid residues, e.g. 25 amino acid residues.

Another aspect of the invention features a substantially pure preparation of a Candida UbCE polypeptide ("caUbCE"), or a fragment thereof, which can function as a ubiquitin conjugating enzyme. In a preferred embodiment: the polypeptide has an amino acid sequence at least 90% homologous to the amino acid sequence of SEQ ID No. 4; the polypeptide has an amino acid sequence at least 95% homologous to the amino acid sequence of SEQ ID No. 4; the polypeptide has an amino acid sequence at least 97% homologous to the amino acid sequence of SEQ ID No. 4; the polypeptide has an amino acid sequence identical to the amino acid sequence of SEQ ID No. 4. In a preferred embodiment: the fragment comprises at least 5 contiguous amino acid residues of SEQ ID No. 4; the fragment comprises at least 20 contiguous amino acid residues of SEQ ID No. 4; the fragment comprises at least 50 contiguous amino acid residues of SEQ ID No. 4. In a preferred embodiment, the fragment comprises at least a portion of amino acid residues Cys-107 through Val-147, e.g. 5 amino acid residues, e.g. 15 amino acid residues, e.g. 25 amino acid residues.

Another aspect of the invention features a substantially pure preparation of a Schizosaccharomyces UbCE polypeptide ("spUbCE"), or a fragment thereof, which can function as a ubiquitin conjugating enzyme. In a preferred embodiment: the polypeptide has an amino acid sequence at least 90% homologous to the amino acid sequence of SEQ ID No. 6; the polypeptide has an amino acid sequence at least 95% homologous to the amino acid sequence of SEQ ID No. 6; the polypeptide has an amino acid sequence at least 97% homologous to the amino acid sequence of SEQ ID No. 6; the polypeptide has an amino acid sequence identical to the amino acid sequence of SEQ ID No. 6. In a preferred embodiment: the fragment comprises at least 5 contiguous amino acid residues of SEQ ID No. 6; the fragment comprises at least 20 contiguous amino acid residues of SEQ ID No. 6; the fragment comprises at least 50 contiguous amino acid residues of SEQ ID No. 6. In a preferred embodiment, the fragment comprises at least a portion of amino acid residues Cys- 107 through Ile-147, e.g. 5 amino acid residues, e.g. 15 amino acid residues, e.g. 25 amino acid residues.

Another aspect of the present invention features an hUbCE polypeptide which functions in one of either role of an agonist of cell-cycle regulation or an antagonist of cell-cycle regulation. In a preferred embodiment the hUbCE polypeptide has: an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells. The biological activity can further include the ability to bind and conjugate ubiquitin, as well as bind and transfer ubiquitin to E6AP.

Yet another aspect of the present invention concerns an immunogen comprising an UbCE polypeptide, or a fragment thereof in an immunogenic preparation, the immunogen being capable of eliciting an immune response specific for the UbCE polypeptide; e.g. a humoral response, eg. an antibody response., e.g. a cellular response.

A still further aspect of the present invention features an antibody preparation specifically reactive with an epitope of the UbCE immunogen, e.g. reactive with hUbCE, e.g. reactive with caUbC, e.g. reactive with spUbCE.

Another aspect of the present invention features recombinant hUbCE polypeptide, or a fragment thereof, having an amino acid sequence preferably: at least 90% homologous to SEQ ID No. 2; at least 95% homologous to SEQ ID No: 2; at least 97% homologous to SEQ ID No. 2. In a preferred embodiment, the recombinant hUbCE protein functions in one of either role of an agonist of cell cycle regulation or an antagonist of cell cycle regulation. In a more preferred embodiment: the hUbCE polypeptide mediates ubiquitination of cellular proteins, e.g. cell-cycle regulatory proteins, e.g. p53; the hUbCE polypeptide mediates ubiquitin-dependent degradation of cellular proteins, e.g. cell-cycle regulatory proteins, e.g. p53; the hUbCE polypeptide affects the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31 or HPV-33 infected cells, e.g. in cells expressing a papillomavirus E6 protein, e.g. in transformed cells, e.g. in cancerous cells.

Another aspect of the present invention features recombinant caUbCE polypeptide, or a fragment thereof, having an amino acid sequence preferably: at least 90% homologous to SEQ ID No. 4; at least 95% homologous to SEQ ID No. 4; at least 97% homologous to SEQ ID No. 4. In a preferred embodiment, the recombinant caUbCE protein functions in one of either role of an agonist of cell cycle regulation or an antagonist of cell cycle regulation. In a more preferred embodiment the caUbCE polypeptide mediates ubiquitination of cellular proteins of candida cells.

Another aspect of the present invention features recombinant spUbCE polypeptide, or a fragment thereof, having an amino acid sequence preferably: at least 90% homologous to SEQ ID No. 6; at least 95% homologous to SEQ ID No. 6; at least 97% homologous to SEQ ID No. 6. In a preferred embodiment, the recombinant spUbCE protein functions in one of either role of an agonist of cell cycle regulation or an antagonist of cell cycle regulation. In a more preferred embodiment the spUbCE polypeptide mediates ubiquitination of cellular proteins of Schizosaccharomyces cells.

In yet other preferred embodiments, the recombinant UbCE protein is a fusion protein further comprising a second polypeptide portion having an amino acid sequence from a protein unrelated the protein of SEQ ID No. 2, 4 or 6. Such fusion proteins can be functional in a two-hybrid assay.

Another aspect of the present invention provides a substantially pure nucleic acid having a nucleotide sequence which encodes an hUbCE polypeptide, or a fragment thereof, having an amino acid sequence at least 90% homologous to SEQ ID NO. 2. In a more preferred embodiment, the nucleic acid encodes a protein having an amino acid sequence at least 95% homologous to SEQ ID No. 2; and more preferably at least 97% homologous to SEQ ID No. 2. The nucleic preferably encodes: a hUbCE polypeptide which mediates ubiquitination of cellular proteins, e.g. cell-cycle regulatory proteins, e.g. p53; a hUbCE polypeptide which mediates ubiquitin-dependent degradation of cellular proteins, e.g. cell-cycle regulatory proteins, e.g. p53; a hUbCE polypeptide which affects the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells.

Another aspect of the present invention provides a substantially pure nucleic acid having a nucleotide sequence which encodes a caUbCE polypeptide, or a fragment thereof, having an amino acid sequence at least 90% homologous to SEQ ID NO. 4. In a more preferred embodiment, the nucleic acid encodes a protein having an amino acid sequence at least 95% homologous to SEQ ID No. 4; and more preferably at least 97% homologous to SEQ ID No. 4.

Another aspect of the present invention provides a substantially pure nucleic acid having a nucleotide sequence which encodes an spUbCE polypeptide, or a fragment thereof, having an amino acid sequence at least 90% homologous to SEQ ID NO. 4. In a more preferred embodiment, the nucleic acid encodes a protein having an amino acid sequence at least 95% homologous to SEQ ID No. 4; and more preferably at least 97% homologous to SEQ ID No. 4.

In yet a further preferred embodiment, the nucleic acid which encodes a UbCE polypeptide of the present invention, or a fragment thereof, hybridizes under stringent conditions to a nucleic acid probe corresponding to at least 12 consecutive nucleotides of one of SEQ ID Nos. 1, 3 or 5; more preferably to at least 20 consecutive nucleotides of said sequences; more preferably to at least 40 consecutive nucleotides. In yet a further preferred embodiment, the UbCE encoding nucleic acid hybridizes to a nucleic acid probe corresponding to a subsequence encoding at least 4 consecutive amino acids between residues 107 and 147 of SEQ ID No. 2, 4 or 6, more preferably at least 10 consecutive amino acid residues, and even more preferably at least 20 amino acid residues. In yet a preferred embodiment the nucleic acid encodes an hUbCE polypeptide which includes Cys-107 through Cys-111.

Furthermore, in certain preferred embodiments, UbCE encoding nucleic acid will comprise a transcriptional regulatory sequence, e.g. at least one of a transcriptional promoter or transcriptional enhancer sequence, operably linked to the UbCE gene sequence so as to render the UbCE gene sequence suitable for use as an expression vector. In one embodiment, the UbCE gene is provided as a sense construct. In another embodiment, the UbCE gene is provided as an anti-sense construct.

The present invention also features transgenic non-human animals, e.g. mice, which either express a heterologous hUbCE gene, e.g. derived from humans, or which mis-express their own homolog of the subject human gene, e.g. expression of the mouse hUbCE homolog is disrupted. Such a transgenic animal can serve as an animal model for studying cellular disorders comprising mutated or mis-expressed hUbCE alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No. 1 or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a hUbCE nucleic acid in a sample of cells isolated from a patient; e.g. measuring the hUbCE mRNA level in a cell; e.g. determining whether the genomic hUbCE gene has been mutated or deleted.

The present invention also provides a method for treating an animal having unwanted cell growth characterized by a loss of wild-type p53 function, comprising administering a therapeutically effective amount of an agent able to inhibit a ubiquitin conjugating activity of the subject hUbCE protein.

The present invention also provides a method for treating an animal having an unwanted mycotic infection, comprising administering a therapeutically effective amount of an agent able to inhibit a ubiquitin conjugating activity of a fungal ubiquitin-conjugating enzyme, such as the subject caUbCE protein or spUBC protein, without substantially inhibiting the hUbCE protein.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by SEQ ID No. 2, or a homolog thereof; or (ii) the mis-expression of the hUbCE gene. In preferred embodiments: detecting the genetic lesion comprises ascertaining the existence of at least one of a deletion of one or more nucleotides from the gene, an addition of one or more nucleotides to the gene, an substitution of one or more nucleotides of the gene, a gross chromosomal rearrangement of the gene, a gross alteration in the level of a messenger RNA transcript of the gene, the presence of a non-wild type splicing pattern of a messenger RNA transcript of the gene, or a non-wild type level of the protein. For example, detecting the genetic lesion can comprise (i) providing a probe/primer comprising an oligonucleotide containing a region of nucleotide sequence which hybridizes to a sense or antisense sequence of SEQ ID No. 1 or naturally occurring mutants thereof or 5' or 3' flanking sequences naturally associated with the gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the hUbCE gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of the protein is detected in an immunoassay.

Yet a further aspect of the present invention concerns three-dimensional molecular models of the subject UbCE proteins, and their use as templates for the design of agents able to inhibit at least one biological activity of the ubiquitin conjugating enzyme. In preferred embodiments, the molecular models can be used to design pharmacophores by rational drug design; e.g. agents which can inhibit binding of the subject hUbCE protein with any one of ubiquitin, an E1 enzyme, an E3 protein(s) such as E6 or E6AP, or the downstream target of the enzyme, such as p53.

For instance, one aspect of the present invention concerns a method for identifying inhibitors of the subject ubiquitin-conjugating enzyme by molecular modeling. In general, the method comprise providing a molecular model of the enzyme, such as the active site, as well as a molecular model of a candidate drug. The drug model is docked with the UbCE model and binding criteria, e.g. electrostatic interactions, hydrogen bonding, hydrophobic interactions, desolvation effects, cooperative motions of ligand and enzyme, of the docked models is determined. Based on the binding criteria of a particular candidate drug, the likelihood of the candidate drug being an inhibitor of said UbCE can be determined. Thus, the subject method can be used to design candidate agents, which when obtained, e.g. by chemical synthesis or from commercial sources, can be provided in an assay with the human ubiquitin-conjugating enzyme of the present invention in order to determine the actual inhibitory activity of the candidate drug. In preferred embodiments, the hUbCE model includes the amino acid residues Cys-85, Leu-86, Asp-87, Ile-88, Arg-90, Ser-91, Leu-109, Asn-114, Asp-116, and Asp-117, the atomic coordinates of these residues, at 300° K, having an overall RMS within 2 Å of the atomic coordinates shown in FIG. 2, more preferably an overall RMS within 1 Å, and most preferably an overall RMS within 0.5 Å. Moreover, the hUbCE model can include amino acid residues Arg-5 through Met-147 of SEQ ID No. 2. In preferred embodiments, the atomic coordinates for the C-α carbon for each of these residues, at 300° K, have an overall RMS within 2 Å of the C-α atomic coordinates shown in FIG. 1, more preferably an overall RMS within 1 Å, and most preferably an overall RMS within 0.5 Å. Moreover, the hUbCE model can include the atomic coordinates for each atom of the amino acid residues Arg-5 through Met-147 of SEQ ID No. 2. In preferred embodiments, the atomic coordinates for each of these residues, at 300° K, have an overall RMS within 2 Å of the C-α atomic coordinates shown in FIG. 1, more preferably an overall RMS within 1 Å, and most preferably an overall RMS within 0.5 Å.

Yet a further aspect of this invention concerns addressable electronic memory means, e.g. RAM or ROM memory, magnetic disk devices, optical storage devices, having stored therein an addressable electronic representation of atomic coordinates of a molecular model of a human ubiquitin-conjugating enzyme. In preferred embodiments, the hUbCE model comprises the amino acid residues Cys-85, Leu-86, Asp-87, Ile-88, Arg-90, Ser-91, Leu-109, Asn-114, Asp-116, and , Asp-117, the atomic coordinates of these residues, at 300° K, having an overall RMS within 2 Å of the atomic coordinates shown in FIG. 2. In another embodiments, the human ubiquitin-conjugating enzyme model comprises amino acid residues Arg-5 through Met-147 of SEQ ID No. 2, the atomic coordinates of the residues, at 300° K, having an overall RMS within 2 Å of the atomic coordinates shown in FIG. 1.

Other features and advantages of the invention will be apparent from the following detailed description, and from the claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature See, for example, *Molecular Cloning A Laboratory Manual*, 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987., Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

BRIEF DESCRIPTION OF THE FIGURES

FIG. 1 is the atomic coordinates for Arg-5 through Met-147 of SEQ ID No. 2 in standard Brookhaven protein databank (pdb) format.

FIG. 3 is the atomic coordinates for Cys-85, Leu-86, Asp-87, Ile-88, Arg-90, Ser-91, Leu-109, Asn-114, Asp-116, and Asp-117 of SEQ ID No. 2 in standard Brookhaven protein databank (pdb) format.

FIG. 5 is a sequence alignment of hUbCE ("human"), spUbCE ("S pombe") and caUbCE ("*C albicans*").

DETAILED DESCRIPTION OF THE INVENTION

Figure 2:
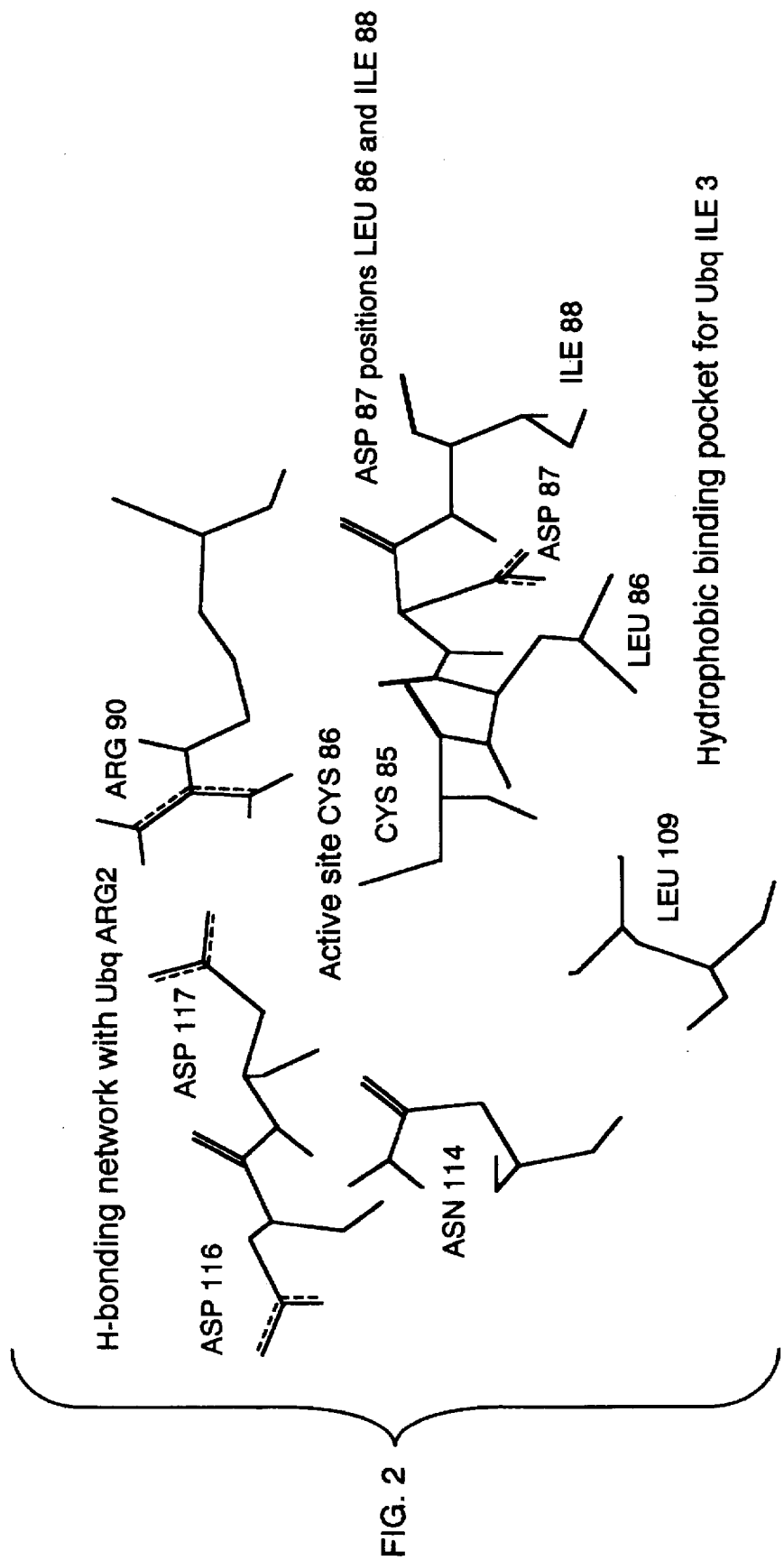
FIG. 2 is a stick figure illustrating the residues of the active site of hUbCE.

The ubiquitin system is essential for a wide spectrum of cellular phenomena, and is a component of many biological regulatory mechanisms, including aspects of growth control, metabolic regulation, embryonic development, and cell-cycle progression.

The present invention relates to the discovery of a family of related ubquitin-conjugating enzymes ("UbCE"). In particular, members of this family have been cloned from various eukaryotic sources, and include, for example, a human ubiquitin-conjugating enzyme ("hUbCE"), *C. albi-*

*cans* ubiquitin-conjugating enzyme ("caUbCE"), and an *S. pombe* ubiquitin-conjugating enzyme ("spUbCE"). The nucleotide sequences for the human UbCE, the *C. albicans* UbCE, and the *S. pombe* UbCE coding sequences are provided in SEQ ID Nos. 1, 3 and 5, respectively. The corresponding amino acid sequences are represented in SEQ ID Nos. 2, 4 and 6.

The biological activity of the UbCE proteins of the present invention is likely to be important in a number of basic cellular functions, such as regulation of gene expression, regulation of the cell-cycle, modification of cell surface receptors, biogenesis of ribosomes, and DNA repair. An apparent function of members of this family of enzymes in ubiquitin-mediated systems is to control the cellular half-lives of vasrious proteins. For instance, as demonstrated in the Examples, hUbCE is implicated in the ubiquitin-mediated inactivation of cell-cycle regulatory proteins, particularly p53. As is generally known, p53 is a checkpoint protein that plays an important role in sensing DNA damage or regulating cellular response to stress. Moreover, lesions in the p53 gene have been shown to be associated with a wide variety of proliferative diseases. Consequently, the present invention identifies a potential molecular target, e.g., hUbCE, for regulating the cellular half-life of p53 and thereby modulating, for instance, cell proliferation, apoptosis and cellular sensitivity to chemotherapeutics and DNA damaging agents.

Accordingly, the present invention makes available diagnostic and therapeutic assays, reagents and kits for detecting and treating proliferative disorders arising from, for example, tumorogenic transformation of cells, or other hyperplastic or neoplastic transformation processes. For example, the present invention makes available reagents, such as antibodies and nucleic acid probes, for detecting altered complex formation, and/or altered levels of hUbCE expression, and/or hUbCE-gene deletion or mutation, in order to identify transformed cells. Moreover, the present invention provides a method of treating a wide variety of pathological cell proliferative conditions, such as by gene therapy utilizing recombinant gene constructs encoding the subject hUbCE proteins, by providing peptidomimetics which either inhibit or potentiate the interaction between hUbCE and E6AP or an E6AP-containing complexes, or by providing inhibitors of the catalytic activity of hUbCE. Such methods can also be used in tissue culture, such as to regulate the transformation of cells in vitro.

In similar fashion, the present invention also makes available diagnostic and therapeutic assays for detecting and treating yeast/fungal infections, where such infections occur in an animal, e.g. humans, or on a non-living object, such as food or medical instruments. For example, given the apparent role of the subject UbCEs, namely caUbCE and spUbCE, in regulation of proteins involved in growth, mating and proliferation of yeast, inhibitors of the subject ubiquitin conjugating enzyme can be used to treat mycotic infections, as disinfectants, or as food preservatives.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding a UbCE polypeptide of the present invention, including both exon and (optionally) intron sequences. In preferred embodiments, the nucleic acid is DNA or RNA. Exemplary recombinant genes include nucleic acids which encode all or a catalytically active portion of the hUbCE protein represented in SEQ ID No. 2, the caUbCE protein represented in SEQ ID No. 4, or the spUbCE protein represented in SEQ ID No. 6. The term "intron" refers to a DNA sequence present in a given UbCE-gene which is not translated into protein and is generally found between exons.

The term "transfection" refers to the introduction of a nucleic acid, e.g., an expression vector, into a recipient cell by nucleic acid-mediated gene transfer. "Transformation", as used herein, refers to a process in which a cell's genotype is chanced as a result of the cellular uptake of exogenous nucleic acid, and, for example, the transformed cell expresses a recombinant form of one of the subject UbCE proteins.

"Cells" or "cell cultures" or "recombinant host cells" or "host cells" are often used interchangeably as will be clear from the context. These terms include the immediate subject cell which expresses a ubiquitin-conjugating enzyme of the present invention, and, of course, the progeny thereof. It is. understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant UbCE-protein.

As used herein, the term "vector" refers to a nucleic acid molecule capable of transporting another nucleic acid to which it has been linked. The term "expression vector" includes plasmids, cosmids or phages capable of synthesizing the subject proteins encoded by their respective recombinant genes carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant UbCE-gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "tissue-specific promoters" means a DNA sequence that serves as a promoter, i.e., regulates expression of a selected DNA sequence operably linked to the promoter, and which effects expression of the selected DNA sequence in specific cells of a tissue, such as cells of an epithelial lineage, e.g. cervical squamous cells. In an illustrative embodiment of epithelial-specific promoters, gene constructs can be used as a part of gene therapy to deliver, for example, genes encoding a dominant negative hUbCE mutant, in order to inhibit degradation of p53 required for the pathogenesis of certain papillomavirus-mediated disorders, e.g. papillomas, or to direct expression of an antisense construct of the subject ubiquitin-conjugating enzyme in only epithelial tissue. The term also covers so-called "leaky" promoters, which regulate expression of a selected DNA primarily in one tissue, but cause expression in other tissues as well.

As used herein, a "transgenic animal" is any animal, preferably a non-human mammal in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject UbCE protein, e.g. either agonistic or antagonistic forms, or in which the endogenous UbCE gene has been disrupted. However, transgenic animals in which the recombinant UbCE gene is silent are also contemplated, as for example, the FLP or CRE recombinase dependent constructs described below. The "non-human animals" of the invention include vertebrates such as rodents, non-human primates, sheep, dog, cow, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the recombinant UbCE gene is present and/or expressed in some tissues but not others.

As used herein, the term "transgene" means a nucleic acid sequence (encoding, e.g., a UbCE polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

"Homology" refers to sequence similarity between two peptides or between two nucleic acid molecules Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "evolutionarily related to", with respect to nucleic acid sequences encoding the subject ubiquitin-conjugating enzymes, refers to nucleic acid sequences which have arisen naturally in an organism, including naturally occurring mutants. The term also refers to nucleic acid sequences which, while derived from a naturally occurring enzymes, have been altered by mutagenesis, as for example, combinatorial mutagenesis described below, yet still encode polypeptides which have at least one activity of a UbCE protein.

As described below, one aspect of this invention pertains to an isolated nucleic acid comprising a nucleotide sequence encoding one of the subject UbCE proteins, fragments thereof encoding polypeptides having at least one biological activity of the UbCE protein, and/or equivalents of such nucleic acids. The term "nucleic acid" as used herein is intended to include such fragments and equivalents. The term "equivalent" is understood to include nucleotide sequences encoding functionally equivalent UbCE proteins or functionally equivalent peptides having an activity of a ubiquitin-conjugating enzyme such as described herein. Equivalent nucleotide sequences will include sequences that differ by one or more nucleotide substitutions, additions or deletions, such as allelic variants; and will also include sequences that differ from the nucleotide sequence encoding the hUbCE protein shown in SEQ ID No: 1, the caUbCE protein shown in SEQ ID No: 3, or the spUbCE protein shown in SEQ ID No: 5, due to the degeneracy of the genetic code. Equivalents will also include nucleotide sequences which hybridize under stringent conditions (i.e., equivalent to about 20°–27° C. below the melting temperature ($T_m$) of the DNA duplex formed in about 1M salt) to the nucleotide sequence represented in at least one of SEQ ID Nos: 1, 3 or 5. In one embodiment, equivalents will further include nucleic acid sequences derived from and evolutionarily related to the nucleotide sequences shown in any of SEQ ID Nos: 1, 3 or 5.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding on of the subject UbCE-proteins preferably includes no more than 10 kilobases (kb) of nucleic acid sequence which naturally immediately flanks the UbCE gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Polypeptides referred to herein as possessing the acitivity of a ubiquitin-conjugating enzyme (UbCE), e.g. are UbCE agonists are understood to have an amino acid sequence identical to or homologous with the amino acid sequences shown in any on of SEQ ID Nos: 2, 4 or 6, and which are capable of forming a thiol ester adduct with the C-terminal carboxyl group of ubiquitin and transferring the ubiquitin to an ε-amino group in an acceptor protein by formation of an isopeptide bond. The biological activity of the subject UbCE proteins can include participation in degradative pathways for selective proteolysis of constitutively or conditionally short-lived proteins as well as abnormal proteins. Antagonistic forms of the subject UbCE proteins are defined as proteins that are homologous, but not identical, to the UbCE proteins represented in SEQ ID Nos: 2, 4 or 6, or that are fragments of the wild-type proteins, which inhibit the transfer of ubiquitin by the naturally occurring form of the ubiquitin-conjugating enzyme. For instance, as described below, mutations in the active site of the enzyme, e.g. Cys-85, can produce dominant negative forms of the subject UbCEs which antagonize the action of the wild-type form of the protein.

Polypeptides referred to in particular as having an activity of an hUbCE protein are defined as peptides that have an amino acid sequence corresponding to all or a portion of the amino acid sequence of the human ubiquitin conjugating enzyme shown in SEQ ID No:2 and which have at least one biological activity of an hUbCE protein- such as an ability to mediate ubiquitination of cellular proteins, e.g. cell-cycle regulatory proteins, e.g., p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells. Other biological activities of the subject hUbCE proteins are described herein or will be reasonably apparent to those skilled in the art.

Moreover, it will be generally appreciated that, under certain circumstances, it will be advantageous to provide homologs of naturally-occurring forms of the subject UbCE proteins which are either agonists or antagonists of only a subset of that protein's biological activities. Thus, specific biological effects can be elicited by treatment with a homolog of limited function, and with fewer side effects relative to treatment with agonists or antagonists which are directed to all of the biological activities of that protein. For example, hUbCE homologs can be generated which bind to and inhibit activation of other proteins in the ubiquitin pathway of p53 without substantially interfering with the ubiquitination of other cellular proteins.

In one embodiment, the nucleic acid of the invention encodes a polypeptide which is either an agonist or antagonist the human UbCE protein and comprises an amino acid sequence represented by SEQ ID No: 2. Preferred nucleic acids encode a peptide having an hUbCE protein activity, or which is an antagonist thereof, and being at least 90% homologous, more preferably 95% homologous and most preferably 97% homologous with an amino acid sequence shown in SEQ ID No: 2. Nucleic acids which encode agonist or antagonist forms of an hUbCE protein and having at least about 98–99% homology with a sequence shown in SEQ ID No: 2 are also within the scope of the invention. Preferably, the nucleic acid is a cDNA molecule comprising at least a portion of the nucleotide sequence encoding an hUbCE protein shown in SEQ ID No. 1. A preferred portion of the cDNA molecule shown in SEQ ID No. 1 includes the coding region of the molecule.

In another embodiment, the nucleic acid of the invention encodes a polypeptide which is either an agonist or antagonist a Candida UbCE protein, e.g. a *C. albicans* UbCE, and comprises an amino acid sequence represented by SEQ ID No: 4. Preferred nucleic acids encode a peptide having an caUbCE protein activity, or which is an antagonist thereof, and being at least 90% homologous, more preferably 95% homologous and most preferably 97% homologous with an amino acid sequence shown in SEQ ID No: 4. Nucleic acids which encode agonist or antagonist forms of an caUbCE protein and having at least about 98–99% homology with a sequence shown in SEQ ID No: 4 are also within the scope of the invention. Preferably, the nucleic acid is a cDNA molecule comprising at least a portion of the nucleotide sequence encoding an caUbCE protein shown in SEQ ID No. 3. A preferred portion of the cDNA molecule shown in SEQ ID No. 3 includes the coding region of the molecule. The present invention contemplates closely related homologs (orthologs) from other species of Candida, e.g. *Candida stellatoidea, Candida tropicalis, Candida parapsilosis, Candida krusei, Candida pseudotropicalis, Candida quillermondii,* or *Candida rugosa.*

In yet another embodiment, the nucleic acid of the invention encodes a polypeptide which is either an agonist or antagonist a Schizosaccharomyces UbCE protein, e.g. an *S. pombe* UbCE, and comprises an amino acid sequence represented by SEQ ID No: 6. Preferred nucleic acids encode a peptide having an spUbCE protein activity, or which is an antagonist thereof, and being at least 90% homologous, more preferably 95% homologous and most preferably 97% homologous with an amino acid sequence shown in SEQ ID No: 6. Nucleic acids which encode agonist or antagonist forms of an spUbCE protein and having at least about 98–99% homology with a sequence shown in SEQ ID No: 6 are also within the scope of the invention. Preferably, the nucleic acid its a cDNA molecule comprising at least a portion of the nucleotide sequence encoding an spUbCE protein shown in SEQ ID No. 5. A preferred portion of the cDNA molecule shown in SEQ ID No. 5 includes the coding region of the molecule.

Another aspect of the invention provides a nucleic acid which hybridizes under high or low stringency conditions to a nucleic acid which encodes a peptide having all or a portion of an amino acid sequence shown in one of SEQ ID Nos: 2, 4 or 6. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids which differ in sequence from the nucleotide sequences represented in SEQ ID Nos: 1, 3 or 5 due to degeneracy in the genetic code are also within the scope of the invention. Such nucleic acids can encode functionally equivalent peptides (i.e., a peptide having a biological activity of a UbCE protein) but differ in sequence from the sequence shown in SEQ ID No: 1, 3 or 5 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the subject UbCE protein. However, it is expected that DNA sequence polymorphisms that do lead to changes in the amino acid sequences of the present hUbCE protein will exist from one human subject to the next. One skilled in the art will appreciate that these variations in one or more nucleotides (up to about 3–4% of the nucleotides) of the nucleic acids encoding peptides having an activity of, for example, an hUbCE protein may exist among individuals due to natural allelic variation. Any and all such nucleotide variations and resulting amino acid polymorphisms are within the scope of this invention.

Fragments of the nucleic acid encoding an active portion of one of the subject ubiquitin-conjugating enzymes are also within the scope of the invention. As used herein, a fragment of the nucleic acid encoding an active portion of a UbCE protein refers to a nucleotide sequence having fewer nucleotides than the nucleotide sequence encoding the entire amino acid sequence of the protein but which encodes a peptide which possess agonistic or antagonistic activity relative to a naturally occurring form of the enzyme.

Nucleic acid fragments within the scope of the invention also include those capable of hybridizing under high or low stringency conditions with nucleic acids from other species for use in screening protocols to detect UbCE homologs.

Nucleic acids within the scope of the invention may also contain linker sequences, modified restriction endonuclease sites and other sequences useful for molecular cloning, expression or purification of recombinant peptides having at least one biological activity of the subject UbCE ubiquitin-conjugating enzymes. In a preferred embodiment, the nucleic acid fragment comprises at least a portion of the nucleic acid sequence represented by nucleotide residues 319 through 441 of SEQ ID No. 1, corresponding to amino acid residues Cys-107 through Met-147. In preferred embodiments, the nucleic acid encodes an hUbCE polypeptide which includes Cys-107 through Cys-111, and more preferably includes Cys-107 through Asp-117. As illustrated by FIG. 2, certain of the residues from Cys-107 to Asp-111 are important members of the ubiquitin-binding site of hUbCE. Correspondingly, nucleic acid encoding caUbCE or spUbCE preferably include Cys-107 through Val-147 and Cys-107 through Ile-107, respectively.

As indicated by the examples set out below, a nucleic acid encoding a peptide having an activity of the subject ubiquitin-conjugating enzymes may be obtained from mRNA or genomic DNA present in any of a number of eukaryotic cells in accordance with protocols described herein, as well as those generally known to those skilled in the art. A cDNA encoding a homolog of the human UbCE protein, for example, can be obtained by isolating total mRNA from a cell, e.g. a mammalian cell. Double stranded cDNAs can then be prepared from the total mRNA, and subsequently inserted into a suitable plasmid or bacteriophage vector using any one ol a number of known techniques. A gene encoding a UbCE protein can also be cloned using established polymerase chain reaction techniques in accordance with the nucleotide sequence information provided by the invention.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a UbCE protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a UbCE-protein, e.g. the human UbCE gene represented in SEQ ID No. 1. Alternatively, the antisense construct can be an oligonucleotide probe which is generated ex vivo and which, when introduced into the cell causes inhibition of expression by hybridizing with the mRNA and/or genomic sequences encoding one of the subject UbCE proteins. Such oligonucleotide probes are preferably modified oligonucleotide which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

This invention also provides expression vectors containing a nucleic acid encoding the subject UbCE proteins, operably linked to at least one transcriptional regulatory sequence. Operably linked is intended to mean that the nucleic acid is linked to a transcriptional regulatory sequence in a manner which allows expression of the enzyme encoded by the nucleic acid, and that expression is, for example, either constitutively or inducibly controlled by the transcriptional regulatory sequence. Regulatory sequences are art-recognized. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the UbCE proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast alpha -mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered In one embodiment, the expression vector includes a DNA encoding the subject hUbCE protein, e.g. a recombinant hUbCE protein, e.g. a recombinant protein having an agonistic activity relative to a naturally-occurring form of hUbCE, e.g. a recombinant protein having an antagonistic activity relative to a naturally-occurring form of hUbCE. Similar expression vectors for producing recombinant forms of the caUbCE and spUbCE proteins are also contemplated. Such expression vectors can be used to transfect cells to thereby produce proteins or peptides, including fusion proteins or peptides encoded by nucleic acids as described herein.

Moreover, hUbCE-expression vectors can be used as a part of a gene therapy protocol to reconstitute hUbCE function in a cell in which hUbCE is misexpressed, or alternatively, to provide an antagonist of the naturally-occurring hUbCE or an antisense construct -such as to inhibit the hUbCE-mediated degradation of p53. For instance, expression constructs of the subject hUbCE-proteins may be administered in any biologically effective carrier, e.g. any formulation or composition capable of effectively transfecting cells in vivo with a recombinant hUbCE-gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject hUbCE-proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has also been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include:

coupling antibodies specific for cell surface antigens to the viral env protein (Roux et al. (1989) *PNAS* 86:9079–9083; Julan et al (1992) *J. Gen Virol* 73.3251–3255; and Goud et al. (1983) *Virology* 163:251–254); or coupling cell surface ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the hUbCE-gene of the retroviral vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) *BioTechniques* 6:616; Rosenfeld et al. (1991) *Science* 252:431–434; and Rosenfeld et al. (1992) *Cell* 68:143–155). Suitable adenoviral vectors derived from the adenovirus strain Ad type 5 dl324 or other strains of adenovirus (e.g. Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore flavored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol.7. pp. 109–127). Expression of the inserted hUbCE-gene can be under control of, for example, the EIA promoter, the major late promoter (MLP) and associated leader sequences, the E3 promoter, or exogenously added promoter sequences.

Yet another viral vector system useful for delivery of the subject hUbCE-gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant hUbCE-gene in cells of the central nervous system and occular tissue (Pepose et al. (1994) *Invest Ophthalmol Vis Sci* 35:2662–2666).

In addition to viral transfer methods, such as those illustrated above, non-viral methods can also be employed to cause expression of an hUbCE-protein, or an hUbCE antisense molecule, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject hUbCE-gene by the targeted cell. Exemplary gene delivery systems of this type include liposomal derived systems, poly-lysine conjugates, and artificial viral envelopes.

In a representative embodiment, a gene encoding one of the subject hUbCE-proteins can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of papilloma-virus infected epithelial cells can be carried out using liposomes tagged with monoclonal antibodies against, for example, squamous cells.

In similar fashion, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject hUbCE-gene construct can be used to transfect HPV-infected squamous cells in vivo using a soluble polynucleotide carrier comprising an HPV viral caot protein conjugated to a polycation, e.g. poly-lysine (see U.S. Pat. No. 5,166,320). It will also be appreciated that effective delivery of the subject nucleic acid constructs via-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260–926; Wagner et al (1992) *PNAS* 89:7934; and Christiano et al. (1993) *PNAS* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91. 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. The generation of such implants is generally known in the art. See, for example, *Concise Encyclopedia of Medical & Dental Materials*, ed. by David Williams (MIT Press: Cambridge, Mass., 1990); Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; Sefton U.S. Pat. No. 4,353,888; and Aebischer et al. (1991) *Biomaterials* 12:50–55).

This invention also pertains to a host cell transfected or transformed to express a recombinant forms of the subject UbCE proteins The host cell may be any prokaryotic or eukaryotic cell. For example, an hUbCE protein of the present invention may be expressed in bacterial cells such as *E. Coli*, insect cells (baculovirus), yeast, or mammalian cells. Other suitable host cells are known to those skilled in the art The term "recombinant protein" refers to a protein of the present invention which is produced by recombinant DNA techniques, wherein generally DNA encoding the UbCE protein is inserted into a suitable expression vector which is in turn used to transform a host cell to produce the heterologous protein. Moreover, the phrase "derived from", with respect to a recombinant gene encoding the recombinant UbCE, is meant to include within the meaning of "recombinant protein" those proteins having an amino acid sequence of a native UbCE, e.g. hUbCE, caUbCE or spUbCE, or an amino acid sequence similar thereto which is generated by mutations including substitutions and deletions of a naturally occurring form of the protein. Recombinant proteins preferred by the present invention, in addition to native proteins, are at least 90% homologous, more preferably 95% homologous and most preferably 97% homologous with an amino acid sequence shown in one of SEQ ID Nos: 2, 4 or 6. Polypeptides having an activity of an hUbCE protein, or which are antagositic thereto, and which are at least about 90%, more preferably at least about 95%, and most preferably at least about 98–99% homologous with a sequence shown in SEQ ID No: 2, 4 or 6 are also within the scope of the invention.

The present invention further pertains to recombinant UbCE homologs which are encoded by genes derived from other non-human mammals, e.g. mouse, rat, rabbit, or pig, and which have amino acid sequences evolutionarily related to an hUbCE protein. As described above, such recombinant hUbCE proteins preferably are capable of functioning in one of either role of an agonist or antagonist of at least one biological activity of an hUbCE. The term "evolutionarily related to", as set out above, refers to ubiquitin-conjugating enzymes having amino acid sequences which have arisen naturally, or which are mutationally derived, for example, by combinatorial mutagenesis or scanning mutagenesis, but which proteins are homologous to the human UbCE protein represented in SEQ ID No: 2.

The present invention further pertains to methods of producing the subject proteins. For example, a host cell transfected with an expression vector encoding one of the subject UbCE proteins can be cultured under appropriate conditions to allow expression of the peptide to occur. The peptide may be secreted (e.g. through use of recombinantly added signal sequence) and isolated from a mixture of cells and medium containing the secreted protein. Alternatively, the peptide may be retained cytoplasmically, as it presumably is its naturally occurring form, and the cells harvested, lysed and the protein isolated. A cell culture includes host cells, media and other byproducts. Suitable media for cell culture are well known in the art. The subject UbCE polypeptides can be isolated from cell culture medium, host cells, or both using techniques known in the art for purifying proteins including ion-exchange chromatography, gel filtration chromatography, ultrafiltration, electrophoresis, and immunoaffinity purification with antibodies raised against the protein. In a preferred embodiment, the UbCE protein is a fusion protein containing a domain which facilitates its purification, such as the hUbCE-GST fusion protein described below.

Thus, a nucleotide sequence derived from the cloning of a UbCE protein of the present invention, encoding all or a selected portion of the protein, can be used to produce a recombinant form of the enzyme via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant proteins, or portions thereof, by microbial means or tissue-culture technology in accord with the subject invention.

The recombinant protein can be produced by ligating the cloned gene, or a portion thereof, into a vector suitable for expression in either prokaryotic cells, eukaryotic cells, or both. Expression vehicles for production of recombinant UbCEs include plasmids and other vectors. For instance, suitable vectors for the expression of the subject proteins include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning: A Laboratory Manual*, 2nd Ed., ed. by Sambrook, Fritsch and Maniatis (Cold Spring Harbor Laboratory Press:1989) Chapters 16 and 17.

In some instances, it may be desirable to express the recombinant UbCE by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of the ubiquitin-conjugating enzyme is desired, i.e. a truncation mutant, it may be necessary to add, a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing UbCE-derived polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a UbCE protein. In an exemplary embodiment, the VP6 capsid protein of rotavirus can be used as an immunologic carrier protein for portions of the hUbCE polypeptide, either in the monomeric form or in the form of a viral particle. The nucleic acid sequences corresponding to the portion of the hUbCE protein to which antibodies are to be raised can be incorporated into a fusion gene construct which includes coding sequences for a late vaccinia virus structural protein to produce a set of recombinant viruses expressing fusion proteins comprising a portion of the protein hUbCE as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an UbCE protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized, wherein a desired portion of a UbCE protein is obtained directly from organochemical synthesis of the peptide onto an oligomeric branching lysine core (see, for example, Posnett et al. (1988) *J Biol Chem* 263:1719 and Nardelli et al. (1992) *J. Immunol.* 148:914). Antigenic determinants of the UbCE proteins can also be expressed and presented by bacterial cells.

In addition to utilizing fusion proteins to enhance immunogenicity, it is widely appreciated that fusion proteins can also facilitate the expression of proteins, such as the UbCE proteins of the present invention. For example, as described below, the hUbCE protein can be generated as a glutathione-S-transferase (GST) fusion protein. Such GST fusion proteins can enable purification of the hUbCE protein, such as by the use of glutathione-derivatized matrices (see, for example, *Current Protocols in Molecular Biology*, eds. Ausubel et al. (NY: John Wiley & Sons, 1991); Smith et al. (1988) *Gene* 67:31; and Kaelin et al. (1992) *Cell* 70:351). In another embodiment, a fusion gene coding for a purification leader sequence, such as a poly-(His)/enterokinase cleavage site sequence at the N-terminus of the desired portion of the hUbCE protein, can allow purification of the expressed hUbCE-fusion protein by affinity chromatography using a Ni$^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972). Similar constructs can be generated for expression of caUbCE and spUbCE.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons 1992).

Another aspect of the invention pertains to isolated peptides having an activity of the naturally occurring form(s) of the subject UbCE proteins or which are antagonists of at least one biological activity of the naturally occurring form of the subject UbCE proteins. A peptide having an activity of an hUbCE protein has at least one biological activity of an hUbCE protein. As set out above, in preferred embodiments, a biological activity of an hUbCE protein includes an ability to mediate ubiquitination of cellular proteins, such as cell-cycle regulatory proteins, erg. p53, In particular, the hUbCE of the present invention is able to mediate ubiquitin-dependent degradation of p53. Other biological activities of the subject hUbCE protein are described herein or will be reasonably apparent to those skilled in the art. A peptide having at least one biological activity of the subject hUbCE protein may differ in amino acid sequence from the sequence shown in SEQ ID No: 2 but preferably, such differences result in a modified protein which functions in the same or similar manner (e.g. agonist) as a native hUbCE protein or which has the same or similar characteristics of a native hUbCE protein. Furthermore, as described herein, peptides having amino acid sequences homologous to SEQ ID No. 2 yet which function as antagonists of a naturally occurring hUbCE protein are also comtemplated by the present invention. Various modifications of the hUbCE protein to produce these and other functionally equivalent peptides are described in detail herein. In similar fashion, homologs of the subject caUBC and spUBC polypeptides are contemplated, including both agonistic and antagonistic forms. The term peptide, as used herein, refers to peptides, proteins, and polypeptides.

The present invention also makes available isolated UbCE proteins, which proteins are isolated from or otherwise substantially free of other extracellular proteins, especially other proteins of the ubiquitin conjugating system (i.e. other E1 or E2 enzymes, as well as E3 proteins or ubiquitin) normally associated with the ubiquitin-conjugating enzyme in the cellular milleau. The term "substantially free of other extracellular proteins" (also referred to herein as "contaminating proteins") is defined as encompassing preparations of the subject UbCE protein comprising less than 20% (by dry weight) contaminating protein, and preferably comprising less than 5% contaminating protein. Functional forms of the subject UbCE proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other enzymes of the ubiquitin system such as other E1 or E2 proteins, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins or chromatography reagents such as denaturing agents and polymers, e.g. acrylamide or agarose) substances or solutions.

Isolated peptide, having an activity of an UbCE protein, or which can function as antagonists of a naturally occurring form of the UbCE protein described herein can also be obtained by screening peptides recombinantly produced from the corresponding fragment of the nucleic acids encoding such peptides. In addition, fragments can be chemically synthesized using techniques known in the art such as conventional Merrifield solid phase f-Moc or t-Boc chemistry. For example, the hUbCE protein may be arbitrarily divided into fragments of desired length with no overlap of the fragments, or preferably divided into overlapping fragments of a desired length. The fragments can be produced (recombinantly or by chemical synthesis) and tested to identify those peptides having an hUbCE protein activity or alternatively to identify antagonists. Similar manipulation of the caUbCE and soUbCE proteins can be carried out.

Furthermore, it is also possible to modify the structure of a UbCE polypeptide for such purposes as enhancing therapeutic or prophylactic efficacy, or stability (e.g., shelf life ex vivo and resistance to proteolytic degradation in vivo). Such modified peptides are considered functional equivalents of peptides having an activity of, or which antagonize, a UbCE protein as defined herein. A modified polypeptide can be produced in which the amino acid sequence has been altered, such as by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur-containing=cysteine and methionine. (see, for example, *Biochemistry*, 2nd ed, Ed. by L. Stryer, WH Freeman and Co.: 1981). Whether a change in the amino acid sequence of a peptide results in a functional UbCE homolog can be readily determined by assessing the ability of the variant peptide to, for instance, mediate ubiquitination in a fashion similar to the wild-type UbCE. Peptides in which more than one replacement has taken place can readily be tested in the same manner.

The invention also includes a method of generating sets of combinatorial mutants of the subject UbCE proteins, as well as truncation and fragmentation mutants, and is especially useful for identifying potential variant sequences which are functional in ubiquitinating cellular proteins. One purpose for screening such combinatorial libraries is, for example, to isolate novel UbCE homologs which act as antagonist of the wild-type ("authentic") UbCE activity, e.g. an hUbCE homolog which inhibits p53 ubiquitination, or alternatively, possess novel activities all together. Such proteins, when expressed from recombinant DNA constructs, can be used in gene therapy protocols.

Likewise, mutagenesis can give rise to UbCE homologs which have intracellular half-lives dramatically different than the corresponding wild-type protein. For example, the altered protein can be rendered either more stable or less stable to proteolytic degradation or other cellular process which result in destruction of, or otherwise inactivation of, a naturally occurring form of the subject hUbCE protein. Such hUbCE homologs (either agonist or antagonist homologs), and the genes which encode them, can be utilized to alter the envelope of recombinant hUbCE expression by modulating The half-life of the protein. For instance, a short half-life for the recombinant hUbCE can give rise to more transient biological effects associated with that homolog and, when part of an inducible expression system, can allow tighter control of recombinant hUbCE levels within the cell. As above, such proteins, and particularly their recombinant nucleic acid constructs, can be used in gene therapy protocols.

In one aspect of this method, the amino acid sequences for a population of UbCE homologs or other related proteins are aligned, preferably to promote the highest homology possible. Such a population of variants can include, for example, hUbCE homologs from one or more species, or UbCE homologs from the same species but which differ due to mutation. Amino acids which appear at each position of the aligned sequences are selected to create a degenerate set of combinatorial sequences. For instance, alignment of the hUbCE, caUbCE and spUbCE sequences provided in the appended sequence listing (see also FIG. 5) can be used to generate a degenerate library of UbCE proteins represented by the general formula:

Met Xaa(1) Leu Lys Arg Ile Xaa(2) Xaa(3) Glu Leu Xaa(4) Asp Leu Xaa(5) Xaa(6) Asp Pro Pro Xaa(7) Xaa(8) Cys Ser Ala Gly Pro Val Gly Asp Asp Xaa(9) Xaa(10) His Trp Gln Ala Xaa(1 1) Ile Met Gly Pro Asn Asp Ser Pro Tyr Xaa(12) Gly Gly Val Phe Phe Leu Xaa(13) Ile His Phe Pro Thr Asp Tyr Pro Xaa(14) Lys Pro Pro Lys Xaa(15) Xaa(16) Xaa(17) Thr Thr Xaa(18) Ile Tyr His Pro Asn Ile Asn Ser Asn Gly Xaa(19) Ile Cys Leu Asp Ile Leu Xaa(20) Xaa(21) Gln Trp Ser Pro Ala Leu Thr Ile Ser Lys Val Leu Leu Ser Ile Cys Ser Leu Leu Xaa(22) Asp Xaa(23) Asn Pro Asp Asp Pro Leu Val Pro Glu Ile Ala Xaa(24) Xaa(25) Tyr Xaa(26) Xaa(27) Asp Arg Xaa(28) Xaa(29) Tyr Xaa(30) Xaa (31) Xaa(32) Ala Xaa(33) Glu Trp Thr Xaa(34) Lys Tyr Ala Xaa(35) (SEQ ID No. 7)

wherein Xaa(1) represents Ala or Ser; Xaa(2) represents His or Asn; Xaa(3) represents Lys or Arg; Xaa(4) represents Ala, Ser or Asn, Xaa(5) represents Gly or Ala; Xaa(6) represents Arg or Lys; Xaa(7) represents Ala or Ser; Xaa(8) represents Gln or Ser; Xaa(9) represents Leu or Met; Xaa(10) represents Phe or Tyr; Xaa(11) represents Ser or Thr; Xaa(12) represents Gln or Ala; Xaa(13) represents Ser or Thr; Xaa(14) represents Leu or Phe; Xaa(15) represents Val or Ile; Xaa(16) represents Ala or Asn; Xaa(17) represents Leu or Phe; Xaa(18) represents Arg or Lys; Xaa(19) represents Ser or Asn; Xaa(20) represents Arg or Lys; Xaa(21) represents Ser or Asp; Xaa(22) represents Thr or Cys; Xaa(23) represents Ala or Pro; Xaa(24) represents Arg or His; Xaa(25) represents Val or Ile; Xaa(26) represents Lys or Gln; Xaa(27) represents Thr or Gln; Xaa(28) represents Ser, Lys or Glu; Xaa(29) represents Arg or Lys; Xaa(30) represents Asn or Gln; Xaa(31) represents Ala, Leu or Arg; Xaa(32) represents Ile, Ser or Thr; Xaa(33) represents Arg or Lys; Xaa(34) represents Arg, Lys or Gln; Xaa(35) represents Val, Ile or Met.

To further expand the library, each of the degenerate positions (Xaa) can be rendered even more degenerate by including other amino acid residues which are of the same "family" as the residues which appear in each of the UbCEs, e.g. Xaa(1) can be Gly, Ala, Val, Leu, Ile, Ser or Thr (e.g. aliphatic), Xaa(22) can be Ser, Thr, Cys or Met (aliphatic-hydroxyl and sulfur-containing), etc. Alternatively, isosteric substitutions can be made without regard to, for example, charge or polarity of the amino acid sidechain. For instance, Xaa(17) can be Leu, Ile, Asn, Met, Phe or Tyr, as the sidechains of Ile, Asn and Met each occupy approximately the same steric space as Leu, and Tyr is isosteric for Phe. Likewise, where the degeneracy is conserved from the human and yeast homologs, the degenerate libarary can, at that position, only include, for example, the amino acid residue which occurs in the human UbCE. To illustrate, Xaa(3) is a Lysine in hUbCE and caUbCE, and Arginine in spUbCE. In a library which rejects conservative mutations of the human UbCE as equivalent, Xaa(3) would be Lys.

In a preferred embodiment, the combinatorial UbCE library is produced by way of a degenerate library of genes encoding a library of polypeptides which each include at least a portion of potential UbCE sequences. A mixture of synthetic oligonucleotides can be enzymatically ligated into gene sequences such that the degenerate set of potential UbCE sequences are expressible as individual polypeptides, or alternatively, as a set of larger fusion proteins (e.g. for phage display) containing the set of UbCE sequences therein.

There are many ways by which the library of potential UbCE homologs can be generated from a degenerate oligonucleotide sequence. Chemical synthesis of a degenerate gene sequence can be carried out in an automatic DNA synthesizer, and the synthetic genes then be ligated into an appropriate gene for expression The purpose of a degenerate set of genes is to provide, in one mixture, all of the sequences encoding the desired set of potential UbCE sequences. The synthesis of degenerate oligonucleotides is well known in the art (see, for example, Narang, S. A. (1983) *Tetrahedron* 39:3; Itakura et al. (1981) *Recombinant DNA, Proc 3rd Cleveland Sympos. Macromolecules*, ed. A. G. Walton, Amsterdam: Elsevier pp273–289; Itakura et al, (1984) *Annu, Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of UbCE homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of, for example, degenerate hUbCE sequences created by combinatorial mutagenesis techniques.

In one illustrative screening assay, the candidate hUbCE gene products are displayed on the surface of a cell or viral particle, and the ability of particular cells or viral particles to bind other components of the ubiquitin pathway, e.g. E1 or E3 proteins (e.g. E6AP or E6AP complexes), ubiquitin, or p53, via this gene product is detected in a "palming assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind hUbCE can be used to score for potentially functional hUbCE homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

In an illustrative embodiment, the recombinant phage antibody system (RPAS, Pharmacia Catalog number 27-9400-01) can be easily modified for use in expressing and screening hUbCE combinatorial libraries. For instance, the pCANTAB 5 phagemid of the RPAS kit contains the gene which encodes the phage gIII coat protein. The hUbCE combinatorial gene library can be cloned into the phagemid adjacent to the gIII signal sequence such that it will be expressed as a gIII fusion protein. After ligation, the phagemid is used to transform competent E. coli TGI cells. Transformed cells are subsequently infected with M13KO7 helper phage to rescue the phagemid and its candidate hUbCE gene insert. The resulting recombinant phage contain phagemid DNA encoding a specific candidate hUbCE, and display one or more copies of the corresponding fusion coat protein. The phage-displayed candidate hUbCE which are capable of binding a particular target protein, such as an E1 enzyme, an E3 protein (i.e. E6 or E6-AP), or p53, are selected or enriched by panning. For instance, the phage library call be panned on glutathione immobilized p53-GST fusion proteins or E6-GST or E6-AP-GST fusion proteins (described, for example, in U.S. patent application Ser. No. 08/176,937), and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning can be employed to greatly enrich for hUbCE homologs that retain some ability to interact with normal targets of the wild-type hUbCE, and which can then be screened for further biological activities in order to differentiate agonists and antagonists. In an exemplary embodiment, by use of two or more target proteins in sequential panning steps, the phage display library can be used to isolate hUbCE homologs which are candidate antagonists of the normal cellular function of the naturally occurring hUbCE. For instance, isolating from the library those variants which retain the ability to bind, for example, either the papillomavirus E6 protein or the cellular E6-AP protein, but which are unable to bind p53, provides a set of hUbCE homologs some of which may be capable of antagonizing the ability of the wild-type hUbCE to mediate ubiquitination of p53.

In yet another illustrative embodiment, the p53-dependent reporter construct described in the 08/176,937 application can be used to identify antagonists through their ability to enhance expression of the reporter gene by inhibiting the degradation of p53 wild-type hUbCE. Thus, a combinatorial library can screened by a detecting expression of the reporter gene, and appropriate clones isolated for further manipulation.

Other forms of mutagenesis can also be utilized to generate a combinatorial library from the subject UbCE proteins. For example, hUbCE homologs (both agonist and antagonist forms) can be generated and isolated from a library by screening using, for example, alanine scanning mutagenesis and the like (Ruf et al. (1994) Biochemistry 33:1565–1572; Wang et al. (1994) J. Biol. Chem. 269:3095–3099; Balint et al. (1993) Gene 137:109–118; Grodberg et al. (1993) Eur. J. Biochem. 218:597–601; Nagashima et al. (1993) J. Biol. Chem. 268:2888–2892; Lowman et al. (1991) Biochemistry 30:10832–10838; and Cunningham et al. (1989) Science 244:1081–1085), by linker scanning mutagenesis (Gustin et al. (1993) Virology 193:653–660; Brown et al. (1992) Mol. Cell Biol. 12:2644–2652; McKnight et al. (1982) Science 232:316); by saturation mutagenesis (Meyers et al. (1986) Science 232:613); by PCR mutagenesis (Leung et al. (1989) Method Cell Mol Biol 1:11–19); or by random mutagenesis (Miller et al. (1992) A Short Course in Bacterial Genetics, CSHL Press, Cold Spring Harbor, N.Y.; and Greener et al, (1994) Strategies in Mol Biol 7:32–34).

An important goal of the present invention is to provide reduction of the UbCE proteins to small functional units that can be ultimately used to generate UbCE mimetics, e.g. peptide or non-peptide agents, which are able to disrupt binding of UbCE with other cellular and/or viral proteins. Thus, such mutagenic techniques as described herein are particularly useful to map the determinants of the hUbCE protein which participate in protein-protein interactions involved in, for example, binding of the subject hUbCE to other proteins of the ubiquitin-conjugating system (both cellular and viral), as well as the target protein itself (e.g. p53). To illustrate, the critical residues of hUbCE involved in molecular recognition of E6 and/or E6-AP can be determined and used to generate hUbCE-derived peptidomimetics which competitively inhibit hUbCE binding. By employing, for example, scanning mutagenesis to map the amino acid residues of hUbCE involved in binding E6AP, peptidomimetic compounds can be generated which mimic those residues in binding to E6AP, and which therefore can inhibit binding of the hUbCE to E6AP and interfere with the function of E6AP in regulating the cellular half-life of p53. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher Leiden, Netherlands, 1988), substituted gama lactam rings (Garvey et al. in Peptides. Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71). Such peptidomimetics can serve as drugs which prevent the action of hUbCE in the destruction of, for example, p53. Furthermore, such data concerning protein-protein interactions can be used in conjunction with the molecular model of hUbCE described below for rational design of mimetics of this interaction. In like manner, peptidomimetics of caUbCE and spUbCE can be derived which may be useful in, for example, the generation of anti-mycotic agents.

Another aspect of the invention pertains to an antibody specifically reactive with the subject UbCE proteins. For example, by using immunogens derived from the hUbCE protein of the present invention, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g.) the whole hUbCE protein or an antigenic fragment which is capable of eliciting an antibody response). Techniques for conferring immunogenicity on a protein or peptide include conjugation to carriers or other techniques well known in the art. An immunogenic portion of the subject UbCE protein can be administered in the presence of adjuvant. The progress of immunization can be monitored by detection of antibody titers in plasma or serum. Standard ELISA or other immunoassays can be used with the immunogen as an antigen to assess the levels of antibodies In a preferred embodiment, the subject antibodies are immunospecific for hUbCE antigenic determinants, e.g. antigenic determinants of a protein represented by SEQ ID No. 2 or a closely related human or non-human mammalian homolog (e.g. 90 percent homologous to SEQ ID No. 2, preferably at least 95 percent homologous and more preferably at least 97 percent homologous to SEQ ID No. 2). In yet a further preferred embodiment of the present invention, the anti-hUbCE antibodies does not substantially cross react with a protein which is: e.g. less than 90 percent homologous with SEQ ID No. 2; e.g. less than 95 percent homologous with SEQ ID No. 2; e.g. less than 98–99 percent homologous with SEQ ID No. 2. By "does not substantially cross-react", it is meant that: the antibody has a binding affinity for a non-homologous E2 enzyme which is less than 10 percent, more preferably less than 5 percent, and most preferably less than about 1–2 percent of the binding affinity of that antibody for the protein of SEQ ID No. 2; the antibody does not specifically bind a protein which is non-homologous to SEQ ID No. 2. Preferred antibodies against the subject caUbCE and spUbCE proteins have similar criteria, e.g., antibodies specific for caUbCE or spUbCE do not specifically bind proteins which do not share high sequence homology with SEQ ID No. 4 or 6, respectively.

Following immunization, anti-UbCE antisera can be obtained and, if desired, polyclonal anti-UbCE antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256:495–497), the human B cell hybridoma technique (Kozbar et al., (1983) *Immunology Today*: 4:72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the subject UbCE protein and monoclonal antibodies isolated from a culture comprising such hybridoma cells.

The term antibody as used herein is intended to include fragments thereof which are also specifically reactive with the UbCE proteins of the present invention. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-UbCE portion.

Both monoclonal and polyclonal antibodies (Ab) directed against the subject ubiquitin conjugating enzymes, and antibody fragments such as Fab' and F(ab')$_2$, can be used as specialty chemicals to block the action of the enzyme and allow the study of, for example, the cell cycle or cell proliferation when the subject UbCE is inhibited, e.g. by microinjection of anti-UbCE antibodies.

Antibodies which specifically bind hUbCE epitopes can also be used in immunohistochemical staining of tissue samples in order to evaluate the abundance and pattern of expression of hUbCE. Anti-hUbCE antibodies can be used diagnostically in immuno-precipitation and immunoblotting to detect and evaluate hUbCE levels in tissue or bodily fluid as part of a clinical testing procedure For instance, such measurements can be useful in predictive valuations of the onset or progression of tumors. Likewise, the ability to monitor hUbCE levels in an individual can allow determination of the efficacy of a given treatment regimen for an individual afflicted with such a disorder. The level of hUbCE can be measured in cells isolated from bodily fluid, such as in samples of cerebral spinal fluid or blood, or can be measured in tissue, such as produced by biopsy. Diagnostic assays using anti-hUbCE antibodies can include, for example, immunoassays designed to aid in early diagnosis of a neoplastic or hyperplastic disorder, e.g. the presence of cancerous cells in the sample, e.g. to detect cells in which a lesion of the hUbCE gene has occurred.

Another application of anti-UbCE antibodies is in the immunological screening of cDNA libraries constructed in expression vectors, such as λgt11, λt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of UbCE can then be detected with antibodies, as, for example, reacting nitrocellulose filters lifted from infected plates with anti-UbCE antibodies. Phage, scored by this assay, can then be isolated from the infected plate. Thus, the presence of hUbCE homologs can be detected and cloned from other human sources, i.e. to identified other closely homologous human isoforms, as well as to identify hUbCE homologs in other mammals.

Moreover, the nucleotide sequence determined from the cloning of subject hUbCE from a human cell line will further allow for the generation of probes designed for use in identifying hUbCE homologs in other human cell-types, particularly cancer or other transformed or immortalized cells, as well as hUbCE homologs from other non-human mammals. Probes based on the yeast UbCE sequences, caUbCE and spUbCE can be generated and used to identify and phenotype mycotic infections.

In addition, nucleotide probes can be generated from the cloned sequence of the hUbCE protein, which allow for histological screening of intact tissue and tissue samples for the presence of hUbCE mRNA. Similar to the diagnostic uses of anti-hUbCE antibodies, the use of probes directed to hUbCE mRNA, or to genomic hUbCE sequences, can be used for both predictive and therapeutic evaluation of allelic mutations which might be manifest in, for example, neoplastic or hyperplastic disorders (e.g. unwanted cell growth). Used in conjunction with anti-hUbCE antibody immunoassays, the nucleotide probes can help facilitate the determination of the molecular basis for a developmental disorder which may involve some abnormality associated with expression (or lack thereof) of an hUbCE protein. For instance, variation in hUbCE synthesis can be differentiated from a mutation in the hUbCE coding sequence.

For example, the present method provides a method for determining if a subject is at risk for a disorder characterized by unwanted cell proliferation. In preferred embodiments, the subject method can be generally characterized as comprising detecting, in a tissue of a subject (e.g. a human patient), the presence or absence of a genetic lesion characterized by at least one of (i) a mutation of a gene encoding hUbCE or (ii) the mis-expression of the hUbCE gene. To illustrate, such genetic lesions can be detected by ascertaining the existence of at least one of (i) a deletion of one or more nucleotides from the hUbCE gene, (ii) an addition of one or more nucleotides to the hUbCE gene, (iii) a substitution of one or more nucleotides of the hUbCE gene, (iv) a gross chromosomal rearrangement of the hUbCE gene, (v) a gross alteration in the level of a messenger RNA transcript of the hUbCE gene, (vi) the presence of a non-wild type splicing pattern of a messenger RNA transcript of the hUbCE gene, and (vii) a non-wild type level of the hUbCE protein. In one aspect of the invention there is provided A probe/primer comprising an oligonucleotide containing a region of nucleotide sequence which is capable of hybridizing to a sense or antisense sequence of SEQ ID No: 1 or naturally occurring mutants thereof; or 5 or 3 flanking sequences or intronic sequences naturally associated with the hUbCE gene. The probe is exposed to nucleic acid of a tissue sample; and the hybridization of the probe to the sample nucleic acid is detected. In certain embodiments, detection of the lesion comprises utilizing the probe/primer in, for example, a polymerase chain reaction (PCR) (see, e.g. U.S. Pat. Nos. 4,683,195 and 4,683,202), or, alternatively, in a ligation chain reaction (LCR) (see, e.g., Landegran et al. (1988) *Science* 241:1077–1080; and Nakazawa et al. (1994) *PNAS* 91:360–364), the later of which can be particularly useful for detecting even point mutations in the hUbCE gene. Alternatively, or additionally, the level of hUbCE protein can be detected in an immunoassay.

Also, the use of anti-sense techniques (e.g. microinjection of antisense molecules, or transfection with plasmids whose transcripts are anti-sense with regard to, e.g. UbCE mRNA) can be used to investigate the role of UbCE in the cell cycle and cell proliferation, by inhibiting endogenous UbCE production. Such techniques can be utilized in cell culture, but can also be used in the creation of transgenic animals Another aspect of the present invention concerns transgenic animals, e.g. as animal models for developmental and proliferative diseases, which are comprised of cells (of that animal) which contain a transgene of the present invention and which preferably (though optionally) express the subject UbCE in one or more cells in the animal. In preferred embodiments, the expression of the transgene is restricted to specific subsets of cells, tissues or developmental stages utilizing, for example, cis-acting sequences that control expression in the desired pattern. In the present invention, such mosiac expression of the subject UbCE proteins can be essential for many forms of lineage analysis and can additionally provide a means to assess the effects of UbCE mutations or overexpression that might grossly alter development in small patches of tissue within an otherwise normal embryo. Toward this arid, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, Genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject receptor For example, excision of a target sequence which interferes with the expression of the receptor can be designed to activate expression of that protein. This interference with expression of the subject protein can result from a variety of mechanisms, such as spatial separation of the UbCE gene from the promoter element or an internal stop codon. Moreover, the transgene can be made wherein the coding sequence of the UbCE gene is flanked by recombinase recognition sequences and is initially transfected into cells in a 3' to 5' orientation with respect to the promoter element. In such an instance, inversion of the target sequence will reorient the subject UbCE gene by placing the 5' end of the coding sequence in an orientation with respect to the promoter element which allow for promoter driven transcriptional activation.

In an illustrative embodiment, either the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the recombinant UbCE gene can be regulated via regulation of recombinase expression.

Use of the these recombinase system to regulate expression of, for example, a dominant negative UbCE gene, such as the Cys85Ser mutant or an antisense gene, requires the construction of a transgenic animal containing transgenes encoding both the Cre recombinase and the subject gene. Animals containing both the Cre recombinase and the UbCE genes can be provided through the construction of "double" transgenic animals. A convenient method for providing such animals is to mate two transgenic animals each containing a transgene, e.g., the UbCE gene and recombinase gene.

One advantage derived from initially constructing transgenic animals containing a UbCE transgene in a recombinase-mediated expressible format derives from the likelihood that the subject UbCE protein, whether antagonistic or agonistic, will be deleterious upon expression in the transgenic animal. In such an instance, a founder population, in which the subject transgene is silent in all tissues can be propagated and maintained. Individuals of this founder population can be crossed with animals expressing the recombinase in, for example, one or more tissues. Thus, the creation of a founder population in which the UbCE transgene is silent will allow the study of, for example, the role of the p53 checkpoint in tissue or at developmental stages which can confer, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins arc given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the transgene could remain silent into adulthood until "turned on" by the introduction of the trans-activator.

Methods of making knock-out or disruption transgenic animals are also generally known. See, for example, *Manipulating the Mouse Embryo*, (Cold Spring Harbor Laboratory Press, Cold Spring Harbor, N,Y., 1986).

Furthermore, the present invention, by making available purified and recombinant forms of the subject UbCE proteins, will allow the development of assays which can be used to screen for drugs which are either agonists or antagonists. For instance, in addition to agents which disrupt binding of the hUbCE protein to other cellular (or viral) proteins, inhibitors of the enzymatic activity of the subject hUbCE can be used to prevent transfer of ubiquitin to hUbCE and/or inhibit any downstream transfer of ubiquitin from hUbCE (e.g. to p53 or an intermediary E3 complex, e.g. E6/E6-AP). In a preferred embodiment, the hUbCE inhibitor is a mechanism based inhibitor which chemically alters the enzyme, e.g. covalently binds Cys-85, and which is a specific inhibitor of hUbCE, e.g. has an inhibition constant 10-fold, 100-fold, or more preferably, 1000-fold different for human E2 enzymes other than the subject hUbCE protein. Inhibitor specificity can be improved, for example, by utilizing specificity subsites of the hUbCE enzyme involved in interactions between hUbCE and p53 or hUbCE and E1, which are unique to one of those complexes relative to other human E2 enzymes.

Assays for the measurement of ubiquitination are disclosed in U.S. patent application Ser. No. 08/176,937, filed on Jan. 4, 1994, and herein incorporated by reference. Such assays can be used in conjunction with the subject hUbCE protein to generate a ubiquitin-conjugating system to detect agents able to inhibit hUbCE-mediated ubiquitination of a cellular or target protein. Such agents can be used to, for example, treat papillomavirus infected cells. Similar assay systems can be constructed for the fungal UbCEs in order to detect inhibitors which may serve as anti-fungal agents. In preferred embodiments, the assay system employed for identifying anti-fungal agents are run side-by-side with the analogous assay system derived with hUbCE. Differential screening assays can be used to exploit any difference in mechanism or specificity between mammalian UbCEs and yeast UbCEs (including other yeast E2 enzymes) in order to identify agents which display a statistically significant increase in specificity for inhibiting the yeast enzymes relative to the mammalian enzymes. Thus, lead compounds which act specifically on pathogens, such as fungus involved in mycotic infections, can be developed.

Additionally, the subject ubiquitin conjugating enzyme can be used to generate an interaction trap assay for subsequently detecting inhibitors of hUbCE biological activity (see, for example, U.S. Pat. No: 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696) In an illustrative embodiment, *Saccharomyces cerevisiae* YPB2 cells are transformed simultaneously with a plasmid encoding a GAL4db-hUbCE fusion and with a plasmid encoding the GAL4ad domain fused to p53t or E6AP. Moreover, the strain is transformed such that the GAL4-responsive promoter drives expression of a phenotypic marker. For example, the ability to grow in the absence of histidine can depends on the expression of the HIS3 gene if it is under control of a GAL4-responsive promoter and, therefore, indicates that a functional GAL4 activator has been reconstituted through the interaction of hUbCE and p53 or E6AP. Thus, agent able to inhibit hUbCE interaction with one of these proteins will result in yeast cells unable to growth in the absence of histidine. Alternatively, the phenotypic marker can be one which provides a negative selection when expressed such that agents which disrupt the hUbCE interactions confer positive growth selection to the cells.

Another aspect of the present invention concerns three-dimensional molecular models of the subject UbCE proteins, and their use as templates for the design of agents able to inhibit at least one biological activity of the ubiquitin conjugating enzyme. An integral step to our approach to designing inhibitors of the subject ubiquitin-conjugating enzyme involves construction of computer graphics models of the ubiquitin conjugating enzyme which can be used to design pharmacophores by rational drug design. For instance, for an inhibitor to interact optimally with the subject enzyme, it will generally be desirable that it have a shape which is at least partly complimentary to that of a particular binding site of the enzyme, as for example those portions of the human ubiquitin conjugating enzyme which are involved in recognition of ubiquitin, an E1 enzyme, an E3 protein(s) such as E6 or E6AP, or a downstream target of the pathway, such as p53. Additionally, other factors, including electrostatic interactions, hydrogen bonding, hydrophobic interactions, desolvation effects, and cooperative motions of ligand and enzyme, all influence the binding effect and should be taken into account in attempts to design bioactive inhibitors.

As described in Example 4, a computer-generated molecular model of the subject enzymes can be created. In preferred embodiments, at least the C$\alpha$-carbon positions of the UbCE sequence of interest are mapped to a particular coordinate pattern, such as the coordinates for hUbCE shown in FIG. 1, by homology modeling, and the structure of the protein and velocities of each atom are calculated at a simulation temperature ($T_o$) at which the docking simulation is to be determined. Typically, such a protocol involves primarily the prediction of side-chain conformations in the modeled protein, while assuming a main-chain trace taken from a tertiary structure such as provided in FIG. 1. Computer programs for performing energy minimization routines are commonly used to generate molecular models. For example, both the CHARMM (Brooks et al. (1983) *J Comput Chem* 4:187–217) and AMBER (Weiner et al (1981) *J. Comput. Chem.* 106:765) algorithms handle all of the molecular system setup, force field calculation, and analysis (see also, Eisenfield et al. (1991) *Am J Physiol* 261:C376–386; Lybrand (1991) *J Pharm Belg* 46:49–54; Froimowitz (1990) *Biotechniques* 8:640–644; Burbam et al. (1990) *Proteins* 7:99–111; Pedersen (1985) *Environ Health Perspect* 61:185–190; and Kini et al. (1991) *J Biomol Struct Dyn* 9:475–488). At the heart of these programs is a set of subroutines that, given the position of every atom in the model, calculate the total potential energy of the system and the force on each atom. These programs may utilize a starting set of atomic coordinates, such as the model coordinates provided in FIG. 1, the parameters for the various terms of the potential energy function, and a description of the molecular topology (the covalent structure). Common features of such molecular modeling methods include: provisions for handling hydrogen bonds and other constraint forces; the use of periodic boundary conditions; and provisions for occasionally adjusting positions, velocities, or other parameters in order to maintain or change temperature, pressure, volume, forces of constraint, or other externally controlled conditions.

Most conventional energy minimization methods use the input data described above and the fact that the potential energy function is an explicit, differentiable function of Cartesian coordinates, to calculate the potential energy and its gradient (which gives the force on each atom) for any set of atomic positions. This information can be used to generate a new set of coordinates in an effort to reduce the total potential energy and, by repeating this process over and over, to optimize the molecular structure under a given set of external conditions. These energy minimization methods are routinely applied to molecules similar to the subject UbCE proteins as well as nucleic acids, polymers and zeolites.

In general, energy minimization methods can be carried out for a given temperature, $T_i$, which may be different than the docking simulation temperature, $T_o$. Upon energy minimization of the molecule at Ti, coordinates and velocities of all the atoms in the system are computed. Additionally, the normal modes of the system are calculated. It will be appreciated by those skilled in the art that each normal mode is a collective, periodic motion, with all parts of the system moving in phase with each other, and that the motion of the molecule is the superposition of all normal model. For a given temperature, the mean square amplitude of motion in a particular mode is inversely proportional to the effective force constant for that mode, so that the motion of the molecule will often be dominated by the low frequency vibrations.

After the molecular model has been energy minimized at $T_i$, the system is "heated" or "cooled" to the simulation temperature, $T_o$, by carrying out an equilibration run where the velocities of the atoms are scaled in a step-wise manner until the desired temperature, $T_o$, is reached. The system is further equilibrated for a specified period of time until certain properties of the system, such as average kinetic energy, remain constant. The coordinates and velocities of each atom are then obtained from the equilibrated system.

Further energy minimization routines can also be carried out. For example, a second class of methods involves calculating approximate solutions to the constrained EOM for the protein. These methods use an iterative approach to solve for the Lagrange multipliers and, typically, only need a few iterations if the corrections required are small. The most popular method of this type, SHAKE (Ryckaert et al. (1977) *J Comput Phys* 23:327; and Van Gunsteren et al. (1977) *Mol Phys* 34:1311) is easy to implement and scales as O(N) as the number of constraints increases. Therefore, the method is applicable to macromolecules such as the UbCE proteins of the present invention. An alternative method, RATTLE (Anderson (1983) *J Comput Phys* 52:24) is based on the velocity version of the Verlet algorithm. Like SHAKE, RATTLE is an iterative algorithm and can be used to energy minimize the model of the subject protein.

The increasing availability of biomacromolecule structures of potential pharmacophoric molecules that have been solved crystallographically has prompted the development of a variety of direct computational methods for molecular design, in which the steric and electronic properties of substrate binding sites are use to guide the design of potential inhibitors (Cohen et al. (1990) *J. Med. Cam.* 33:883–894; Kuntz et al. (1982) *J. Mol. Biol* 161:269–288; DesJarlais (1988) *J. Med. Cam.* 31:722–729; Bartlett et al, (1989) (*Spec. Publ., Roy. Soc. Chem.*) 78:182–196; Goodford et al. (1985) *J. Med. Cam.* 28:849–857; DesJarlais et al. *J Med. Cam.* 29:2149–2153). Directed methods generally fall into two categories: (1) design by analogy in which 3-D structures of known molecules (such as from a crystallographic database) are docked to the enzyme structure and scored for goodness-of-fit; and (2) de novo design, in which the ligand model is constructed piece-wise in the enzyme. The latter approach, in particular, can facilitate the development of novel molecules, uniquely designed to bind to the subject human ubiquitin-conjugating enzyme.

In an illustrative embodiment, the design of potential hUbCE inhibitors begins from the general perspective of shape complimentary for the active site and substrate specificity subsites of the enzyme, and a search algorithm is employed which is capable of scanning a database of small molecules of known three-dimensional structure for candidates which fit geometrically into the target protein site. It is not expected that the molecules found in the shape search will necessarily be leads themselves, since no evaluation of chemical interaction necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that atom types will be changed to maximize the electrostatic, hydrogen bonding, and hydrophobic interactions with the enzyme. Most algorithms of this type provide a method for finding a wide assortment of chemical structures that are complementary to the shape of a binding site of the subject enzyme. Each of a set of small molecules from a particular data-base, such as the Cambridge Crystallographic Data Bank (CCDB) (Allen et al. (1973) *J. Chem. Doc.* 13:119), is individually docked to the binding site of the hUbCE enzyme in a number of geometrically permissible orientations with use of a docking algorithmn. In a preferred embodiment, a set of computer algorithms called DOCK, can be used to characterize the shape of invaginations and grooves that form the active sites and recognition surfaces of the subject enzyme (Kuntz et al. (1982) *J. Mol. Biol* 161:269–288). The program can also search a database of small molecules for templates whose shapes are complementary to particular binding sites of the enzyme (DesJarlais et al. (1988) *J Med Chem* 31:722–729). These templates normally require modification to achieve good chemical and electrostatic interactions (DesJarlais et al. (1989) *ACS Symp Ser* 413:60–69). However, the program has been shown to position accurately known cofactors for inhibitors based on shape constraints alone.

The orientations are evaluated for goodness-of-fit and the best are kept for further examination using molecular mechanics programs, such as AMBER or CHARMM. Such algorithms have previously proven successful in finding a variety of molecules that are complementary in shape to a given binding site of a receptor-enzyme, and have been shown to have several attractive features. First, such algorithms can retrieve a remarkable diversity of molecular architectures. Second, the best structures have, in previous applications to other proteins, demonstrated impressive shape complementarity over an extended surface area. Third, the overall approach appears to be quite robust with respect to small uncertainties in positioning of the candidate atoms.

Goodford (1985, *J Med Chem* 28:849–857) and Boobbyer et al. (1989, *J Med Chem* 32:1083–1094) have produced a computer program (GRID) which seeks to determine regions of high affinity for different chemical groups (termed probes) on the molecular surface of the binding site. GRID hence provides a tool for suggesting modifications to known ligands that might enhance binding. It may be anticipated that some of the sites discerned by GRID as regions of high affinity correspond to "pharmacophoric patterns" determined inferentially from a series of known ligands. As used herein, a pharmacophoric pattern is a geometric arrangement of features of the anticipated ligand that is believed to be important for binding. Attempts have been made to use pharmacophoric patterns as a search screen for novel ligands (Jakes et al. (1987) *J Mol Graph* 5:41–48; Brint et al. (1987) *J Mol Graph* 5:49–56; Jakes et al. (1986) *J Mol Graph* 4:12–20); however, the constraint of steric and "chemical" fit in the putative (and possibly unknown) receptor binding site is ignored. Goodsell and Olson (1990, *Proteins: Struct Funct Genet* 8:195–202) have used the Metropolis (simulated annealing) algorithm to dock a single known ligand into a target protein. They allow torsional flexibility in the ligand and use GRID interaction energy maps as rapid lookup tables for computing approximate interaction energies. Given the large number of degrees of freedom available to the ligand, the Metropolis algorithm is time-consuming and is unsuited to searching a candidate database of a few thousand small molecules.

Yet a further embodiment of the present invention utilizes a computer algorithm such as CLIX which searches such databases as CCDB for small molecules which can be oriented in the receptor binding site in a way that is both sterically acceptable and has a high likelihood of achieving favorable chemical interactions between the candidate molecule and the surrounding amino acid residues. The method is based on characterizing the receptor site in terms of an ensemble of favorable binding positions for different chemical groups and then searching for orientations of the candidate molecules that cause maximum spatial coincidence of individual candidate chemical groups with members of the ensemble. The current availability of computer power dictates that a computer-based search for novel ligands follows a breadth-first strategy. A breadth-first strategy aims to reduce progressively the size of the potential candidate search space by the application of increasingly stringent criteria, as opposed to a depth-first strategy wherein a maximally detailed analysis of one candidate is performed before proceeding to the next. CLIX conforms to this strategy in that its analysis of binding is rudimentary—it seeks to satisfy the necessary conditions of steric fit and of having individual groups in "correct" places for bonding, without imposing the sufficient condition that favorable bonding interactions actually occur. A ranked "shortlist" of molecules, in their favored orientations, is produced which can then be examined on a molecule-by-molecule basis, using computer graphics and more sophisticated molecular modeling techniques. CLIX is also capable of suggesting changes to the substituent chemical groups of the candidate molecules that might enhance binding.

The algorithmic details of CLIX is described in Lawerence et al. (1992) *Proteins* 12:31–41, and the CLIX algorithm can be summarized as follows. The GRID program is used to determine discrete favorable interaction positions (termed target sites) in the binding site of the protein for a wide variety of representative chemical groups. For each candidate ligand in the CCDB an exhaustive attempt is made to make coincident, in a spatial sense in the binding site of the protein, a pair of the candidate's substituent chemical groups with a pair of corresponding favorable interaction sites proposed by GRID. All possible combinations of pairs of ligand groups with pairs of GRID sites are considered during this procedure. Upon locating such coincidence, the program rotates the candidate ligand about the two pairs of groups and checks for steric hindrance and coincidence of other candidate atomic groups with appropriate target sites. Particular candidate/orientation combinations that are good geometric fits in the binding site and show sufficient coincidence of atomic groups with GRID sites are retained.

Consistent with the breadth-first strategy, this approach involves simplifying assumptions. Rigid protein and small molecule geometry is maintained throughout. As a first approximation rigid geometry is acceptable as the energy minimized coordinates of the hUbCE deduced structure, as described in Example 4, describe an energy minimum for the molecule, albeit a local one. If the surface residues of the site of interest are not involved in crystal contacts then the crystal configuration of those residues. We believe that the deduced structure described in Example 4 should reasonably mimic the mean solution configuration. Moreover, the equivalent models of caUbCE and spUbCE can be derived by the same method.

A further assumption implicit in CLIX is that the potential ligand, when introduced into the binding site of ubiquitin-conjugating enzyme, does not induce change in the protein's stereochemistry or partial charge distribution and so alter the basis on which the GRID interaction energy maps were computed. It must also be stressed that the interaction sites predicted by GRID are used in a positional and type sense only, i.e., when a candidate atomic group is placed at a site predicted as favorable by GRID, no check is made to ensure that the bond geometry, the state of protonation, or the partial charge distribution favors a strong interaction between the protein and that group. Such detailed analysis should form part of more advanced modeling of candidates identified in the CLIX shortlist.

Yet another embodiment of a computer-assisted molecular design method for identifying inhibitors of the subject ubiquitin-conjugating enzyme comprises the de novo synthesis of potential inhibitors by algorithmic connection of small molecular fragments that will exhibit the desired structural and electrostatic complementarity with the active site of the enzyme. The methodology employs a large template set of small molecules with are iteratively pieced together in a model of the UbCE active site. Each stage of ligand growth is evaluated according to a molecular mechanics-based energy function, which considers van der Waals and coulombic interactions, internal strain energy of the lengthening ligand, and desolvation of both ligand and enzyme. The search space can be managed by use of a data tree which is kept under control by pruning according to the binding criteria.

In an illustrative embodiment the search space is limited to consider only amino acids and amino acid analogs as the molecular building blocks. Such a methodology generally employs a large template set of amino acid conformations, though need not be restricted to just the 20 natural amino acids, as it can easily be extended to include other related fragments of interest to the medicinal chemist, e.g. amino acid analogs. The putative ligands that result from this construction method are peptides and peptide-like compounds rather than the small organic molecules that are typically the goal of drug design research. The appeal of the peptide building approach is not that peptides are preferable to organics as potential pharmaceutical agents, but rather that: (1) they can be generated relatively rapidly de novo; (2) their energetics can be studied by well-parameterized force field methods; (3) they are much easier to synthesize than are most organics; and (4) they can be used in a variety of ways, for peptidomimetic inhibitor design, protein-protein binding studies, and even as shape templates in the more commonly used 3D organic database search approach described above.

Such a de novo peptide design method has been incorporated in a software package called GROW (Moon et al. (1991) *Proteins* 11:314–328). In a typical design session, standard interactive graphical modeling methods are employed to define the structural environment in which GROW is to operate For instance, environment could be the active site cleft of hUbCE, or it could be a set of features on the protein's surface to which the user wishes to bind a peptide-like molecule, e.g. a ubiquitin, p53, E6 or E6AP mimetic. The GROW program then operates to generate a set of potential ligand molecules. Interactive modeling methods then come into play again, for examination of the resulting molecules, and for selection of one or more of them for further refinement.

To illustrate, GROW operates on an atomic coordinate file generated by the user in the interactive modeling session, such as the coordinates provided in FIG. 1, or the coordinates of the active site provided in FIG. 3, plus a small fragment (e.g., an acetyl group) positioned in the active site to provide a starting point for peptide growth. These are referred to as "site" atoms and "seed" atoms, respectively. A second file provided by the user contains a number of control parameters to guide the peptide growth (Moon et al. (1991) *Proteins* 11:314–328).

Figure 4:
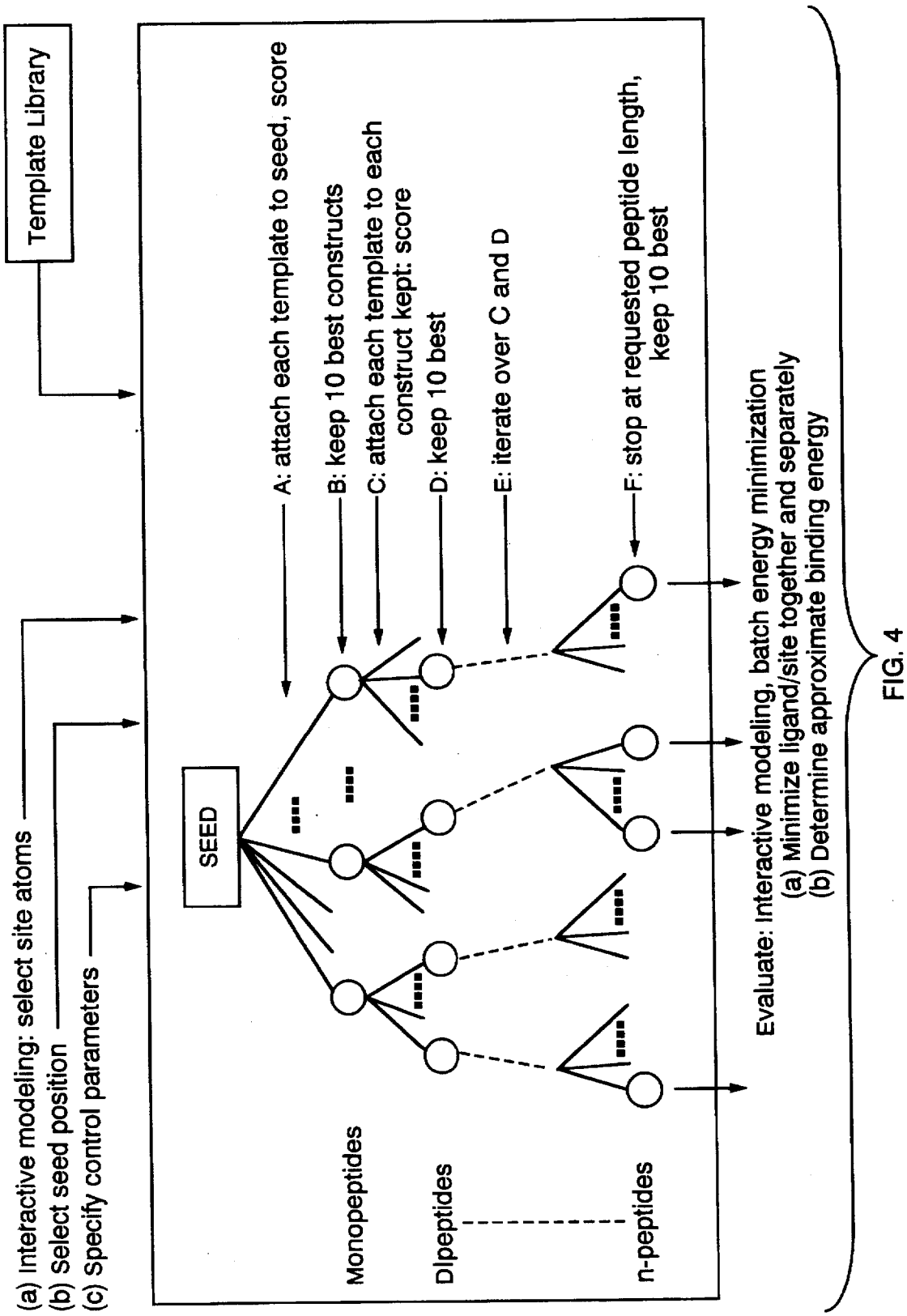
FIG. 4 is the schematic overview of the operation of the GROW method of drug design. The site and seed coordinate file and command file are provided to the GROW procedure by the user. Growth can be visualized as a tree process in which each library template is attached to the seed (A) and then evaluated by the scoring function (e.g. binding criteria). Of the resulting constructs, a given number of best constructs (e.g. 10) are kept for the next level (B). To each retained monopeptide/seed construct are attached all library templates, which are again scored (C). After pruning(D), the process is repeated (E) until the specified peptide length is reached (F). In this tree diagram, circles represent those nodes selected (based on best binding criteria evaluation) for further growth. Uncircled nodes are pruned. Horizontal dots denote continuation across all template additions (e.g. other members of a series), and vertical dots represent the iterative process of tree growth.

The operation of the GROW algorithm is conceptually fairly simple, and is summarized in FIG. 4. GROW proceeds in an iterative fashion, to systematically attach to the seed fragment each amino acid template in a large preconstructed library of amino acid conformations. When a template has been attached, it is scored for goodness-of-fit to the receptor site, and then the next template in the library is attached to the seed. After all the templates have been tested, only the highest scoring ones are retained for the next level of growth. This procedure is repeated for the second growth level; each library template is attached in turn to each of the bonded seed/amino acid molecules that were retained from the first step, and is then scored. Again, only the best of the bonded seed/dipeptide molecules that result are retained for the third level of growth. The growth of peptides can proceed in the N-to-C direction only, the reverse direction only or in alternating directions, depending on the initial control specifications supplied by the user. Successive growth levels therefore generate peptides that are lengthened by one residue. The procedure terminates when the user-defined peptide length has been reached, at which point the user can select from the constructed peptides those to be studied further The resulting data provided by the GROW procedure include not only residue sequences and scores, but also atomic coordinates of the peptides, related directly to the coordinate system of the receptor site atoms.

In yet another embodiment, potential, pharmacophoric compounds can be determined using a method based on an energy minimization-quenched molecular dynamics algorithm for determining energetically favorable positions of functional groups in the binding cites of the subject ubiquitin-conjugating enzyme. The method can aid in the design of molecules that incorporate such functional groups by modification of known ligands or de novo construction.

For example, the multiple copy simultaneous search method (MCSS) described by Miranker et al. (1991) *Proteins* 11:29–34. To determine and characterize a local minima of a functional group in the forcefield of the protein, multiple copies of selected functional groups are first distributed in a binding site of interest on the UbCE protein. Energy minimization of these copies by molecular mechanics or quenched dynamics yields the distinct local minima. The neighborhood of these minima can then be explored by a grid search or by constrained minimization. In one embodiment, the MCSS method uses the classical time dependent Hartee (TDH) approximation to simultaneously minimize or quench many identical groups in the forcefield of the protein.

Implementation of the MCSS algorithm requires a choice of functional groups and a molecular mechanics model for each of them. Groups must be simple enough to be easily characterized and manipulated (3–6 atoms, few or no dihedral degrees of freedom), yet complex enough to approximate the steric and electrostatic interactions that the functional group would have in binding to the site of interest in the UbCE protein. A preferred set is, for example, one in which most organic molecules can be described as a collection of such groups (*Patai's Guide to the Chemistry of Functional Groups*, ed. S. Patai (New York: John Wiley, and Sons, (1989)). This includes fragments such as acetonitrile, methanol, acetate, methyl ammonium, dimethyl ether, methane, and acetaldehyde.

Determination of the local energy minima in the binding site requires that many starting positions be sampled. This can be achieved by distributing, for example, 1,000–5,000 groups at random inside a sphere centered on the binding site; only the space not occupied by the protein needs to be considered. If the interaction energy of a particular group at a certain location with the protein is more positive than a given cut-off (e.g. 5.0 kcal/mole) the group is discarded from that site. Given the set of starting positions all the fragments are minimized simultaneously by use of the TDH approximation (Elber et al. (1990) *J Am Chem Soc* 112:9161–9175).

In this method, the forces on each fragment consist of its internal forces and those due to the protein. The essential element of this method is that the interactions between the fragments are omitted and the forces on the protein are normalized to those due to a single fragment. In this way simultaneous minimization or dynamics of any number of functional groups in the field of a single protein can be performed.

Minimization is performed successively on subsets of, eg. 100, of the randomly placed groups. After a certain number of step intervals, such as 1,000 intervals, the results can be examined to eliminate groups converging to the same minimum. This process is repeated until minimization is complete (e.g. RMS gradient of 0.01 kcal/mole/Å). Thus the resulting energy minimized set of molecules comprises what amounts to a set of disconnected fragments in three dimensions representing potential pharmacophores.

The next step then is to connect the pharmacophoric pieces with spacers assembled from small chemical entities (atoms, chains, or ring moieties). In a preferred embodiment, each of the disconnected can be linked in space to generate a single molecule using such computer programs as, for example, NEWLEAD (Tschinke et al. (1993) *J Med Chem* 36:3863,3870). The procedure adopted by NEWLEAD executes the following sequence of commands (1) connect two isolated moieties, (2) retain the intermediate solutions for further processing, (3) repeat the above steps for each of the intermediate solutions until no disconnected units are found, and (4) output the final solutions, each of which is a single molecule. Such a program can use for example, three types of spacers: library spacers, single-atom spacers, and fuse-ring spacers The library spacers are optimized structures of small molecules such as ethylene, benzene and methylamide. The output produced by programs such as NEWLEAD consist of a set of molecules containing the original fragments now connected by spacers. The atoms belonging to the input fragments maintain their original orientations in space. The molecules are chemically plausible because of the simple makeup of the spacers and functional groups, and energetically acceptable because of the rejection of solutions with van-der Waals radii violations.

In one embodiment of the invention, the target regulatory protein is the tumor suppressor p53, and any one of the above assays or molecular modeling protocols is used to identify inhibitors of ubiquitin-mediated destruction of p53, such as by disrupting interaction of hUbCE with p53, or interactions between hUbCE an other proteins of the ubiquitin system such as E6 or E6AP, or alternatively, by mechanistically inhibiting the enzymatic activity of the enzyme. Many lines of evidence point to the importance of p53 in human carcinogenesis. For instance, mutations within the p53 gene are the most frequent genetic aberration thus far associated with human cancer Although p53 can block the progression of the cell cycle when artificially expressed at high levels, it appears to be dispensable for normal development. Thus, for mice containing homozygous deletions and humans harboring germline mutations of p53, development is normal and p553 protein is expressed at very low levels in most cell types. Emerging evidence, however, suggests that p53 is a checkpoint protein that plays an important role in sensing DNA damage or regulating cellular response to stress. Under normal conditions, p53 is an unstable protein and is present at very low levels in the cell, and the level of p53 in a cell appears to be controlled at least in party by degradation involving the ubiquitin system and, based on data presented herein, is likely to be mediated by the subject hUbCE. Treating cells with UV light or X rays dramatically reduces the rate of p53 degradation, leading to a rapid increase in its concentration in the cell and presumably inducing the transcription of genes that block passage through the restriction point. However, while normal cell lines irradiated in $G_1$ fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins. An inhibitor developed using the subject hUbCE in a ubiquitin-conjugating assay or by rational drug design could subsequently be used therapeutically to enhance the function of the p53 checkpoint by increasing the steady state concentration of p53 in the treated cell. Given that elevated levels of wild-type p53 protein can lead to apoptosis in a variety of transformed cell types (Yonish-Rouach et al. (1991) *Nature* 352:345–347; Shaw et al. *PNAS* 89:4495–4499; and Caelles et al. (1994) *Nature* 370:220–223), inhibitors of hUbCE-mediated degradation of p53 may be attractive therapeutic agents not only in cervical cancer, but also other cancer types, by increasing the fortitude of the checkpoint in transformed cells which contain wild-type p53, or by offsetting a diminishment in p53 activity by increasing the level of (mutant) p53. Moreover, such agents can also be used prophylactically in normal cells to increase p53 levels and thereby enhance the protection against DNA damaging agents when it is known that exposure to damaging agents, such as radiation, is imminent.

Moreover, the oncogenic activity of certain viruses, such as the simian virus 40 (SV40), the adenovirus type 5 (Ad5), and the high human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppressor protein. This models accounts for the observations that p53 levels are very low in HPV-immortalized cells and that the half-life of p53 in HPV16-immortalized keratinocytes is shorter than in primary keratinocytes. Thus, the present invention can be employed in the identification of an agent that can block the ubiquitin dependent degradation of p53 as mediated by E6, and thereby block proliferation of HPV-transformed cells.

The subject human ubiquitin conjugating enzyme is likely to be involved in altering the activity of other cellular proteins, particularly proteins which seem to have short half-lives, and the present invention contemplates the use of hUbCE inhibitors, including antagonistic forms of the hUbCE protein, to inhibit the ubiquitination of other cellular proteins by hUbCE. For example, in another embodiment, the regulatory protein ubiquitinated by hUbCE is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. Myc has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In tumor cells, on the other hand, elevated or deregulated expression of c-myc is so widespread as to suggest a critical role for myc gene activation in multi-stage carcinomas (Field et all. (1990) *Anticancer Res* 10:1–22; and Spencer et al. (1991) *Adv Cancer Res* 56:1–48). However, such over-expression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10:1153–1159; and Lennon et al. (1990) *Biochem Soc Trans* 18:343–345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur even in the absence of a second cytotoxic drug.

The regulation of cyclin by ubiquitination is yet another therapeutic target which may implicate hUbCE inhibitors. Cyclin degradation is a key step governing exit from mitosis and progression into the next cell-cycle. For example, the transition from metaphase to anaphase which marks the end of mitosis in induced by the degradation of cyclin by a ubiquitin-mediated pathway, which in turn leads to the inactivation of cyclin-dependent kinases (cdk) operational at that cycle-cycle stage. As cells enter interphase, cyclin degradation ceases, cyclin accumulates and, as a result of a complex series of post-translational modifications, cyclin /cdk complexes are activated as kinases which drive the cell through mitosis. Cyclin degradation is thus one of the crucial events in exiting mitosis. Indeed, cyclin mutants that retain the ability to activate the cdk complexes, but which cannot be degraded, arrest the cell-cycle in mitosis. Similar cyclin-dependence exists at other points of the cell-cycle as well. Thus, inhibitors of ubiquitin-mediated degradation of a cyclin (such as where the cyclin is chosen from cyclin A, B, C, D1, D2, D3, E or F) can be used as antiproliterative agents.

Yet a further possible substrate of the subject hUbCE is the fos oncogene product, which can undergo ubiquitin-mediated degradation in a cell and has been implicated in neoplastic transformation as well as in mediating the action of a variety of extracellular stimuli. The control of gene expression by c-fos is believed to play a critical role in cellular proliferation and developmental responses, and alterations in the normal pattern of c-fos can lead to oncogenesis. Given the prominence of c-fos as an early response gene, apparent over-expression and prolonged lifetime of c-fos, as may be caused by an inhibitor of the ubiquitin-mediated degradation of c-fos, might sufficiently unbalance the cell-cycle and cause cell death. Alternatively, such inhibitors can be used to mimic the effects of an external stimulus on the cell, such as treatment with a cytokine.

Exemplification

The invention now being generally described, it will be more readily understood by reference to the following examples which are included merely for purposes of illustration of certain aspects and embodiments of the present invention, and are not intended to limit the invention.

We have defined the biochemical roles of hUbCE and E6AP in the E6 stimulated ubiquitination of p53 in vitro and have shown that inhibition of these enzymes in vivo can lead to an inhibition of E6-stimulated p53 degradation. As described in the examples below, inhibition of hUbCE and E6AP enzyme function in vivo causes an inhibition of E6-stimulated p53 degradation. The level of inhibition achieved in the micro-injection experiments in Example 3 was 25–30%. This may be a consequence of not every injected cell achieving high level expression of the injected construct, a phenomenon we have noted before in many different systems. It may also suggest that there is some redundancy in the cellular ubiquitin conjugation machinery, or that the intracellular concentrations of E1, hUbCE and E6AP are not rate-limiting for p53 degradation in the cell line used. All of our data suggest that E6 is absolutely required for ubiquitination of p53 in our in vitro and in vivo assay systems. We are currently investigating the possibility that hUbCE and E6AP are involved in the normal turnover of p53, with the possible involvement of an, as yet, unidentified cellular E6 homolog.

EXAMPLE 1

Cloning and Expression of a Novel Human Ubiquitin-conjugating Enzyme

The cDNA encoding the human ubiquitin-conjugating enzyme of the present invention was cloned from HeLa cells (ATCC CCL2), Briefly, polyadenylated RNA was isolated from cultured HeLa cells and first strand cDNA was prepared following standard protocols (c.f., Chomczynski U.S. Pat. No, 4,843,155; and Sambrook et al. *Molecular Cloning: A Laboratory Manual*, CSHL Press, Cold Spring Harbor, N.Y. (1989)). Using the nested PCR primer sets 5'-(GC)$_3$AAGCTTTAYGARCGGWGGWGTYTTYTT-3' (SEQ ID No. 8), 5'-(GC)$_3$GAATTCACNGCRTAYTTYTTNGTCCCAYTC-3' (SEQ ID No. 9) and 5'-(GC)$_3$AAGCTTCCNGTNGGNG-AYTTRTTYCAYTGGCA-3' (SEQ ID No. 10), 5-(GC)$_3$G-AATTCATNGTNARNGCNGGCGACCA-3' (SEQ ID No. 11), which also provided convenient restriction sites in the PCR products, the coding sequences for the hUbCE gene was amplified from the HeLa cDNA library, and a HindIII-EcoRI fragment therefrom was subsequently ligated into a pBluescript II KS+ phagemid (pKS+ Stratagene catalog no. 212207) for further manipulation. The resulting pKS-hUbCE construct was amplified in XL1-Blue Cells (Strategene Catalog no. 260268), and double stranded construct purified. The nucleic acid sequence determined for the hUbCE clone is represented in SEQ ID NO. 1, and the corresponding deduced amino acid sequence is provided in SEQ ID No. 2.

The hUbCE gene was subsequently sub-cloned from pKS+ into other expression vectors to generate gene constructs for producing the recombinant hUbCE protein in either bacterial or insect cells. In some instances, the recombinant hUbCE was provided with exogenous sequences to produce fusion proteins where the additional sequences of the fusion protein facilitate its purification. For example, after further amplification, the pKS-E2 construct was cut with XhoI and EcoRI, and the fragment containing the hUbCE coding sequence sub-cloned into a pGEX vector (Pharmacia catalog no. PGEX-4T) previously digested with SalI and EcoRI. The resulting pGEX-hUbCE construct encoded a glutathione-S-transferase (GST)/hUbCE fusion (Smith et al. (1988) *Gene* 67:31–40). The pGEX construct was introduced into *E. coli* by transformation, and the transformants grown in liquid media (LB) in the presence of IPTG. Purification of GST/hUbCE fusion protein was by standard protocols (*Current Protocols in Molecular Biology*, eds. Ausubel ct al. (NY:John Wiley & Sons, 1991); Pharmacia instruction booklet (for catalog no. 27-4570)) using a glutathione-sepharose column (Pharmacia catalog no. 27-4570). Treatment with thrombin removed the GST domain from the fusion protein.

Alternatively, the hUbCE coding sequence was excised from the pKS-hUbCE construct as a HindIII-EcoRI fragment and ligated into pVL1393 cut with Sma I and Eco I. Briefly, the hUbCE gene fragment was purified by agarose gel separation, and ligated into the baculorvirus vector pVL1393 (Invitrogen catalog no. V1392-20) previously cut with Sma I and Bgl II. The pVL1393-hUbCE construct was then used to transfect spodoptera frugiperda (Sf9 cells, ATCC CRL 1711), and the cells maintained in insect cell culture media (Grace's Antheraea medium) supplemented with 10% FBS, lactal bumin hydrolysate, TC yeastolate and glutamate (Invitrogen catalog no. B823) following standard protocols (Invitrogen product guide; Summers and Smith (1987); *Texas Agricultural Experiment Station Bulletin No.* 1555, College Station, Tex.; Luckow et al. (1988) *Bio/technology* 6:47–55; and Miller et al., in *Genetic Engineering*, Vol. 8 ed. Setlow and Hollaender (Plenum Press: New York) pages 277–298). Transfected cells are grown until cells begin to lose their adherence to the culture plate surface, at which time the cells are harvested, collected by centrifugation, and lysed. The lysate is clarified by centrifugation to remove the cell wall debris, and the hUbCE can be purified from the lysate.

For instance, the hUbCE protein was isolated on an E1:ubiquitin charged column. Isolation of enzymes of the ubiquitin-conjugating system has been greatly assisted by "covalent" ubiquitin-affinity chromatography (Crechanover et al. (1982) *J. Biol. Chem.* 257:2537–2542; and Pickart et al. (1985) *J. Biol. Chem.* 260:1573–1581). This method takes advantage of the fact that the E1 enzyme is capable of forming a thiol ester with immobilized ubiquitin (e.g. ubiquitin-Sepharose) in the presence of ATP. Moreover, E1 enzymes bound to the immobilized ubiquitin can be exchanged with the subject hUbCE protein. Thus, both E1 and the subject hUbCE protein can be specifically purified on such columns, and can be recovered after elution with, for example, dithiothreitol. Moreover, with minor changes, this protocol can be used to isolate hUbCE:Ub conjugates (e.g. activated ubiquitin conjugates) for use in therapeutic target assays.

As described in U.S. patent application Ser. No. 08/176,9375 the an E1-containing lysate was applied to a sepharose-ubiquitin column (Hershko et al. (1983) *J Biol. Chem.* 257:2537–2542) in the presence of ATP (e.g. 5 mM ATP, 10 mM MgCl$_2$, and 0.2 mM dithiothreitol, 50 mM Tris-HCl (pH 7.2)). The column was washed several times with this buffer. A clarified lysate of the hUbCE -producing insect cells, adjusted to 50 mM Tris-HCl (pH 7.2), 5 mM ATP, 10 mM MgCl$_2$, and 0.2 mM dithiothreitol, was then applied to the Ub:E1 column, washed, then eluted to remove any remaining ub:E1 (e.g. hUbCE will be exchanged for E1 on the column). The subject hUbCE protein was then eluted from the column by washing with 50 mM Tris-HCl (pH 9.0) containing 2 mM dithiothreitol.

In another exemplary embodiment, the recombinant hUbCE protein is generated as a poly(His) fusion protein for purification on a Ni$^{2+}$ metal column. An XhoI to EcoRI fragment of the pKS construct is cloned into the pBlueBac A baculovirus (Intvitrogen catalog no. V360-20) previously digested with XhoI and EcoRI. Following the manufacturer's protocols, the His$_6$-hUbCE fusion protein is then expressed in Sf9 insect cells, and purified on a Ni$^{2+}$ charged sepharose resin (Invitrogen catalog no. R801; see also Hochuli et al. (1987) *J. Chromatography* 411:177–184; and Janknecht et al. (1991) *PNAS* 88:8972–8976). Following purification of the fusion protein, the His$_6$ tag can be removed by treatment with entrokinase.

EXAMPLE 2

In vitro ubiquitination of p53

We describe the cloning of a new human ubiquitin-conjugation enzyme hUbCE in Example 1. In Examples 4 and 5, we show that hUbCE specifically ubiquitinylates E6AP and is involved in the turnover of p53 in vivo. We have defined several discrete biochemical steps in the activation and transfer of ubiquitin onto p53. These biochemical reactions provide two levels of specificity in the ubiquitination of p53; the hUbCE dependent ubiquitination of E6AP, and the E6-dependent transfer of ubiquitin from ubiquitinylated E6AP to p53.

Proteins

To perform an in vitro ubiquitination reaction, native hUbCE and UBC2, the human homolog of the *S. cerevisiae* DNA repair gene, Rad6 (Koken et al. (1991) *PNAS* 88:8865–8869) were expressed and purified from *E. coli* BL21(DE3). Both proteins are readily soluble and easily purified using standard procedures. The cloning and purification of each of the proteins hUbCE, UBC2, p53, human E1, E6, and E6AP have been described in U.S. Ser. No. 08/247,904. Briefly, native p53 was expressed from the baculoviral vector pVL1392 in Sf9 insect cells according to the manufacturer's instructions (Pharmingen) and purified on a p53 affinity column. HPV18 E6 was expressed *E. coli* BL21 as a GST fusion protein and purified on GSH-sepharose. Human E1 was cloned by PCR from the published cDNA sequence (Handley et al. (1991) *PNAS* 88:258–262), and native protein was expressed and purified from baculoviral infected cells. E6AP was expressed in *E. coli* JM109 as a GST fusion protein and purified on GSH-sepharose.

Ubiquitination reactions

Ubiquitination reactions contained 50–200 ng of the indicated proteins in 50 mM Tris pH 7.5, 5 mM MgCl$_2$, 2mM ATP-γ-S, 0.1 mM DTT and 5 µM ubiquitin. Total reactions (30 µl) were incubated at 25° C. for 3 hrs and then loaded on an 8% SDS gel for analysis of p53 ubiquitination or a 4–20% gradient gel for analysis of ubiquitination of the ubiquitin-conjugating enzymes and E6AP. The gels were run and proteins were electrophoretically transferred to nitrocellulose. p53 proteins were revealed with the monoclonal antibody DO-1 (Oncogene Science) and the ECL system from NEN. Ubiquitinylated proteins were visualized using Extravidin-HRP from Sigma and the ECL system from NEN.

Figure 6:
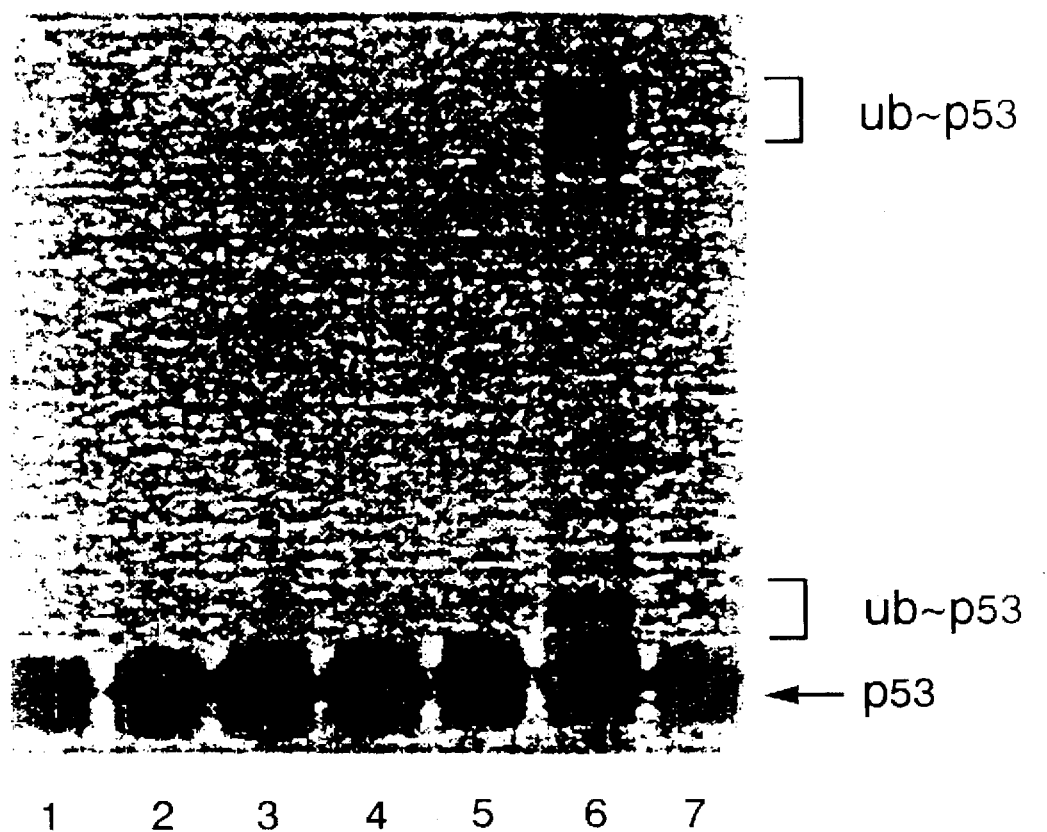
FIG. 6 illustrate the hUbCE dependent ubiquitination of p53 in an in vitro ubiquitination reaction. A complete ubiquitination reaction shown in lane 6 contained E1, hUbCE, E6, E6AP, p53 and ubiquitin. The following changes were made in lanes 1–5: lane 1 no E6, lane 2 no E6AP, lane 3 UBC2 replaces hUbCE, lane 4 no E1, lane 5 no ubiquitin. In lane 7 mutant hUbCE (Cys85→Ser) replaces wild-type hUbCE.

As demonstrated in FIG. 6, the appearance of specific p53-ubiquitin conjugates requires hUbCE, HPV18-E6, E6AP, ubiquitin and E1, the ubiquitin activating enzyme. In contrast, UBC2 was active in a minimal conjugation reaction containing E1, ATP and ubiquitin, in that E1 could activate ubiquitin and transfer it onto UBC2. However, UBC2 could not substitute for hUbCE in the p53 conjugation reaction (FIG. 2, lane 3). In addition, we made an active site cysteine-to-serine mutation in hUbCE. Such active site E2 mutants should accept activated ubiquitin from E1 but should not ubiquitinylate their downstream substrates owing to the high stability of the esther linkage formed between the active site serine and the carboxy-terminus of ubiquitin. This mutant was inactive in the p53 conjugation reaction (FIG. 6, lane 7). These results demonstrate that a catalytically active hUbCE is absolutely required for generation of ubiquitinylated p53 in this in vitro system.

Figure 7A:
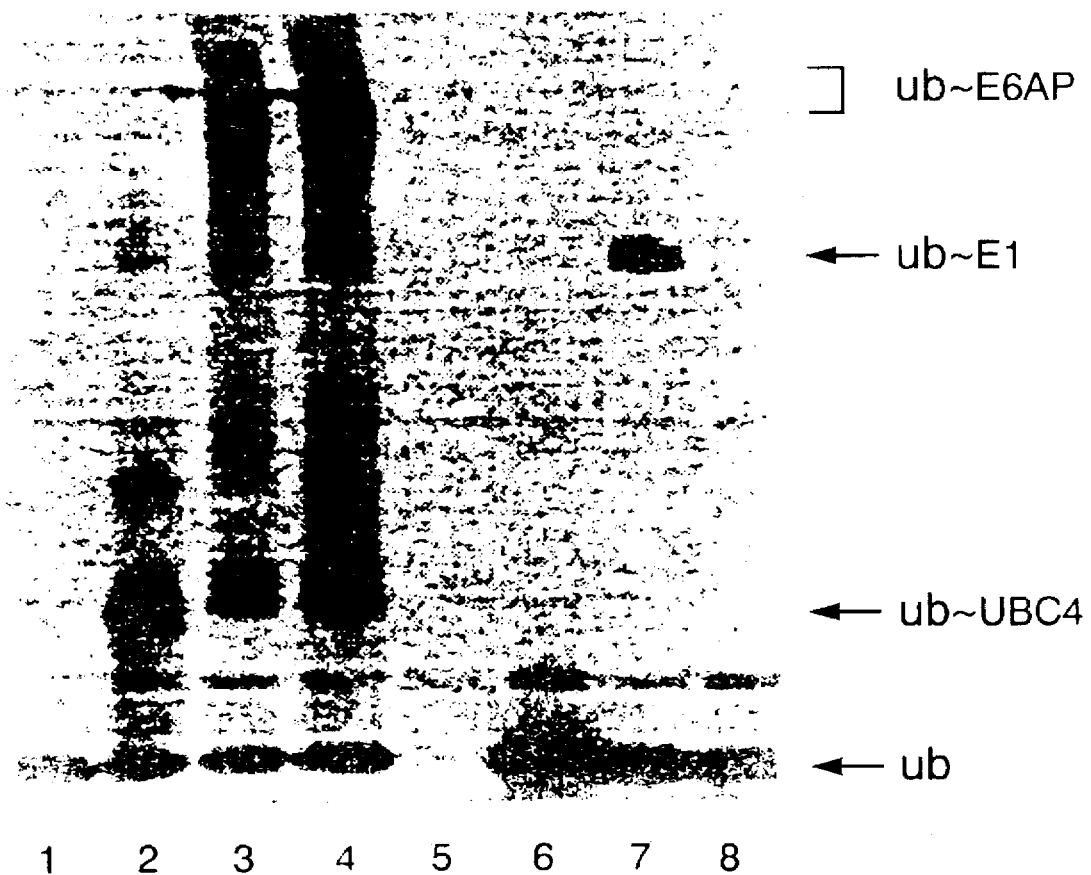
FIG. 7A shows the ubiquitination of E6AP. Purified proteins were used in ubiquitination reactions containing biotinylated ubiquitin. Lane 1 ubiquitin, lane 2 E1, ubiquitin and hUbCE, lane 3 E1, ubiquitin, hUbCE and E6AP, lane 4 E1, ubiquitin, hUbCE, E6AP and E6, lane 5 E1, hUbCE, E6AP and E6, lane 6 ubiquitin, hUbCE and E6AP, lane 7 E1, ubiquitin and E6AP, lane 8 ubiquitin and E6AP.

In FIG. 7A we show that ubiquitinated E1 could transfer ubiquitin efficiently to hUbCE but not directly to E6AP and that ubiquitinated hUbCE transferred ubiquitin to E6AP in a reaction that was not further stimulated by E6. All of these ubiquitination reactions required the presence of the ubiquitin-activating enzyme, E1, and ubiquitin.

Figure 7B:
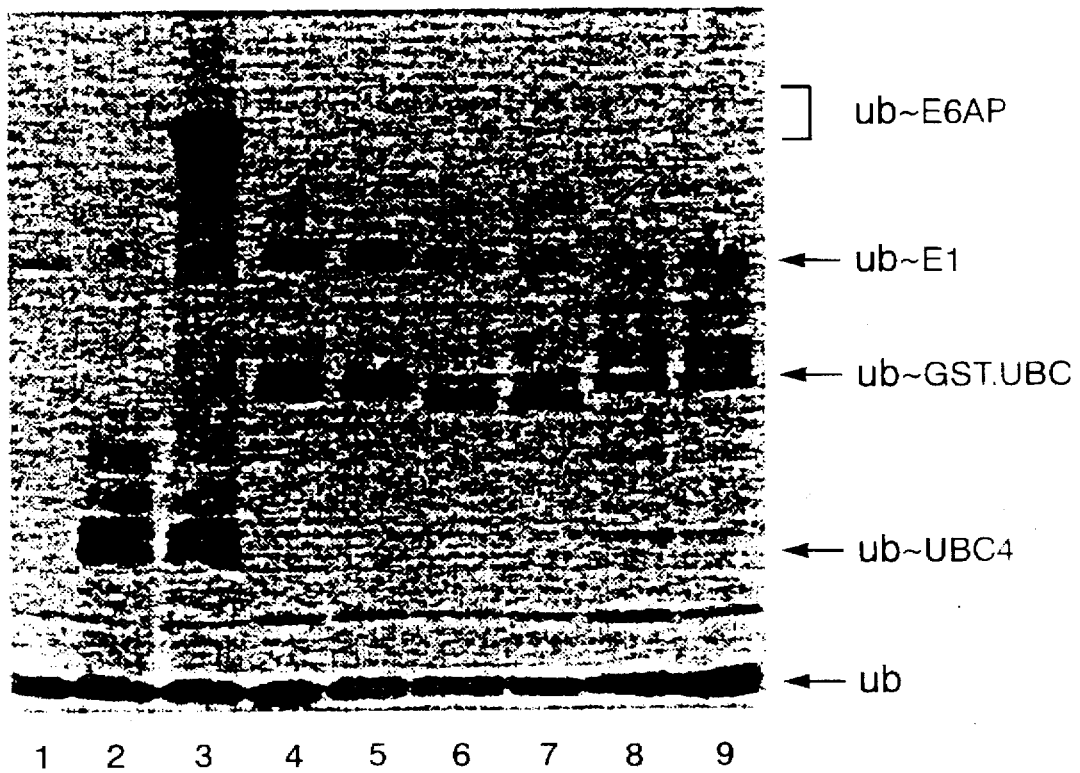
FIG. 7B demonstrates the hUbCE-specific ubiquitination of E6AP. All lanes contained E1 and ubiquitin with the following additions: lane 1 nothing, lane 2 hUbCE, lane 3 hUbCE and E6AP, lane 4 GST.UBC8, lane 5 GST.UBC8 and E6AP, lane 6 GST.UBC2, lane 7 GST.UBC2 and E6AP, lane 8 GST.epiUBC, lane 9 GST.epiUBC and E6AP.

To address the issue of the specificity of hUbCE-mediated ubiquitination of E6AP we performed ubiquitination reactions with purified recombinant hUbCE, GST-UBC2, GST-UBC8 (Kaiser et al. (1994) *J Biol. Chem.* 269:8797–8802) and a GST-fusion of the so-called epidermal ubiquitin conjugating enzyme (Liu et al. (1992) *J Biol Chem* 267:15829–15835). Each of these recombinant proteins could accept activated ubiquitin from E1, but only hUbCE could donate ubiquitin to E6AP (FIG. 7B). We also confirmed that native UBC2 could accept ubiquitin from E1 but could not donate ubiquitin to E6AP (data not shown).

We then purified the ubiquitinated E6AP by affinity chromatography on glutathione-Sepharose and demonstrated that it did not contain appreciable amounts of ubiquitinated E1, ubiquitinylated hUbCE or free ubiquitin. We found that this purified, ubiquitinated E6AP could donate ubiquitin to p53 in an E6-dependent reaction.

EXAMPLE 3

Microinjection of Sense and Anti-sense constructs of the hUbCE Gene

To investge the consequences of interfering with hUbCE and E6AP function in p53 degradation, we performed microinjection experiments using sense and anti-sense constructs of the hUbCE gene. To facilitate the detection of p53 by indirect immunofluorescence, the experiments were performed in the human tumor cell line MDA-MB-468 which contain high levels of mutant p53 (Arg273His). In this line, the degradation of p53 could be stimulated by microinjection of an HPV-18 E6 expression plasmid.

Figure 8:
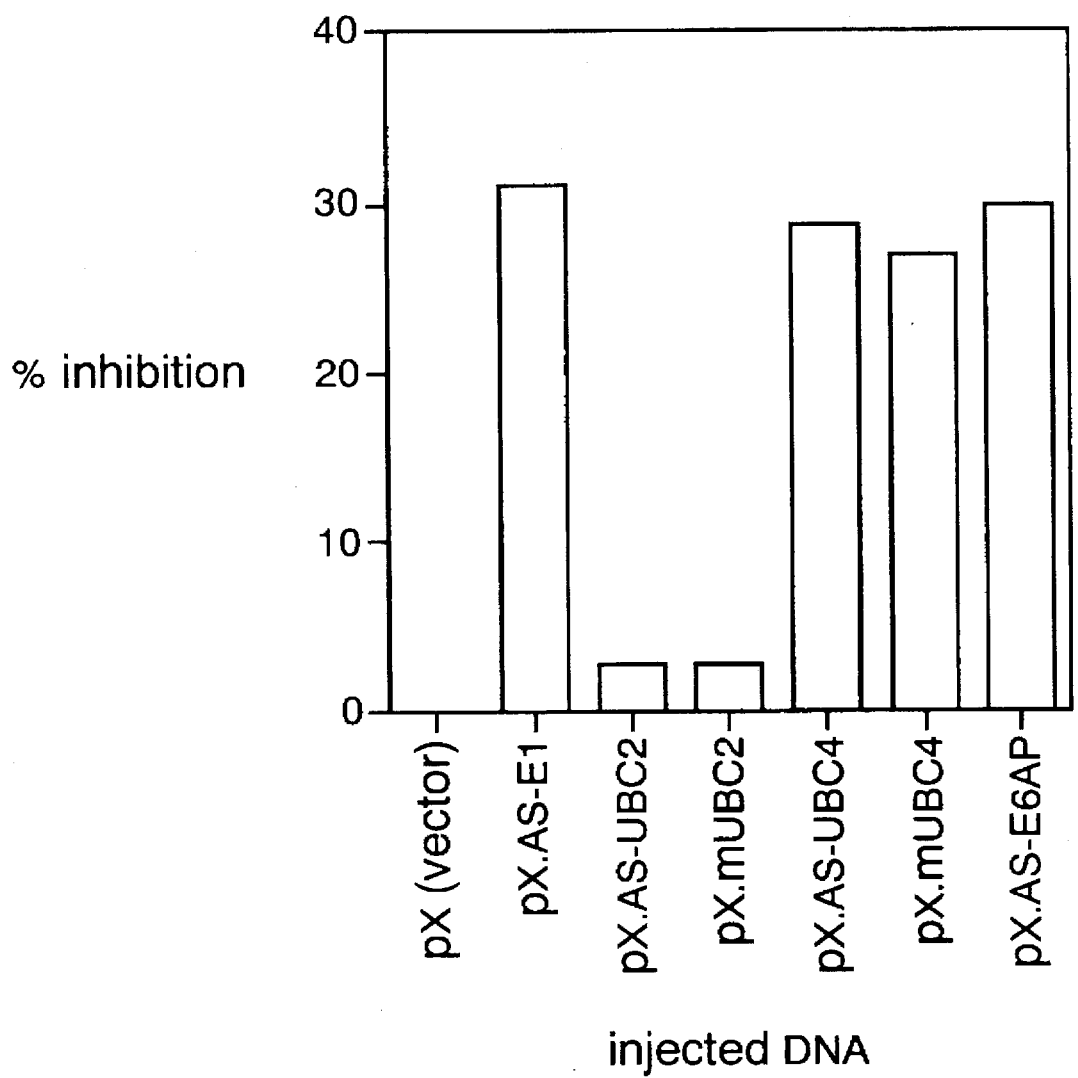
FIG. 8 shows the degree of inhibition of E6 stimulated p53 degradation in co-injection experiments. The indicated DNAs were co-injected with pX.E6. The levels of inhibition of the E6 stimulated p53 degradation are derived from an analysis of approx. 150 injected cells per experimental point in at least two independent experiments.

In order to determine whether hUbCE and E6AP mediate the E6-dependent ubiquitination and degradation of p53 in vivo co-injection experiments were performed. To briefly describe the experiments, the CMV expression vectors were obtained by inserting the entire open-reading frame of one of HPV-18 E6, human E1, human E6-AP, hUbCE, or a Cys-85 mutant of hUbCE, in either a sense or anti-sense orientation (as indicated in FIG. 8) in the pX-plasmid (Baldin et al. (1993) *Genes & Devel.*, 7:812–821). Plasmids were purified with a Promega Wizard Maxi-prep kit and injected at a concentration of 50 to 100 µg/µl in the presence of normal affinity-purified rabbit or mouse antibody (5 mg/ml in PBS) used as microinjection marker.

Cell monolayers of asynchronous MDA-MB-468 cells were injected with the indicated DNAs (FIG. 8) along with rabbit IgG to allow identification of injected cells with an automated microinjection system (AIS, Zeiss; Ansorge et al. (1988) *J. Biochem. Biophys. Meth.*, 16:283–292). All microinjection experiments were carried out in 3.5 cm Petri dishes containing 3 ml of DMEM medium carbonate free, in order to avoid the decrease in pH of the medium during the injection. Each cell was injected at a pressure between 50 and 150 hPa. After 24 hrs the cells were fixed and stained with a p53 specific monoclonal antibody (DO-1; Oncogene Sciences) followed by a biotinylated horse anti-rabbit antibody and Texas red conjugated streptavidin. Injected cells were identified by staining with an FITC conjugated goat anti-rabbit antibody (Baldin et al. (p993) *Genes and Dev* 7:812–821).

When either an anti-sense or mutant hUbCE expression plasmid or an expression plasmid encoding anti-sense E6AP was co-injected with the E6 expression plasmid, the E6 stimulated degradation of p53 was inhibited (FIG. 8). Similar results were obtained when polyclonal antibodies generated against human hUbCE or an expression plasmid encoding a mutant form of E6AP (Peter Howley, pers.comm.) were microinjected (not shown).

Co-injection of an E6 expression plasmid with an expression plasmid encoding anti-sense E1 also inhibited the E6 stimulated degradation of p53. Co-injection of anti-sense or mutant UBC2 expression plasmids had a negligible effect on the E6 stimulated degradation of p53 (FIG. 8).

Moreover, the data show that an hUbCE mutant, Cys-85→Ser, which produces an inactive form of the enzyme, is possibly a dominant negative mutant able to at least partially rescue p53.

EXAMPLE 4

Generating a Molecular Model of the hUbCE protein

The three dimensional coordinates of the protein backbone from the structure of UBC1 from *A. thaliana* (Brookhaven databank file 1AAK.pdb) were used for homology modeling of hUbCE. Modeling was performed with the Protein Workbench software package of QUANTA, version 4 (MSI, Burlington Mass.).

Briefly, the amino acid sequence of hUbCE (SEQ ID No. 2) and UBC1 were aligned using the alignment program in QUANTA. This alignment shows a 44% match of similar residues. The coordinates of the backbone non-hydrogen atoms were then copied onto the hUbCE sequence, sidechain coordinates for the hUbCE model were a ignored at this point. The resulting hUbCE structure was then energy minimized using 200 steps of the steepest descent algorithm followed by 5000 steps of the adopted-base Newton Raphson algorithm. All atoms, including polar hydrogens and all side chains were allowed to move. The resulting CHARMM energy of the system was −7084.2 kcal.

In the next step, the structure was heated up to 500° K using 2000 steps or a total time of 2 psec. After heating, the system was then allowed to equilibrate for 9 psec (9000 steps). The final CHARMM energy after 10 psec was around −5750 kcal. Finally, the system was cooled down to 300° K in steps of 50° K (1 psec cooling, 4 psec equilibration) and finally equilibrated at 300° K for 6 psec. The final total CHARMM energy was around −6650 kcal. The final structure showed no serious conformational strains or improper angles. The atomic coordinates for the full length model are shown in FIG. 1.

In the next step we modeled the 4-meric peptide Ala-Ile-Arg-Gly into the active site. This peptide was derived from the c-terminal sequence of ubiquitin (RIRG). A thioester bond was manually constructed in both cases between the C-terminal Gly and the active site cyteseines. The system was energy-minimized and subsequently subjected to molecular dynamics simulations. In both cases the Ile residue of the peptide settles into the hydrophobic pocket. There are two backbone-backbone hydrogen bonds between the loops and the peptide. The Arg of the peptide forms hydrogen bonds with a conserved Asp residue (between the conserved Val and Ile residues) in both cases.

The general tight fit of the peptide into the active-site cleft makes us very confident that this area is also the docking site for ubiquitin. We will use this structural information for the construction of various mutants which we believe will no longer bind ubiquitin. We will also use this three-dimensional information for the design of inhibitory peptides or peptidomimetics. The coordinates for the subset of residues determined to be of greatest import in rational drug design are shown in FIG. 2.

EXAMPLE 5

Cloning of Yeast UbCE Genes

In order to clone homologs of the hUbCE gene, degenerate oligonucleotides based on the conserved regions PVGDDLFHWH/Q and ITLAPSW (see SEQ ID No. 1) were designed and used to amplify S. pombe genomic DNA and cDNA in λZAP (strain h+Nhis3-) and C. albicans genomic and cDNA in λZAP (strain 3153A). The amplification consisted of 30 cycles of 94° C. for 1 minute, 55° C. for 1 minute and 72° C. for 1 minute. The PCR reactions were separated on a 2.5% low melting agarose gel, that identified a 250 hp fragment for both genomic and complementary DNA from C. albicans. From S. pombe 250 and 650 bp fragments were detected for complementary and genomic DNA respectively. The size discrepancy between complementary DNA and genomic S. pombe DNA fragments probably reflects the presence of an intron. The fragments of 250 bps were eluted and cloned into pCRII (TA cloning system, Invitrogen corporation).

The S. pombe and C. albicans DNA probes were 32p labeled by nick translation and used on Southern blots to confirm the species identity of the fragments and to screen S. pombe and C. albicans cDNA libraries. Sequencing of the full length cDNAs confirmed the identity of the clones. The C. albicans and S. pombe UbCE open-reading frames are both 147 aa residues long (SEQ ID Nos: 3 and 5, respectively). The newly isolated genes are named caUbCE and spUbCE for C. albicans and S. pombe respectively.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid comprising a nucleotide sequence which encodes a ubiquitin conjugating enzyme (UbCE) polypeptide having an amino acid sequence at least 95% identical to at least one of SEQ ID Nos. 2, 4 or 6, which UbCE polypeptide catalyzes ubiquitin conjugation.

2. An isolated nucleic acid comprising a nucleotide sequence encoding an UbCE polypeptide comprising an amino acid sequence at least 95% homologous to SEQ ID NO. 2, which UbCE polypeptide specifically binds at least one of an E6 AP protein, a papillomavirus E6 protein, or p53.

3. The nucleic acid of claim 1 or 2, further comprising a transcriptional regulatory sequence operably linked to said nucleotide sequence so as to render said nucleotide sequence along with said transcriptional regulatory sequence suitable for use as an expression vector.

4. An expression vector, capable of replicating in at least one of prokaryotic cell or eukaryotic cell, comprising the nucleic acid of claim 1 or 2.

5. A host cell transfected with the expression vector of claim 4 and expressing said UbCE polypeptide.

6. A method of producing a recombinant ubiquitin conjugating enzyme comprising culturing the cell of claim 5 in a cell culture medium to express said UbCE polypeptide and isolating said UbCE polypeptide from said cell culture.

7. The nucleic acid of claim 1, wherein said UbCE polypeptide has an amino acid sequence at least 95% identical to the amino acid sequence of SEQ ID No. 2.

8. The nucleic acid of claim 1 or 2, wherein said UbCE polypeptide has an amino acid sequence at least 97% identical to the amino acid sequence of SEQ ID No. 2.

9. The nucleic acid of claim 8, wherein said UbCE polypeptide has an amino acid sequence represented by SEQ ID No. 2.

10. The nucleic acid of claim 1, wherein the UbCE polypeptide has an amino acid sequence at least 95% identical to the amino acid sequence of SEQ ID No. 4.

11. The nucleic acid of claim 1, wherein said UbCE polypeptide has an amino acid sequence at least 97% identical to the amino acid sequence of SEQ ID No. 4.

12. The nucleic acid of claim 1, wherein said UbCE polypeptide has an amino acid sequence represented by SEQ ID No. 4.

13. The nucleic acid of claim 1, wherein said UbCE polypeptide has an amino acid sequence at least 95% identical to the amino acid sequence of SEQ ID No. 6.

14. The nucleic acid of claim 1, wherein said UbCE polypeptide has an amino acid sequence at least 97% identical to the amino acid sequence of SEQ ID No. 6.

15. The nucleic acid of claim 1, wherein said UbCE polypeptide has an amino acid sequence represented by SEQ ID No. 6.

16. The nucleic acid of claim 2, wherein said UbCE polypeptide contains at least one amino acid residue different from SEQ ID No. 2 and which inhibits ubiquitination of a p53 or E6AP protein by an enzyme having a sequence represented by SEQ ID No. 2.

17. The nucleic acid of claim 2, wherein said UbCE polypeptide comprises a dominant negative mutation at the active site cysteine.

18. The nucleic acid of claim 16, wherein said UbCE polypeptide has an ubiquitin conjugating activity which is less than 5 percent of a ubiquitin conjugating enzyme identical to SEQ ID No. 2.

19. The nucleic acid of claim 1, wherein said UbCE polypeptide specifically binds at lease one of an E6-AP protein, a papillomavirus E6 protein, or p53.

20. The nucleic acid of claim 1 or 2, wherein said UbCE polypeptide mediates ubiquitination of a p53 protein.

21. The nucleic acid of claim 1 or 2, wherein said UbCE polypeptide mediates ubiquitination of an E6-AP polypeptide.

22. The nucleic acid of claim 1, wherein said nucleotide sequence which encodes said UbCE polypeptide is the coding sequence of SEQ ID No. 1.

23. The nucleic acid of claim 1, wherein said nucleotide sequence which encodes said UbCE polypeptide is the coding sequence of SEQ ID No. 3.

24. The nucleic acid of claim 1, wherein said nucleotide sequence which encodes said UbCE polypeptide is the coding sequence of SEQ ID No. 5.

25. The nucleic acid of claim 1 or 2, wherein said UbCE polypeptide is comprises within a fusion protein.

26. The nucleic acid of claim 25, wherein said fusion protein is glutathione-S transferase (GST) fusion protein.

27. The nucleic acid of claim 25, wherein said fusion protein includes a purification leader sequence.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 444 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..441

( x i ) SEQUENCE DESCRIPTION: SEQ ID NO:1:

```
ATG GCG CTG AAA CGG ATC CAC AAG GAA TTG AAT GAT CTG GCA CGG GAC      48
Met Ala Leu Lys Arg Ile His Lys Glu Leu Asn Asp Leu Ala Arg Asp
 1               5                  10                  15

CCT CCA GCA CAG TGT TCA GCA GGT CCT GTT GGA GAT GAT ATG TTC CAT      96
Pro Pro Ala Gln Cys Ser Ala Gly Pro Val Gly Asp Asp Met Phe His
                20                  25                  30

TGG CAA GCT ACA ATA ATG GGG CCA AAT GAC AGT CCC TAT CAG GGT GGA     144
Trp Gln Ala Thr Ile Met Gly Pro Asn Asp Ser Pro Tyr Gln Gly Gly
             35                  40                  45

GTA TTT TTC TTG ACA ATT CAT TTC CCA ACA GAT TAC CCC TTC AAA CCA     192
Val Phe Phe Leu Thr Ile His Phe Pro Thr Asp Tyr Pro Phe Lys Pro
 50                  55                  60

CCT AAG GTT GCA TTT ACC ACA AGA ATT TAT CAT CCA AAT ATT AAC AGT     240
Pro Lys Val Ala Phe Thr Thr Arg Ile Tyr His Pro Asn Ile Asn Ser
 65                  70                  75                  80

AAT GGC AGC ATT TGT CTT GAT ATT CTA CGA TCA CAG TGG TCT CCA GCA     288
Asn Gly Ser Ile Cys Leu Asp Ile Leu Arg Ser Gln Trp Ser Pro Ala
             85                  90                  95
```

| | | | | | | | | | | | | | | |
|---|---|---|---|---|---|---|---|---|---|---|---|---|---|---|
| CTA | ACT | ATT | TCA | AAA | GTA | CTC | TTG | TCC | ATC | TGT | TCT | CTG | TTG | TGT | GAT |
| Leu | Thr | Ile | Ser | Lys | Val | Leu | Leu | Ser | Ile | Cys | Ser | Leu | Leu | Cys | Asp |
| | | 100 | | | | | 105 | | | | | 110 | | | |

336

| | | | | | | | | | | | | | | |
|---|---|---|---|---|---|---|---|---|---|---|---|---|---|---|---|
| CCC | AAT | CCA | GAT | GAT | CCT | TTA | GTG | CCT | GAG | ATT | GCT | CGG | ATC | TAC | CAA |
| Pro | Asn | Pro | Asp | Asp | Pro | Leu | Val | Pro | Glu | Ile | Ala | Arg | Ile | Tyr | Gln |
| | | 115 | | | | | 120 | | | | | 125 | | | |

384

| | | | | | | | | | | | | | | |
|---|---|---|---|---|---|---|---|---|---|---|---|---|---|---|---|
| ACA | GAT | AGA | GAA | AAG | TAC | AAC | AGA | ATA | GCT | CGG | GAA | TGG | ACT | CAG | AAG |
| Thr | Asp | Arg | Glu | Lys | Tyr | Asn | Arg | Ile | Ala | Arg | Glu | Trp | Thr | Gln | Lys |
| | 130 | | | | | 135 | | | | | 140 | | | | |

432

TAT GCG ATG TAA
Tyr Ala Met
145

444

( 2 ) INFORMATION FOR SEQ ID NO:2:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Ala Leu Lys Arg Ile His Lys Glu Leu Asn Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Gln
            115                 120                 125

Thr Asp Arg Glu Lys Tyr Asn Arg Ile Ala Arg Glu Trp Thr Gln Lys
        130                 135                 140

Tyr Ala Met
145

( 2 ) INFORMATION FOR SEQ ID NO:3:

( i ) SEQUENCE CHARACTERISTICS:
        ( A ) LENGTH: 582 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 25..465

( x i ) SEQUENCE DESCRIPTION: SEQ ID NO:3:

CACGAGTAAC TATTGCTTTA AATC ATG TCA TTA AAA CGT ATT AAC AAA GAA
                                    Met Ser Leu Lys Arg Ile Asn Lys Glu
                                    1                   5

51

```
TTA TCT GAC TTA GGA AGA GAT CCA CCA TCA TCA TGT TCA GCC GGT CCA        99
Leu Ser Asp Leu Gly Arg Asp Pro Pro Ser Ser Cys Ser Ala Gly Pro
 10              15                  20                  25

GTT GGA GAT GAC TTA TAC CAC TGG CAA GCA TCT ATC ATG GGA CCA CCA       147
Val Gly Asp Asp Leu Tyr His Trp Gln Ala Ser Ile Met Gly Pro Pro
                 30                  35                  40

GAC TCT CCA TAC GCT GGT GGG GTA TTT TTC TTG AGT ATC CAT TTC CCA       195
Asp Ser Pro Tyr Ala Gly Gly Val Phe Phe Leu Ser Ile His Phe Pro
             45                  50                  55

ACA GAT TAT CCT TTA AAA CCA CCA AAG ATT GCT TTA ACA ACA AAA ATC       243
Thr Asp Tyr Pro Leu Lys Pro Pro Lys Ile Ala Leu Thr Thr Lys Ile
         60                  65                  70

TAT CAT CCA AAT ATT AAT AGT AAT GGT AAC ATC TGT TTA GAT ATC TTA       291
Tyr His Pro Asn Ile Asn Ser Asn Gly Asn Ile Cys Leu Asp Ile Leu
     75                  80                  85

AAG GAT CAA TGG TCA CCT GCA TTA ACA ATT TCC AAA GTG TTA TTG TCT       339
Lys Asp Gln Trp Ser Pro Ala Leu Thr Ile Ser Lys Val Leu Leu Ser
 90                  95                 100                 105

ATT TGT TCA TTA TTA ACT GAT GCC AAC CCA GAC GAT CCA TTA GTG CCA       387
Ile Cys Ser Leu Leu Thr Asp Ala Asn Pro Asp Asp Pro Leu Val Pro
             110                 115                 120

GAA ATC GCT CAC ATT TAT AAA CAA GAT AGA AAG AAG TAT GAA GCT ACT       435
Glu Ile Ala His Ile Tyr Lys Gln Asp Arg Lys Lys Tyr Glu Ala Thr
         125                 130                 135

GCC AAA GAA TGG ACT AAG AAA TAT GCT GTG TGATTTTAGA GAAAAACAAA         485
Ala Lys Glu Trp Thr Lys Lys Tyr Ala Val
     140                 145

AACATCTAAT TTCTACATGT ATTATGTCGT AATGCTTTCA CACAATACAA AAACATCTAA     545

TTTCTACATG TATTATGTCG TAATGCTTTC ACACAAT                              582
```

( 2 ) INFORMATION FOR SEQ ID NO:4:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Leu Lys Arg Ile Asn Lys Glu Leu Ser Asp Leu Gly Arg Asp
 1               5                  10                  15

Pro Pro Ser Ser Cys Ser Ala Gly Pro Val Gly Asp Asp Leu Tyr His
                 20                  25                  30

Trp Gln Ala Ser Ile Met Gly Pro Pro Asp Ser Pro Tyr Ala Gly Gly
             35                  40                  45

Val Phe Phe Leu Ser Ile His Phe Pro Thr Asp Tyr Pro Leu Lys Pro
 50                  55                  60

Pro Lys Ile Ala Leu Thr Thr Lys Ile Tyr His Pro Asn Ile Asn Ser
 65                  70                  75                  80

Asn Gly Asn Ile Cys Leu Asp Ile Leu Lys Asp Gln Trp Ser Pro Ala
                 85                  90                  95

Leu Thr Ile Ser Lys Val Leu Leu Ser Ile Cys Ser Leu Leu Thr Asp
             100                 105                 110

Ala Asn Pro Asp Asp Pro Leu Val Pro Glu Ile Ala His Ile Tyr Lys
             115                 120                 125

Gln Asp Arg Lys Lys Tyr Glu Ala Thr Ala Lys Glu Trp Thr Lys Lys
 130                 135                 140

Tyr Ala Val
```

( 2 ) INFORMATION FOR SEQ ID NO:5:

( i ) SEQUENCE CHARACTERISTICS:
        ( A ) LENGTH: 522 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 22..462

( x i ) SEQUENCE DESCRIPTION: SEQ ID NO:5:

```
CGCAAAAGCA AACCAGTAAC G ATG GCT TTG AAA AGA ATT AAC CGT GAA TTA         51
                        Met Ala Leu Lys Arg Ile Asn Arg Glu Leu
                         1           5                      10

GCT GAT CTT GGA AAA GAC CCA CCG TCT TCT TGT TCC GCC GGC CCT GTT         99
Ala Asp Leu Gly Lys Asp Pro Pro Ser Ser Cys Ser Ala Gly Pro Val
                 15                  20                  25

GGC GAT GAT TTA TTC CAT TGG CAA GCT ACA ATC ATG GGT CCT GCT GAC        147
Gly Asp Asp Leu Phe His Trp Gln Ala Thr Ile Met Gly Pro Ala Asp
             30                  35                  40

AGC CCT TAT GCG GGT GGT GTC TTC TTC TTG TCC ATT CAT TTC CCT ACG        195
Ser Pro Tyr Ala Gly Gly Val Phe Phe Leu Ser Ile His Phe Pro Thr
         45                  50                  55

GAC TAC CCA TTC AAG CCA CCA AAG GTA AAC TTT ACA ACC AGA ATC TAT        243
Asp Tyr Pro Phe Lys Pro Pro Lys Val Asn Phe Thr Thr Arg Ile Tyr
     60                  65                  70

CAT CCC AAC ATC AAT TCA AAC GGT AGC ATT TGT TTG GAT ATC CTT CGT        291
His Pro Asn Ile Asn Ser Asn Gly Ser Ile Cys Leu Asp Ile Leu Arg
 75                  80                  85                  90

GAC CAA TGG TCT CCA GCG TTG ACT ATA TCA AAG GTA TTA CTG TCT ATC        339
Asp Gln Trp Ser Pro Ala Leu Thr Ile Ser Lys Val Leu Leu Ser Ile
                 95                 100                 105

TGC TCA TTG TTG ACA GAT CCT AAT CCT GAT GAT CCG CTT GTG CCT GAA        387
Cys Ser Leu Leu Thr Asp Pro Asn Pro Asp Asp Pro Leu Val Pro Glu
             110                 115                 120

ATT GCG CAC GTC TAC AAA ACT GAC AGA TCC CGT TAT GAA TTA AGT GCT        435
Ile Ala His Val Tyr Lys Thr Asp Arg Ser Arg Tyr Glu Leu Ser Ala
         125                 130                 135

CGT GAA TGG ACT AGA AAA TAC GCA ATC TAGAGTTTGT TTCTGTGTTG              482
Arg Glu Trp Thr Arg Lys Tyr Ala Ile
     140                 145

ATATTAAATA TTCATCTCTT AAAAAAAAAA AAAAAACTCG                            522
```

( 2 ) INFORMATION FOR SEQ ID NO:6:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Leu Lys Arg Ile Asn Arg Glu Leu Ala Asp Leu Gly Lys Asp
 1               5                  10                  15

Pro Pro Ser Ser Cys Ser Ala Gly Pro Val Gly Asp Asp Leu Phe His
                 20                  25                  30

Trp Gln Ala Thr Ile Met Gly Pro Ala Asp Ser Pro Tyr Ala Gly Gly
```

|   |   |   |   |   | 35 |   |   |   |   | 40 |   |   |   |   | 45 |   |   |
|---|---|---|---|---|----|---|---|---|---|----|---|---|---|---|----|---|---|

Val Phe Phe Leu Ser Ile His Phe Pro Thr Asp Tyr Pro Phe Lys Pro
     50                   55                   60

Pro Lys Val Asn Phe Thr Thr Arg Ile Tyr His Pro Asn Ile Asn Ser
65                   70                  75               80

Asn Gly Ser Ile Cys Leu Asp Ile Leu Arg Asp Gln Trp Ser Pro Ala
             85                  90               95

Leu Thr Ile Ser Lys Val Leu Leu Ser Ile Cys Ser Leu Leu Thr Asp
           100              105              110

Pro Asn Pro Asp Asp Pro Leu Val Pro Glu Ile Ala His Val Tyr Lys
       115              120             125

Thr Asp Arg Ser Arg Tyr Glu Leu Ser Ala Arg Glu Trp Thr Arg Lys
   130              135             140

Tyr Ala Ile
145

( 2 ) INFORMATION FOR SEQ ID NO:7:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:7:

Met Xaa Leu Lys Arg Ile Xaa Xaa Glu Leu Xaa Asp Leu Xaa Xaa Asp
1                5                   10               15

Pro Pro Xaa Xaa Cys Ser Ala Gly Pro Val Gly Asp Asp Xaa Xaa His
            20                 25               30

Trp Gln Ala Xaa Ile Met Gly Pro Asn Asp Ser Pro Tyr Xaa Gly Gly
            35                 40               45

Val Phe Phe Leu Xaa Ile His Phe Pro Thr Asp Tyr Pro Xaa Lys Pro
     50                   55                   60

Pro Lys Xaa Xaa Xaa Thr Thr Xaa Ile Tyr His Pro Asn Ile Asn Ser
65                   70                  75               80

Asn Gly Xaa Ile Cys Leu Asp Ile Leu Xaa Xaa Gln Trp Ser Pro Ala
             85                  90               95

Leu Thr Ile Ser Lys Val Leu Leu Ser Ile Cys Ser Leu Leu Xaa Asp
           100              105              110

Xaa Asn Pro Asp Asp Pro Leu Val Pro Glu Ile Ala Xaa Xaa Tyr Xaa
       115              120             125

Xaa Asp Arg Xaa Xaa Tyr Xaa Xaa Ala Xaa Glu Trp Thr Xaa Lys
   130              135             140

Tyr Ala Xaa
145

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

```
GCGCGCAAGC TTTAYGARGG WGGWGTYTTY TT                                                    32
```

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

```
GCGCGCGAAT TCACNGCRTA YTTYTTNGTC CCAYTC                                                36
```

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

```
GCGCGCAAGC TTCCNGTNGG NGAYTTRTTY CAYTGGCA                                              38
```

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

```
GCGCGCGAAT TCATNGTNAR NGCNGGCGAC CA                                                    32
```